US008617516B2

(12) United States Patent
Wickline et al.

(10) Patent No.: US 8,617,516 B2
(45) Date of Patent: Dec. 31, 2013

(54) UNIVERSAL ANCHOR PEPTIDE FOR NANOPARTICLES

(75) Inventors: Samuel A. Wickline, St. Louis, MO (US); Hua Pan, St. Louis, MO (US); Neelesh R. Soman, St. Louis, MO (US); Gregory M. Lanza, St. Louis, MO (US); Paul H. Schlesinger, St. Louis, MO (US)

(73) Assignee: Washington University, St. Louis, MO (US)

( * ) Notice: Subject to any disclaimer, the term of this patent is extended or adjusted under 35 U.S.C. 154(b) by 361 days.

(21) Appl. No.: 12/910,385

(22) Filed: Oct. 22, 2010

(65) Prior Publication Data

US 2011/0123438 A1    May 26, 2011

Related U.S. Application Data

(63) Continuation-in-part of application No. PCT/US2009/041000, filed on Apr. 17, 2009.

(60) Provisional application No. 61/047,013, filed on Apr. 22, 2008.

(51) Int. Cl.
*A61K 51/00* (2006.01)
*A61M 36/14* (2006.01)

(52) U.S. Cl.
USPC ........ 424/1.69; 424/1.11; 424/1.29; 424/1.65; 514/1.1; 530/300

(58) Field of Classification Search
USPC .......... 424/1.11, 1.29, 1.65, 1.69, 9.32, 9.321, 424/9.322, 9.34, 9.51, 400, 104, 417, 450, 424/489, 490; 514/1, 1.1; 530/300, 324, 530/325, 326, 327, 328, 329
See application file for complete search history.

(56) References Cited

U.S. PATENT DOCUMENTS

| | | | |
|---|---|---|---|
| 6,676,963 B1* | 1/2004 | Lanza et al. | 424/450 |
| 6,821,506 B2* | 11/2004 | Lanza et al. | 424/9.3 |
| 6,869,591 B2* | 3/2005 | Lanza et al. | 424/9.32 |
| 7,001,983 B1 | 2/2006 | Shai et al. | |
| 7,179,449 B2* | 2/2007 | Lanza et al. | 424/9.321 |
| 7,220,401 B2* | 5/2007 | Lanza et al. | 424/9.323 |
| 7,235,227 B2* | 6/2007 | Lanza et al. | 424/9.32 |
| 7,255,875 B2* | 8/2007 | Lanza et al. | 424/455 |
| 7,279,150 B2* | 10/2007 | Lanza et al. | 424/9.361 |
| 7,344,698 B2* | 3/2008 | Lanza et al. | 424/1.29 |
| 7,566,442 B2* | 7/2009 | Lanza et al. | 424/1.29 |
| 7,727,512 B2* | 6/2010 | Lanza et al. | 424/9.361 |
| 7,943,168 B2* | 5/2011 | Schlesinger et al. | 424/455 |
| 8,003,078 B2* | 8/2011 | Lanza et al. | 424/9.365 |

OTHER PUBLICATIONS

Winter et al (Expert Rev. Med. Devices, 2007, vol. 4, No. 2, pp. 137-145).*

Karin. NF-kappaB in cancer: from innocent bystander to major culprit. Nat Rev Cancer 2002;2:301-310.
Karin. Nuclear factor-kappaB in cancer development and progression. Nature 2006;441:431-436.
Pasparakis. Regulation of tissue homeostasis by NF-kappaB signalling: implications for inflammatory diseases. Nat Rev Immunol 2009;9:778-788.
Bhog. Ubiquitylation in innate and adaptive immunity. Nature 2009;458:430-437.
Lopez-Guerra. NF-kappaB as a therapeutic target in chronic lymphocytic leukemia. Expert Opin Ther Targets 2010;14:275-288.
Bidwell. Therapeutic peptides for cancer therapy. Part I—peptide inhibitors of signal transduction cascades. Expert Opin Drug Deliv 2009;6:1033-1047.
Weissmann. Effect of melittin upon cellular and lysosomal membranes. Biochem Pharmacol 1969;18:1771-1775.
Lanza. Nanomedicine opportunities for cardiovascular disease with perfluorocarbon nanoparticles. Nanomedicine (Lond) 2006;1:321-329.
Angelova. Liposome electroformation. Faraday Discuss Chem Soc 1986;81:303-311.
Bacia. Fluorescence correlation spectroscopy. Methods Mol Biol 2007;398:73-84.
Hess. Biological and chemical applications of fluorescence correlation spectroscopy: a review. Biochemistry 2002;41:697-705.
Winter. Emerging nanomedicine opportunities with perfluorocarbon nanoparticles. Expert Rev Med Devices 2007;4:137-145.
Klocek. Thermodynamics of melittin binding to lipid bilayers. Aggregation and pore formation. Biochemistry 2009;48:2586-2596.
Rothwarf. IKK-gamma is an essential regulatory subunit of the IkappaB kinase complex. Nature 1998;395:297-300.
Acharyya et al., "Interplay of IKK/NF-κB signaling in macrophages and myofibers promotes muscle degeneration in Duchenne muscular dystrophy", J Clin Invest, 2007, pp. 889-901, vol. 117, No. 4.
Baud et al., "Is NF-κB a good target for cancer therapy? Hopes and pitfalls", Nat Rev Drug Discov, 2009, pp. 33-40, vol. 8.
Bernal-Mizrachi et al., "The role of NF-κB-1 and NF-κB-2-mediated resistance to apoptosis in lymphomas", Proc Natl Acad Sci USA, 2006, pp. 9220-9225, vol. 103, No. 24.
Boxus et al., "The HTLV-1 Tax interactome", Retrovirology, 2008, pp. 76-99, vol. 5.
Caruthers et al., "Anti-angiogenic perfluorocarbon nanoparticles for diagnosis and treatment of atherosclerosis", Wiley Interdiscip Rev Nanomed Nanobiotechnol, 2009, pp. 311-323, vol. 1.
Garg et al., "Nuclear transcription factor-κB as a target for cancer drug development", Leukemia, 2002, pp. 1053-1068, vol. 16.

(Continued)

*Primary Examiner* — D L Jones
(74) *Attorney, Agent, or Firm* — Polsinelli PC

(57) ABSTRACT

The present invention provides a substantially non-lytic, non-cytotoxic anchor peptide that is capable of stably inserting into lipid membranes. In particular, the invention provides nanoparticles comprising stably inserted anchor peptides, which may be conjugated to a variety of different cargo complexes.

8 Claims, 31 Drawing Sheets

(56) References Cited

OTHER PUBLICATIONS

Grossman et al., "Cytokine Expression and Tumorigenicity of Large Granular Lymphocytic Leukemia Cells From Mice Transgenic for the tax Gene of Human T-Cell Leukemia Virus Type I", Blood, 1997, pp. 783-794, vol. 90, No. 2.

Grossman et al., "Development of leukemia in mice transgenic for the tax gene of human T-cell leukemia virus type I", Proc. Natl Acad Sci USA, 1995, pp. 1057-1061, vol. 92.

Kaneda et al., "Perfluorocarbon Nanoemulsions for Quantitative Molecular Imaging and Targeted Therapeutics", Ann Biomed Eng, 2009, pp. 1922-1933, vol. 37, No. 10.

Karin, "The Beginning of the End: IκB Kinase (IKK) and NF-κB Activation", J Biol Chem, 1999, pp. 27339-27342, vol. 274, No. 39.

May et al., "Selective Inhibition of NF-κB Activation by a Peptide That Blocks the Interaction of NEMO with the IκB Kinase Complex", Science, 2000, pp. 1550-1554, vol. 289.

Pan et al., "Lipid membrane editing with peptide cargo linkers in cells and synthetic nanostructures", FASEB J, 2010, pp. 2928-2937, vol. 24, No. 8.

Petrasek et al., "Precise Measurement of Diffusion Coefficients using Scanning Fluorescence Correlation Spectroscopy", Biophys J, 2008, pp. 1437-1448, vol. 94.

Rhoades et al., "Quantification of α-Synuclein Binding to Lipid Vesicles Using Fluorescence Correlation Spectroscopy", Biophys J, 2006 pp. 4692-4700, vol. 90.

Smale, "Selective Transcription in Response to an Inflammatory Stimulus", Cell, 2010, pp. 833-844, vol. 140, No. 6.

Soman et al., "Molecularly targeted nanocarriers deliver the cytolytic peptide melittin specifically to tumor cells in mice, reducing tumor growth", J Clin Invest, 2009, pp. 2830-2842, vol. 119, No. 9.

Soman et al., "Synthesis and Characterization of Stable Fluorocarbon Nanostructures as Drug Delivery Vehicles for Cytolytic Peptides", Nano Lett., 2008, pp. 1131-1136, vol. 8, No. 4.

Sun et l., "Persistent activation of NF-κB by the Tax transforming protein of HTLV-1: hijacking cellular IκB kinases", Oncogene, 1999, pp. 6948-6958, vol. 18.

Torreri et al., "Biomolecular interactions by Surface Plasmon Resonance Technology", Ann 1st Super Sanita, 2005, pp. 437-441, vol. 41.

Yamaoka et al., "Complementation Cloning of NEMO, a Component of the IκB Kinase Complex Essential for NF-κB Activation", Cell, 1998, pp. 1231-1240, vol. 93.

International Search Report and Written Opinion from related International Application No. PCT/US09/41000, dated Apr. 23, 2010, 10 pgs.

\* cited by examiner

A

B

A

TCP1

VLTTGLPALISWIKRKRQQggVHPKQHR

B

TCP2

VHPKQHRggVLTTGLPALISWIKRKRQQ

C

A

B

C

A

B

A NBD-Linker:
H-TALDWSWLQTEgg*VLTTGLPALISWIKRKRQQ*-OH

C

D

D

E

SEQUENCE LISTING

```
<160> NUMBER OF SEQ ID NOS: 225

<210> SEQ ID NO 1
<211> LENGTH: 6
<212> TYPE: PRT
<213> ORGANISM: Artificial Sequence
<220> FEATURE:
<223> OTHER INFORMATION: based on Apis mellifera

<400> SEQUENCE: 1

Ala Leu Ile Ser Trp Ile
1               5

<210> SEQ ID NO 2
<211> LENGTH: 6
<212> TYPE: PRT
<213> ORGANISM: Artificial Sequence
<220> FEATURE:
<223> OTHER INFORMATION: based on Apis mellifera

<400> SEQUENCE: 2

Ala Trp Ile Ser Trp Ile
1               5

<210> SEQ ID NO 3
<211> LENGTH: 6
<212> TYPE: PRT
<213> ORGANISM: Artificial Sequence
<220> FEATURE:
<223> OTHER INFORMATION: based on Apis mellifera

<400> SEQUENCE: 3

Lys Arg Lys Arg Gln Gln
1               5

<210> SEQ ID NO 4
<211> LENGTH: 8
<212> TYPE: PRT
<213> ORGANISM: Artificial Sequence
<220> FEATURE:
```

-continued

```
<223> OTHER INFORMATION: based on Apis mellifera
<220> FEATURE:
<221> NAME/KEY: MISC_FEATURE
<222> LOCATION: (1)..(1)
<223> OTHER INFORMATION: Xaa = Phe, Met, Ala, Gly, Ile, Leu, Val, Pro,
      Cys, or Trp
<220> FEATURE:
<221> NAME/KEY: MISC_FEATURE
<222> LOCATION: (8)..(8)
<223> OTHER INFORMATION: Xaa = Tyr, Ser, Thr, Lys, His, Gln, Glu, Arg,
      Asp, or Asn

<400> SEQUENCE: 4

Xaa Ala Leu Ile Ser Trp Ile Xaa
1               5

<210> SEQ ID NO 5
<211> LENGTH: 8
<212> TYPE: PRT
<213> ORGANISM: Artificial Sequence
<220> FEATURE:
<223> OTHER INFORMATION: based on Apis mellifera
<220> FEATURE:
<221> NAME/KEY: MISC_FEATURE
<222> LOCATION: (1)..(1)
<223> OTHER INFORMATION: Xaa = Phe, Met, Ala, Gly, Ile, Leu, Val, Pro,
      Cys or Trp
<220> FEATURE:
<221> NAME/KEY: MISC_FEATURE
<222> LOCATION: (8)..(8)
<223> OTHER INFORMATION: Xaa = Tyr, Ser, Thr, Lys, His, Gln, Glu, Arg,
      Asp, or Asn

<400> SEQUENCE: 5

Xaa Ala Trp Ile Ser Trp Ile Xaa
1               5

<210> SEQ ID NO 6
<211> LENGTH: 16
<212> TYPE: PRT
<213> ORGANISM: Artificial Sequence
<220> FEATURE:
<223> OTHER INFORMATION: based on Apis mellifera
<220> FEATURE:
<221> NAME/KEY: MISC_FEATURE
<222> LOCATION: (1)..(1)
<223> OTHER INFORMATION: Xaa = Phe, Met, Ala, Gly, Ile, Leu, Val, Pro,
      Cys or Trp
<220> FEATURE:
<221> NAME/KEY: MISC_FEATURE
<222> LOCATION: (4)..(4)
<223> OTHER INFORMATION: Xaa = Pro, Ala, Met, Leu, Ile, or Trp

<400> SEQUENCE: 6

Xaa Gly Leu Xaa Ala Leu Ile Ser Trp Ile Lys Arg Lys Arg Gln Gln
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: based on Apis mellifera
<220> FEATURE:
<221> NAME/KEY: MISC_FEATURE
<222> LOCATION: (1)..(1)
<223> OTHER INFORMATION: Xaa = Phe, Met, Ala, Gly, Ile, Leu, Val, Pro,
      Cys or Trp
<220> FEATURE:
<221> NAME/KEY: MISC_FEATURE
<222> LOCATION: (4)..(4)
<223> OTHER INFORMATION: Xaa = Pro, Ala, Met, Leu, Ile, or Trp

<400> SEQUENCE: 7
```

```
Xaa Gly Leu Xaa Ala Trp Ile Ser Trp Ile Lys Arg Lys Arg Gln Gln
1               5                   10                  15

<210> SEQ ID NO 8
<211> LENGTH: 18
<212> TYPE: PRT
<213> ORGANISM: Artificial Sequence
<220> FEATURE:
<223> OTHER INFORMATION: based on Apis mellifera
<220> FEATURE:
<221> NAME/KEY: MISC_FEATURE
<222> LOCATION: (1)..(1)
<223> OTHER INFORMATION: Xaa = Phe, Met, Ala, Gly, Ile, Leu, Val, Pro,
      Cys or Trp
<220> FEATURE:
<221> NAME/KEY: MISC_FEATURE
<222> LOCATION: (6)..(6)
<223> OTHER INFORMATION: Xaa = Pro, Ala, Met, Leu, Ile, or Trp

<400> SEQUENCE: 8

Xaa Thr Thr Gly Leu Xaa Ala Leu Ile Ser Trp Ile Lys Arg Lys Arg
1               5                   10                  15

Gln Gln

<210> SEQ ID NO 9
<211> LENGTH: 18
<212> TYPE: PRT
<213> ORGANISM: Artificial Sequence
<220> FEATURE:
<223> OTHER INFORMATION: based on Apis mellifera
<220> FEATURE:
<221> NAME/KEY: MISC_FEATURE
<222> LOCATION: (1)..(1)
<223> OTHER INFORMATION: Xaa = Phe, Met, Ala, Gly, Ile, Leu, Val, Pro,
      Cys or Trp
<220> FEATURE:
<221> NAME/KEY: MISC_FEATURE
<222> LOCATION: (6)..(6)
<223> OTHER INFORMATION: Xaa = Pro, Ala, Met, Leu, Ile, or Trp

<400> SEQUENCE: 9

Xaa Thr Thr Gly Leu Xaa Ala Trp Ile Ser Trp Ile Lys Arg Lys Arg
1               5                   10                  15

Gln Gln

<210> SEQ ID NO 10
<211> LENGTH: 26
<212> TYPE: PRT
<213> ORGANISM: Artificial Sequence
<220> FEATURE:
<223> OTHER INFORMATION: based on Apis mellifera

<400> SEQUENCE: 10

Gly Ile Gly Ala Trp Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 11
<211> LENGTH: 25
<212> TYPE: PRT
<213> ORGANISM: Artificial Sequence
<220> FEATURE:
<223> OTHER INFORMATION: based on Apis mellifera

<400> SEQUENCE: 11

Gly Ile Gly Ala Trp Leu Lys Val Leu Thr Thr Gly Leu Pro Ala Leu
1               5                   10                  15
```

```
Ile Ser Trp Ile Lys Arg Lys Arg Gln
            20                  25

<210> SEQ ID NO 12
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 12

Gly Ile Gly Ala Trp Leu Lys Val Leu Thr Thr Gly Leu Pro Ala Leu
1               5                   10                  15

Ile Ser Trp Ile Lys Arg Lys Arg
            20

<210> SEQ ID NO 13
<211> LENGTH: 25
<212> TYPE: PRT
<213> ORGANISM: Artificial Sequence
<220> FEATURE:
<223> OTHER INFORMATION: based on Apis mellifera

<400> SEQUENCE: 13

Ile Gly Ala Trp Leu Lys Val Leu Thr Thr Gly Leu Pro Ala Leu Ile
1               5                   10                  15

Ser Trp Ile Lys Arg Lys Arg Gln Gln
            20                  25

<210> SEQ ID NO 14
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 14

Ile Gly Ala Trp Leu Lys Val Leu Thr Thr Gly Leu Pro Ala Leu Ile
1               5                   10                  15

Ser Trp Ile Lys Arg Lys Arg Gln
            20

<210> SEQ ID NO 15
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 15

Ile Gly Ala Trp Leu Lys Val Leu Thr Thr Gly Leu Pro Ala Leu Ile
1               5                   10                  15

Ser Trp Ile Lys Arg Lys Arg
            20

<210> SEQ ID NO 16
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 16

Gly Ala Trp Leu Lys Val Leu Thr Thr Gly Leu Pro Ala Leu Ile Ser
1               5                   10                  15
```

```
Trp Ile Lys Arg Lys Arg Gln Gln
            20
```

<210> SEQ ID NO 17
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 17

```
Gly Ala Trp Leu Lys Val Leu Thr Thr Gly Leu Pro Ala Leu Ile Ser
1               5                   10                  15

Trp Ile Lys Arg Lys Arg Gln
            20
```

<210> SEQ ID NO 18
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 18

```
Gly Ala Trp Leu Lys Val Leu Thr Thr Gly Leu Pro Ala Leu Ile Ser
1               5                   10                  15

Trp Ile Lys Arg Lys Arg
            20
```

<210> SEQ ID NO 19
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 19

```
Ala Trp Leu Lys Val Leu Thr Thr Gly Leu Pro Ala Leu Ile Ser Trp
1               5                   10                  15

Ile Lys Arg Lys Arg Gln Gln
            20
```

<210> SEQ ID NO 20
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 20

```
Ala Trp Leu Lys Val Leu Thr Thr Gly Leu Pro Ala Leu Ile Ser Trp
1               5                   10                  15

Ile Lys Arg Lys Arg Gln
            20
```

<210> SEQ ID NO 21
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 21

```
Ala Trp Leu Lys Val Leu Thr Thr Gly Leu Pro Ala Leu Ile Ser Trp
1               5                   10                  15
```

```
Ile Lys Arg Lys Arg
            20

<210> SEQ ID NO 22
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 22

Trp Leu Lys Val Leu Thr Thr Gly Leu Pro Ala Leu Ile Ser Trp Ile
1               5                   10                  15

Lys Arg Lys Arg Gln Gln
            20

<210> SEQ ID NO 23
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 23

Trp Leu Lys Val Leu Thr Thr Gly Leu Pro Ala Leu Ile Ser Trp Ile
1               5                   10                  15

Lys Arg Lys Arg Gln
            20

<210> SEQ ID NO 24
<211> LENGTH: 20
<212> TYPE: PRT
<213> ORGANISM: Artificial Sequence
<220> FEATURE:
<223> OTHER INFORMATION: based on Apis mellifera

<400> SEQUENCE: 24

Trp Leu Lys Val Leu Thr Thr Gly Leu Pro Ala Leu Ile Ser Trp Ile
1               5                   10                  15

Lys Arg Lys Arg
            20

<210> SEQ ID NO 25
<211> LENGTH: 26
<212> TYPE: PRT
<213> ORGANISM: Artificial Sequence
<220> FEATURE:
<223> OTHER INFORMATION: based on Apis mellifera

<400> SEQUENCE: 25

Gly Ile Gly Ala Val Leu Lys Val Leu Thr Thr Gly Leu Ala Ala Leu
1               5                   10                  15

Ile Ser Trp Ile Lys Arg Lys Arg Gln Gln
            20                  25

<210> SEQ ID NO 26
<211> LENGTH: 25
<212> TYPE: PRT
<213> ORGANISM: Artificial Sequence
<220> FEATURE:
<223> OTHER INFORMATION: based on Apis mellifera

<400> SEQUENCE: 26

Gly Ile Gly Ala Val Leu Lys Val Leu Thr Thr Gly Leu Ala Ala Leu
1               5                   10                  15
```

Ile Ser Trp Ile Lys Arg Lys Arg Gln
            20                  25

<210> SEQ ID NO 27
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 27

Gly Ile Gly Ala Val Leu Lys Val Leu Thr Thr Gly Leu Ala Ala Leu
1               5                   10                  15

Ile Ser Trp Ile Lys Arg Lys Arg
            20

<210> SEQ ID NO 28
<211> LENGTH: 25
<212> TYPE: PRT
<213> ORGANISM: Artificial Sequence
<220> FEATURE:
<223> OTHER INFORMATION: based on Apis mellifera

<400> SEQUENCE: 28

Ile Gly Ala Val Leu Lys Val Leu Thr Thr Gly Leu Ala Ala Leu Ile
1               5                   10                  15

Ser Trp Ile Lys Arg Lys Arg Gln Gln
            20                  25

<210> SEQ ID NO 29
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 29

Ile Gly Ala Val Leu Lys Val Leu Thr Thr Gly Leu Ala Ala Leu Ile
1               5                   10                  15

Ser Trp Ile Lys Arg Lys Arg Gln
            20

<210> SEQ ID NO 30
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 30

Ile Gly Ala Val Leu Lys Val Leu Thr Thr Gly Leu Ala Ala Leu Ile
1               5                   10                  15

Ser Trp Ile Lys Arg Lys Arg
            20

<210> SEQ ID NO 31
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 31

Gly Ala Val Leu Lys Val Leu Thr Thr Gly Leu Ala Ala Leu Ile Ser
1               5                   10                  15

```
Trp Ile Lys Arg Lys Arg Gln Gln
            20

<210> SEQ ID NO 32
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 32

Gly Ala Val Leu Lys Val Leu Thr Thr Gly Leu Ala Ala Leu Ile Ser
1               5                   10                  15

Trp Ile Lys Arg Lys Arg Gln
            20

<210> SEQ ID NO 33
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 33

Gly Ala Val Leu Lys Val Leu Thr Thr Gly Leu Ala Ala Leu Ile Ser
1               5                   10                  15

Trp Ile Lys Arg Lys Arg
            20

<210> SEQ ID NO 34
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 34

Ala Val Leu Lys Val Leu Thr Thr Gly Leu Ala Ala Leu Ile Ser Trp
1               5                   10                  15

Ile Lys Arg Lys Arg Gln Gln
            20

<210> SEQ ID NO 35
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 35

Ala Val Leu Lys Val Leu Thr Thr Gly Leu Ala Ala Leu Ile Ser Trp
1               5                   10                  15

Ile Lys Arg Lys Arg Gln
            20

<210> SEQ ID NO 36
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 36

Ala Val Leu Lys Val Leu Thr Thr Gly Leu Ala Ala Leu Ile Ser Trp
1               5                   10                  15
```

```
Ile Lys Arg Lys Arg
            20

<210> SEQ ID NO 37
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 37

Val Leu Lys Val Leu Thr Thr Gly Leu Ala Ala Leu Ile Ser Trp Ile
1               5                   10                  15

Lys Arg Lys Arg Gln Gln
            20

<210> SEQ ID NO 38
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 38

Val Leu Lys Val Leu Thr Thr Gly Leu Ala Ala Leu Ile Ser Trp Ile
1               5                   10                  15

Lys Arg Lys Arg Gln
            20

<210> SEQ ID NO 39
<211> LENGTH: 20
<212> TYPE: PRT
<213> ORGANISM: Artificial Sequence
<220> FEATURE:
<223> OTHER INFORMATION: based on Apis mellifera

<400> SEQUENCE: 39

Val Leu Lys Val Leu Thr Thr Gly Leu Ala Ala Leu Ile Ser Trp Ile
1               5                   10                  15

Lys Arg Lys Arg
            20

<210> SEQ ID NO 40
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 40

Leu Lys Val Leu Thr Thr Gly Leu Ala Ala Leu Ile Ser Trp Ile Lys
1               5                   10                  15

Arg Lys Arg Gln Gln
            20

<210> SEQ ID NO 41
<211> LENGTH: 20
<212> TYPE: PRT
<213> ORGANISM: Artificial Sequence
<220> FEATURE:
<223> OTHER INFORMATION: based on Apis mellifera

<400> SEQUENCE: 41

Leu Lys Val Leu Thr Thr Gly Leu Ala Ala Leu Ile Ser Trp Ile Lys
1               5                   10                  15
```

Arg Lys Arg Gln
            20

<210> SEQ ID NO 42
<211> LENGTH: 19
<212> TYPE: PRT
<213> ORGANISM: Artificial Sequence
<220> FEATURE:
<223> OTHER INFORMATION: based on Apis mellifera

<400> SEQUENCE: 42

Leu Lys Val Leu Thr Thr Gly Leu Ala Ala Leu Ile Ser Trp Ile Lys
1               5                   10                  15

Arg Lys Arg

<210> SEQ ID NO 43
<211> LENGTH: 20
<212> TYPE: PRT
<213> ORGANISM: Artificial Sequence
<220> FEATURE:
<223> OTHER INFORMATION: based on Apis mellifera

<400> SEQUENCE: 43

Lys Val Leu Thr Thr Gly Leu Ala Ala Leu Ile Ser Trp Ile Lys Arg
1               5                   10                  15

Lys Arg Gln Gln
            20

<210> SEQ ID NO 44
<211> LENGTH: 19
<212> TYPE: PRT
<213> ORGANISM: Artificial Sequence
<220> FEATURE:
<223> OTHER INFORMATION: based on Apis mellifera

<400> SEQUENCE: 44

Lys Val Leu Thr Thr Gly Leu Ala Ala Leu Ile Ser Trp Ile Lys Arg
1               5                   10                  15

Lys Arg Gln

<210> SEQ ID NO 45
<211> LENGTH: 18
<212> TYPE: PRT
<213> ORGANISM: Artificial Sequence
<220> FEATURE:
<223> OTHER INFORMATION: based on Apis mellifera

<400> SEQUENCE: 45

Lys Val Leu Thr Thr Gly Leu Ala Ala Leu Ile Ser Trp Ile Lys Arg
1               5                   10                  15

Lys Arg

<210> SEQ ID NO 46
<211> LENGTH: 19
<212> TYPE: PRT
<213> ORGANISM: Artificial Sequence
<220> FEATURE:
<223> OTHER INFORMATION: based on Apis mellifera

<400> SEQUENCE: 46

Val Leu Thr Thr Gly Leu Ala Ala Leu Ile Ser Trp Ile Lys Arg Lys
1               5                   10                  15

Arg Gln Gln

```
<210> SEQ ID NO 47
<211> LENGTH: 18
<212> TYPE: PRT
<213> ORGANISM: Artificial Sequence
<220> FEATURE:
<223> OTHER INFORMATION: based on Apis mellifera

<400> SEQUENCE: 47

Val Leu Thr Thr Gly Leu Ala Ala Leu Ile Ser Trp Ile Lys Arg Lys
1               5                   10                  15

Arg Gln

<210> SEQ ID NO 48
<211> LENGTH: 17
<212> TYPE: PRT
<213> ORGANISM: Artificial Sequence
<220> FEATURE:
<223> OTHER INFORMATION: based on Apis mellifera

<400> SEQUENCE: 48

Val Leu Thr Thr Gly Leu Ala Ala Leu Ile Ser Trp Ile Lys Arg Lys
1               5                   10                  15

Arg

<210> SEQ ID NO 49
<211> LENGTH: 18
<212> TYPE: PRT
<213> ORGANISM: Artificial Sequence
<220> FEATURE:
<223> OTHER INFORMATION: based on Apis mellifera

<400> SEQUENCE: 49

Leu Thr Thr Gly Leu Ala Ala Leu Ile Ser Trp Ile Lys Arg Lys Arg
1               5                   10                  15

Gln Gln

<210> SEQ ID NO 50
<211> LENGTH: 17
<212> TYPE: PRT
<213> ORGANISM: Artificial Sequence
<220> FEATURE:
<223> OTHER INFORMATION: based on Apis mellifera

<400> SEQUENCE: 50

Leu Thr Thr Gly Leu Ala Ala Leu Ile Ser Trp Ile Lys Arg Lys Arg
1               5                   10                  15

Gln

<210> SEQ ID NO 51
<211> LENGTH: 16
<212> TYPE: PRT
<213> ORGANISM: Artificial Sequence
<220> FEATURE:
<223> OTHER INFORMATION: based on Apis mellifera

<400> SEQUENCE: 51

Leu Thr Thr Gly Leu Ala Ala Leu Ile Ser Trp Ile Lys Arg Lys Arg
1               5                   10                  15

<210> SEQ ID NO 52
<211> LENGTH: 17
<212> TYPE: PRT
<213> ORGANISM: Artificial Sequence
<220> FEATURE:
<223> OTHER INFORMATION: based on Apis mellifera
```

```
<400> SEQUENCE: 52

Thr Thr Gly Leu Ala Ala Leu Ile Ser Trp Ile Lys Arg Lys Arg Gln
1               5                   10                  15

Gln

<210> SEQ ID NO 53
<211> LENGTH: 16
<212> TYPE: PRT
<213> ORGANISM: Artificial Sequence
<220> FEATURE:
<223> OTHER INFORMATION: based on Apis mellifera

<400> SEQUENCE: 53

Thr Thr Gly Leu Ala Ala Leu Ile Ser Trp Ile Lys Arg Lys Arg Gln
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: based on Apis mellifera

<400> SEQUENCE: 54

Thr Thr Gly Leu Ala Ala Leu Ile Ser Trp Ile Lys Arg Lys Arg
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: based on Apis mellifera

<400> SEQUENCE: 55

Thr Gly Leu Ala Ala Leu Ile Ser Trp Ile Lys Arg Lys Arg Gln Gln
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: based on Apis mellifera

<400> SEQUENCE: 56

Thr Gly Leu Ala Ala Leu Ile Ser Trp Ile Lys Arg Lys Arg Gln
1               5                   10                  15

<210> SEQ ID NO 57
<211> LENGTH: 14
<212> TYPE: PRT
<213> ORGANISM: Artificial Sequence
<220> FEATURE:
<223> OTHER INFORMATION: based on Apis mellifera

<400> SEQUENCE: 57

Thr Gly Leu Ala Ala Leu Ile Ser Trp Ile Lys Arg Lys Arg
1               5                   10

<210> SEQ ID NO 58
<211> LENGTH: 15
<212> TYPE: PRT
<213> ORGANISM: Artificial Sequence
<220> FEATURE:
<223> OTHER INFORMATION: based on Apis mellifera
```

-continued

<210> SEQ ID NO 58
<400> SEQUENCE: 58

Gly Leu Ala Ala Leu Ile Ser Trp Ile Lys Arg Lys Arg Gln Gln
1               5                   10                  15

<210> SEQ ID NO 59
<211> LENGTH: 14
<212> TYPE: PRT
<213> ORGANISM: Artificial Sequence
<220> FEATURE:
<223> OTHER INFORMATION: based on Apis mellifera

<400> SEQUENCE: 59

Gly Leu Ala Ala Leu Ile Ser Trp Ile Lys Arg Lys Arg Gln
1               5                   10

<210> SEQ ID NO 60
<211> LENGTH: 13
<212> TYPE: PRT
<213> ORGANISM: Artificial Sequence
<220> FEATURE:
<223> OTHER INFORMATION: based on Apis mellifera

<400> SEQUENCE: 60

Gly Leu Ala Ala Leu Ile Ser Trp Ile Lys Arg Lys Arg
1               5                   10

<210> SEQ ID NO 61
<211> LENGTH: 14
<212> TYPE: PRT
<213> ORGANISM: Artificial Sequence
<220> FEATURE:
<223> OTHER INFORMATION: based on Apis mellifera

<400> SEQUENCE: 61

Leu Ala Ala Leu Ile Ser Trp Ile Lys Arg Lys Arg Gln Gln
1               5                   10

<210> SEQ ID NO 62
<211> LENGTH: 13
<212> TYPE: PRT
<213> ORGANISM: Artificial Sequence
<220> FEATURE:
<223> OTHER INFORMATION: based on Apis mellifera

<400> SEQUENCE: 62

Leu Ala Ala Leu Ile Ser Trp Ile Lys Arg Lys Arg Gln
1               5                   10

<210> SEQ ID NO 63
<211> LENGTH: 12
<212> TYPE: PRT
<213> ORGANISM: Artificial Sequence
<220> FEATURE:
<223> OTHER INFORMATION: based on Apis mellifera

<400> SEQUENCE: 63

Leu Ala Ala Leu Ile Ser Trp Ile Lys Arg Lys Arg
1               5                   10

<210> SEQ ID NO 64
<211> LENGTH: 13
<212> TYPE: PRT
<213> ORGANISM: Artificial Sequence
<220> FEATURE:
<223> OTHER INFORMATION: based on Apis mellifera

<400> SEQUENCE: 64

```
Ala Ala Leu Ile Ser Trp Ile Lys Arg Lys Arg Gln Gln
1               5                   10
```

<210> SEQ ID NO 65
<211> LENGTH: 12
<212> TYPE: PRT
<213> ORGANISM: Artificial Sequence
<220> FEATURE:
<223> OTHER INFORMATION: based on Apis mellifera

<400> SEQUENCE: 65

```
Ala Ala Leu Ile Ser Trp Ile Lys Arg Lys Arg Gln
1               5                   10
```

<210> SEQ ID NO 66
<211> LENGTH: 11
<212> TYPE: PRT
<213> ORGANISM: Artificial Sequence
<220> FEATURE:
<223> OTHER INFORMATION: based on Apis mellifera

<400> SEQUENCE: 66

```
Ala Ala Leu Ile Ser Trp Ile Lys Arg Lys Arg
1               5                   10
```

<210> SEQ ID NO 67
<211> LENGTH: 12
<212> TYPE: PRT
<213> ORGANISM: Artificial Sequence
<220> FEATURE:
<223> OTHER INFORMATION: based on Apis mellifera

<400> SEQUENCE: 67

```
Ala Leu Ile Ser Trp Ile Lys Arg Lys Arg Gln Gln
1               5                   10
```

<210> SEQ ID NO 68
<211> LENGTH: 11
<212> TYPE: PRT
<213> ORGANISM: Artificial Sequence
<220> FEATURE:
<223> OTHER INFORMATION: based on Apis mellifera

<400> SEQUENCE: 68

```
Ala Leu Ile Ser Trp Ile Lys Arg Lys Arg Gln
1               5                   10
```

<210> SEQ ID NO 69
<211> LENGTH: 10
<212> TYPE: PRT
<213> ORGANISM: Artificial Sequence
<220> FEATURE:
<223> OTHER INFORMATION: based on Apis mellifera

<400> SEQUENCE: 69

```
Ala Leu Ile Ser Trp Ile Lys Arg Lys Arg
1               5                   10
```

<210> SEQ ID NO 70
<211> LENGTH: 25
<212> TYPE: PRT
<213> ORGANISM: Artificial Sequence
<220> FEATURE:
<223> OTHER INFORMATION: based on Apis mellifera

<400> SEQUENCE: 70

```
Ile Gly Ala Val Leu Lys Val Leu Thr Thr Gly Leu Pro Ala Leu Ile
```

```
                1               5                  10                  15
Ser Trp Ile Lys Arg Lys Arg Gln Gln
            20                  25

<210> SEQ ID NO 71
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 71

Ile Gly Ala Val Leu Lys Val Leu Thr Thr Gly Leu Pro Ala Leu Ile
1               5                   10                  15

Ser Trp Ile Lys Arg Lys Arg Gln
            20

<210> SEQ ID NO 72
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 72

Ile Gly Ala Val Leu Lys Val Leu Thr Thr Gly Leu Pro Ala Leu Ile
1               5                   10                  15

Ser Trp Ile Lys Arg Lys Arg
            20

<210> SEQ ID NO 73
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 73

Gly Ala Val Leu Lys Val Leu Thr Thr Gly Leu Pro Ala Leu Ile Ser
1               5                   10                  15

Trp Ile Lys Arg Lys Arg Gln Gln
            20

<210> SEQ ID NO 74
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 74

Gly Ala Val Leu Lys Val Leu Thr Thr Gly Leu Pro Ala Leu Ile Ser
1               5                   10                  15

Trp Ile Lys Arg Lys Arg Gln
            20

<210> SEQ ID NO 75
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 75

Gly Ala Val Leu Lys Val Leu Thr Thr Gly Leu Pro Ala Leu Ile Ser
```

```
                1               5                  10                  15
Trp Ile Lys Arg Lys Arg
            20

<210> SEQ ID NO 76
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 76

Ala Val Leu Lys Val Leu Thr Thr Gly Leu Pro Ala Leu Ile Ser Trp
1               5                  10                  15

Ile Lys Arg Lys Arg Gln Gln
            20

<210> SEQ ID NO 77
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 77

Ala Val Leu Lys Val Leu Thr Thr Gly Leu Pro Ala Leu Ile Ser Trp
1               5                  10                  15

Ile Lys Arg Lys Arg Gln
            20

<210> SEQ ID NO 78
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 78

Ala Val Leu Lys Val Leu Thr Thr Gly Leu Pro Ala Leu Ile Ser Trp
1               5                  10                  15

Ile Lys Arg Lys Arg
            20

<210> SEQ ID NO 79
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 79

Val Leu Lys Val Leu Thr Thr Gly Leu Pro Ala Leu Ile Ser Trp Ile
1               5                  10                  15

Lys Arg Lys Arg Gln Gln
            20

<210> SEQ ID NO 80
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 80

Val Leu Lys Val Leu Thr Thr Gly Leu Pro Ala Leu Ile Ser Trp Ile
```

```
                1               5                  10                  15
Lys Arg Lys Arg Gln
                20

<210> SEQ ID NO 81
<211> LENGTH: 20
<212> TYPE: PRT
<213> ORGANISM: Artificial Sequence
<220> FEATURE:
<223> OTHER INFORMATION: based on Apis mellifera

<400> SEQUENCE: 81

Val Leu Lys Val Leu Thr Thr Gly Leu Pro Ala Leu Ile Ser Trp Ile
1               5                  10                  15

Lys Arg Lys Arg
                20

<210> SEQ ID NO 82
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 82

Leu Lys Val Leu Thr Thr Gly Leu Pro Ala Leu Ile Ser Trp Ile Lys
1               5                  10                  15

Arg Lys Arg Gln Gln
                20

<210> SEQ ID NO 83
<211> LENGTH: 20
<212> TYPE: PRT
<213> ORGANISM: Artificial Sequence
<220> FEATURE:
<223> OTHER INFORMATION: based on Apis mellifera

<400> SEQUENCE: 83

Leu Lys Val Leu Thr Thr Gly Leu Pro Ala Leu Ile Ser Trp Ile Lys
1               5                  10                  15

Arg Lys Arg Gln
                20

<210> SEQ ID NO 84
<211> LENGTH: 19
<212> TYPE: PRT
<213> ORGANISM: Artificial Sequence
<220> FEATURE:
<223> OTHER INFORMATION: based on Apis mellifera

<400> SEQUENCE: 84

Leu Lys Val Leu Thr Thr Gly Leu Pro Ala Leu Ile Ser Trp Ile Lys
1               5                  10                  15

Arg Lys Arg

<210> SEQ ID NO 85
<211> LENGTH: 20
<212> TYPE: PRT
<213> ORGANISM: Artificial Sequence
<220> FEATURE:
<223> OTHER INFORMATION: based on Apis mellifera

<400> SEQUENCE: 85

Lys Val Leu Thr Thr Gly Leu Pro Ala Leu Ile Ser Trp Ile Lys Arg
1               5                  10                  15
```

```
Lys Arg Gln Gln
            20

<210> SEQ ID NO 86
<211> LENGTH: 19
<212> TYPE: PRT
<213> ORGANISM: Artificial Sequence
<220> FEATURE:
<223> OTHER INFORMATION: based on Apis mellifera

<400> SEQUENCE: 86

Lys Val Leu Thr Thr Gly Leu Pro Ala Leu Ile Ser Trp Ile Lys Arg
1               5                   10                  15

Lys Arg Gln

<210> SEQ ID NO 87
<211> LENGTH: 18
<212> TYPE: PRT
<213> ORGANISM: Artificial Sequence
<220> FEATURE:
<223> OTHER INFORMATION: based on Apis mellifera

<400> SEQUENCE: 87

Lys Val Leu Thr Thr Gly Leu Pro Ala Leu Ile Ser Trp Ile Lys Arg
1               5                   10                  15

Lys Arg

<210> SEQ ID NO 88
<211> LENGTH: 19
<212> TYPE: PRT
<213> ORGANISM: Artificial Sequence
<220> FEATURE:
<223> OTHER INFORMATION: based on Apis mellifera

<400> SEQUENCE: 88

Val Leu Thr Thr Gly Leu Pro Ala Leu Ile Ser Trp Ile Lys Arg Lys
1               5                   10                  15

Arg Gln Gln

<210> SEQ ID NO 89
<211> LENGTH: 18
<212> TYPE: PRT
<213> ORGANISM: Artificial Sequence
<220> FEATURE:
<223> OTHER INFORMATION: based on Apis mellifera

<400> SEQUENCE: 89

Val Leu Thr Thr Gly Leu Pro Ala Leu Ile Ser Trp Ile Lys Arg Lys
1               5                   10                  15

Arg Gln

<210> SEQ ID NO 90
<211> LENGTH: 17
<212> TYPE: PRT
<213> ORGANISM: Artificial Sequence
<220> FEATURE:
<223> OTHER INFORMATION: based on Apis mellifera

<400> SEQUENCE: 90

Val Leu Thr Thr Gly Leu Pro Ala Leu Ile Ser Trp Ile Lys Arg Lys
1               5                   10                  15

Arg
```

```
<210> SEQ ID NO 91
<211> LENGTH: 18
<212> TYPE: PRT
<213> ORGANISM: Artificial Sequence
<220> FEATURE:
<223> OTHER INFORMATION: based on Apis mellifera

<400> SEQUENCE: 91

Leu Thr Thr Gly Leu Pro Ala Leu Ile Ser Trp Ile Lys Arg Lys Arg
1               5                   10                  15

Gln Gln

<210> SEQ ID NO 92
<211> LENGTH: 17
<212> TYPE: PRT
<213> ORGANISM: Artificial Sequence
<220> FEATURE:
<223> OTHER INFORMATION: based on Apis mellifera

<400> SEQUENCE: 92

Leu Thr Thr Gly Leu Pro Ala Leu Ile Ser Trp Ile Lys Arg Lys Arg
1               5                   10                  15

Gln

<210> SEQ ID NO 93
<211> LENGTH: 16
<212> TYPE: PRT
<213> ORGANISM: Artificial Sequence
<220> FEATURE:
<223> OTHER INFORMATION: based on Apis mellifera

<400> SEQUENCE: 93

Leu Thr Thr Gly Leu Pro Ala Leu Ile Ser Trp Ile Lys Arg Lys Arg
1               5                   10                  15

<210> SEQ ID NO 94
<211> LENGTH: 17
<212> TYPE: PRT
<213> ORGANISM: Artificial Sequence
<220> FEATURE:
<223> OTHER INFORMATION: based on Apis mellifera

<400> SEQUENCE: 94

Thr Thr Gly Leu Pro Ala Leu Ile Ser Trp Ile Lys Arg Lys Arg Gln
1               5                   10                  15

Gln

<210> SEQ ID NO 95
<211> LENGTH: 16
<212> TYPE: PRT
<213> ORGANISM: Artificial Sequence
<220> FEATURE:
<223> OTHER INFORMATION: based on Apis mellifera

<400> SEQUENCE: 95

Thr Thr Gly Leu Pro Ala Leu Ile Ser Trp Ile Lys Arg Lys Arg Gln
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: based on Apis mellifera

<400> SEQUENCE: 96
```

```
Thr Thr Gly Leu Pro Ala Leu Ile Ser Trp Ile Lys Arg Lys Arg
1               5                   10                  15
```

<210> SEQ ID NO 97
<211> LENGTH: 16
<212> TYPE: PRT
<213> ORGANISM: Artificial Sequence
<220> FEATURE:
<223> OTHER INFORMATION: based on Apis mellifera

<400> SEQUENCE: 97

```
Thr Gly Leu Pro Ala Leu Ile Ser Trp Ile Lys Arg Lys Arg Gln Gln
1               5                   10                  15
```

<210> SEQ ID NO 98
<211> LENGTH: 15
<212> TYPE: PRT
<213> ORGANISM: Artificial Sequence
<220> FEATURE:
<223> OTHER INFORMATION: based on Apis mellifera

<400> SEQUENCE: 98

```
Thr Gly Leu Pro Ala Leu Ile Ser Trp Ile Lys Arg Lys Arg Gln
1               5                   10                  15
```

<210> SEQ ID NO 99
<211> LENGTH: 14
<212> TYPE: PRT
<213> ORGANISM: Artificial Sequence
<220> FEATURE:
<223> OTHER INFORMATION: based on Apis mellifera

<400> SEQUENCE: 99

```
Thr Gly Leu Pro Ala Leu Ile Ser Trp Ile Lys Arg Lys Arg
1               5                   10
```

<210> SEQ ID NO 100
<211> LENGTH: 15
<212> TYPE: PRT
<213> ORGANISM: Artificial Sequence
<220> FEATURE:
<223> OTHER INFORMATION: based on Apis mellifera

<400> SEQUENCE: 100

```
Gly Leu Pro Ala Leu Ile Ser Trp Ile Lys Arg Lys Arg Gln Gln
1               5                   10                  15
```

<210> SEQ ID NO 101
<211> LENGTH: 14
<212> TYPE: PRT
<213> ORGANISM: Artificial Sequence
<220> FEATURE:
<223> OTHER INFORMATION: based on Apis mellifera

<400> SEQUENCE: 101

```
Gly Leu Pro Ala Leu Ile Ser Trp Ile Lys Arg Lys Arg Gln
1               5                   10
```

<210> SEQ ID NO 102
<211> LENGTH: 13
<212> TYPE: PRT
<213> ORGANISM: Artificial Sequence
<220> FEATURE:
<223> OTHER INFORMATION: based on Apis mellifera

<400> SEQUENCE: 102

```
Gly Leu Pro Ala Leu Ile Ser Trp Ile Lys Arg Lys Arg
1               5                   10
```

```
<210> SEQ ID NO 103
<211> LENGTH: 14
<212> TYPE: PRT
<213> ORGANISM: Artificial Sequence
<220> FEATURE:
<223> OTHER INFORMATION: based on Apis mellifera

<400> SEQUENCE: 103

Leu Pro Ala Leu Ile Ser Trp Ile Lys Arg Lys Arg Gln Gln
1               5                   10

<210> SEQ ID NO 104
<211> LENGTH: 13
<212> TYPE: PRT
<213> ORGANISM: Artificial Sequence
<220> FEATURE:
<223> OTHER INFORMATION: based on Apis mellifera

<400> SEQUENCE: 104

Leu Pro Ala Leu Ile Ser Trp Ile Lys Arg Lys Arg Gln
1               5                   10

<210> SEQ ID NO 105
<211> LENGTH: 12
<212> TYPE: PRT
<213> ORGANISM: Artificial Sequence
<220> FEATURE:
<223> OTHER INFORMATION: based on Apis mellifera

<400> SEQUENCE: 105

Leu Pro Ala Leu Ile Ser Trp Ile Lys Arg Lys Arg
1               5                   10

<210> SEQ ID NO 106
<211> LENGTH: 13
<212> TYPE: PRT
<213> ORGANISM: Artificial Sequence
<220> FEATURE:
<223> OTHER INFORMATION: based on Apis mellifera

<400> SEQUENCE: 106

Pro Ala Leu Ile Ser Trp Ile Lys Arg Lys Arg Gln Gln
1               5                   10

<210> SEQ ID NO 107
<211> LENGTH: 12
<212> TYPE: PRT
<213> ORGANISM: Artificial Sequence
<220> FEATURE:
<223> OTHER INFORMATION: based on Apis mellifera

<400> SEQUENCE: 107

Pro Ala Leu Ile Ser Trp Ile Lys Arg Lys Arg Gln
1               5                   10

<210> SEQ ID NO 108
<211> LENGTH: 11
<212> TYPE: PRT
<213> ORGANISM: Artificial Sequence
<220> FEATURE:
<223> OTHER INFORMATION: based on Apis mellifera

<400> SEQUENCE: 108

Pro Ala Leu Ile Ser Trp Ile Lys Arg Lys Arg
1               5                   10
```

```
<210> SEQ ID NO 109
<211> LENGTH: 25
<212> TYPE: PRT
<213> ORGANISM: Artificial Sequence
<220> FEATURE:
<223> OTHER INFORMATION: based on Apis mellifera

<400> SEQUENCE: 109

Gly Ile Gly Ala Val Leu Lys Val Leu Thr Thr Gly Leu Pro Ala Leu
1               5                   10                  15

Ile Ser Trp Ile Lys Arg Lys Arg Gln
            20                  25

<210> SEQ ID NO 110
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 110

Gly Ile Gly Ala Val Leu Lys Val Leu Thr Thr Gly Leu Pro Ala Leu
1               5                   10                  15

Ile Ser Trp Ile Lys Arg Lys Arg
            20

<210> SEQ ID NO 111
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 111

Gly Ile Gly Ala Val Leu Lys Val Leu Thr Thr Gly Leu Pro Ala Leu
1               5                   10                  15

Ile Ser Trp Ile Lys Arg Lys
            20

<210> SEQ ID NO 112
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 112

Gly Ile Gly Ala Val Leu Lys Val Leu Thr Thr Gly Leu Pro Ala Leu
1               5                   10                  15

Ile Ser Trp Ile Lys Arg
            20

<210> SEQ ID NO 113
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 113

Gly Ile Gly Ala Val Leu Lys Val Leu Thr Thr Gly Leu Pro Ala Leu
1               5                   10                  15

Ile Ser Trp Ile Lys
            20
```

-continued

<210> SEQ ID NO 114
<211> LENGTH: 26
<212> TYPE: PRT
<213> ORGANISM: Artificial Sequence
<220> FEATURE:
<223> OTHER INFORMATION: based on Apis mellifera

<400> SEQUENCE: 114

Gly Ile Gly Ala Trp Leu Lys Val Leu Thr Thr Gly Leu Pro Ala Trp
 1               5                   10                  15

Ile Ser Trp Ile Lys Arg Lys Arg Gln Gln
            20                  25

<210> SEQ ID NO 115
<211> LENGTH: 25
<212> TYPE: PRT
<213> ORGANISM: Artificial Sequence
<220> FEATURE:
<223> OTHER INFORMATION: based on Apis mellifera

<400> SEQUENCE: 115

Gly Ile Gly Ala Trp Leu Lys Val Leu Thr Thr Gly Leu Pro Ala Trp
 1               5                   10                  15

Ile Ser Trp Ile Lys Arg Lys Arg Gln
            20                  25

<210> SEQ ID NO 116
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 116

Gly Ile Gly Ala Trp Leu Lys Val Leu Thr Thr Gly Leu Pro Ala Trp
 1               5                   10                  15

Ile Ser Trp Ile Lys Arg Lys Arg
            20

<210> SEQ ID NO 117
<211> LENGTH: 25
<212> TYPE: PRT
<213> ORGANISM: Artificial Sequence
<220> FEATURE:
<223> OTHER INFORMATION: based on Apis mellifera

<400> SEQUENCE: 117

Ile Gly Ala Trp Leu Lys Val Leu Thr Thr Gly Leu Pro Ala Trp Ile
 1               5                   10                  15

Ser Trp Ile Lys Arg Lys Arg Gln Gln
            20                  25

<210> SEQ ID NO 118
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 118

Ile Gly Ala Trp Leu Lys Val Leu Thr Thr Gly Leu Pro Ala Trp Ile
 1               5                   10                  15

Ser Trp Ile Lys Arg Lys Arg Gln
            20

```
<210> SEQ ID NO 119
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 119

Ile Gly Ala Trp Leu Lys Val Leu Thr Thr Gly Leu Pro Ala Trp Ile
1               5                   10                  15

Ser Trp Ile Lys Arg Lys Arg
            20

<210> SEQ ID NO 120
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 120

Gly Ala Trp Leu Lys Val Leu Thr Thr Gly Leu Pro Ala Trp Ile Ser
1               5                   10                  15

Trp Ile Lys Arg Lys Arg Gln Gln
            20

<210> SEQ ID NO 121
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 121

Gly Ala Trp Leu Lys Val Leu Thr Thr Gly Leu Pro Ala Trp Ile Ser
1               5                   10                  15

Trp Ile Lys Arg Lys Arg Gln
            20

<210> SEQ ID NO 122
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 122

Gly Ala Trp Leu Lys Val Leu Thr Thr Gly Leu Pro Ala Trp Ile Ser
1               5                   10                  15

Trp Ile Lys Arg Lys Arg
            20

<210> SEQ ID NO 123
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 123

Ala Trp Leu Lys Val Leu Thr Thr Gly Leu Pro Ala Trp Ile Ser Trp
1               5                   10                  15

Ile Lys Arg Lys Arg Gln Gln
            20
```

```
<210> SEQ ID NO 124
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 124

Ala Trp Leu Lys Val Leu Thr Thr Gly Leu Pro Ala Trp Ile Ser Trp
1               5                   10                  15

Ile Lys Arg Lys Arg Gln
            20

<210> SEQ ID NO 125
<211> LENGTH: 21
<212> TYPE: PRT
<213> ORGANISM: Artificial Sequence
<220> FEATURE:
<223> OTHER INFORMATION: baed on Apis mellifera

<400> SEQUENCE: 125

Ala Trp Leu Lys Val Leu Thr Thr Gly Leu Pro Ala Trp Ile Ser Trp
1               5                   10                  15

Ile Lys Arg Lys Arg
            20

<210> SEQ ID NO 126
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 126

Trp Leu Lys Val Leu Thr Thr Gly Leu Pro Ala Trp Ile Ser Trp Ile
1               5                   10                  15

Lys Arg Lys Arg Gln Gln
            20

<210> SEQ ID NO 127
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 127

Trp Leu Lys Val Leu Thr Thr Gly Leu Pro Ala Trp Ile Ser Trp Ile
1               5                   10                  15

Lys Arg Lys Arg Gln
            20

<210> SEQ ID NO 128
<211> LENGTH: 20
<212> TYPE: PRT
<213> ORGANISM: Artificial Sequence
<220> FEATURE:
<223> OTHER INFORMATION: based on Apis mellifera

<400> SEQUENCE: 128

Trp Leu Lys Val Leu Thr Thr Gly Leu Pro Ala Trp Ile Ser Trp Ile
1               5                   10                  15

Lys Arg Lys Arg
            20
```

-continued

<210> SEQ ID NO 129
<211> LENGTH: 26
<212> TYPE: PRT
<213> ORGANISM: Artificial Sequence
<220> FEATURE:
<223> OTHER INFORMATION: based on Apis mellifera

<400> SEQUENCE: 129

Gly Ile Gly Ala Val Leu Lys Val Leu Thr Thr Gly Leu Ala Ala Trp
1               5                   10                  15

Ile Ser Trp Ile Lys Arg Lys Arg Gln Gln
            20                  25

<210> SEQ ID NO 130
<211> LENGTH: 25
<212> TYPE: PRT
<213> ORGANISM: Artificial Sequence
<220> FEATURE:
<223> OTHER INFORMATION: based on Apis mellifera

<400> SEQUENCE: 130

Gly Ile Gly Ala Val Leu Lys Val Leu Thr Thr Gly Leu Ala Ala Trp
1               5                   10                  15

Ile Ser Trp Ile Lys Arg Lys Arg Gln
            20                  25

<210> SEQ ID NO 131
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 131

Gly Ile Gly Ala Val Leu Lys Val Leu Thr Thr Gly Leu Ala Ala Trp
1               5                   10                  15

Ile Ser Trp Ile Lys Arg Lys Arg
            20

<210> SEQ ID NO 132
<211> LENGTH: 25
<212> TYPE: PRT
<213> ORGANISM: Artificial Sequence
<220> FEATURE:
<223> OTHER INFORMATION: based on Apis mellifera

<400> SEQUENCE: 132

Ile Gly Ala Val Leu Lys Val Leu Thr Thr Gly Leu Ala Ala Trp Ile
1               5                   10                  15

Ser Trp Ile Lys Arg Lys Arg Gln Gln
            20                  25

<210> SEQ ID NO 133
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 133

Ile Gly Ala Val Leu Lys Val Leu Thr Thr Gly Leu Ala Ala Trp Ile
1               5                   10                  15

Ser Trp Ile Lys Arg Lys Arg Gln
            20

```
<210> SEQ ID NO 134
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 134

Ile Gly Ala Val Leu Lys Val Leu Thr Thr Gly Leu Ala Ala Trp Ile
1               5                   10                  15

Ser Trp Ile Lys Arg Lys Arg
            20

<210> SEQ ID NO 135
<211> LENGTH: 24
<212> TYPE: PRT
<213> ORGANISM: Artificial Sequence
<220> FEATURE:
<223> OTHER INFORMATION: based Apis mellifera

<400> SEQUENCE: 135

Gly Ala Val Leu Lys Val Leu Thr Thr Gly Leu Ala Ala Trp Ile Ser
1               5                   10                  15

Trp Ile Lys Arg Lys Arg Gln Gln
            20

<210> SEQ ID NO 136
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 136

Gly Ala Val Leu Lys Val Leu Thr Thr Gly Leu Ala Ala Trp Ile Ser
1               5                   10                  15

Trp Ile Lys Arg Lys Arg Gln
            20

<210> SEQ ID NO 137
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 137

Gly Ala Val Leu Lys Val Leu Thr Thr Gly Leu Ala Ala Trp Ile Ser
1               5                   10                  15

Trp Ile Lys Arg Lys Arg
            20

<210> SEQ ID NO 138
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 138

Ala Val Leu Lys Val Leu Thr Thr Gly Leu Ala Ala Trp Ile Ser Trp
1               5                   10                  15

Ile Lys Arg Lys Arg Gln Gln
            20
```

```
<210> SEQ ID NO 139
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 139

Ala Val Leu Lys Val Leu Thr Thr Gly Leu Ala Ala Trp Ile Ser Trp
1               5                   10                  15

Ile Lys Arg Lys Arg Gln
            20

<210> SEQ ID NO 140
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 140

Ala Val Leu Lys Val Leu Thr Thr Gly Leu Ala Ala Trp Ile Ser Trp
1               5                   10                  15

Ile Lys Arg Lys Arg
            20

<210> SEQ ID NO 141
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 141

Val Leu Lys Val Leu Thr Thr Gly Leu Ala Ala Trp Ile Ser Trp Ile
1               5                   10                  15

Lys Arg Lys Arg Gln Gln
            20

<210> SEQ ID NO 142
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 142

Val Leu Lys Val Leu Thr Thr Gly Leu Ala Ala Trp Ile Ser Trp Ile
1               5                   10                  15

Lys Arg Lys Arg Gln
            20

<210> SEQ ID NO 143
<211> LENGTH: 20
<212> TYPE: PRT
<213> ORGANISM: Artificial Sequence
<220> FEATURE:
<223> OTHER INFORMATION: based on Apis mellifera

<400> SEQUENCE: 143

Val Leu Lys Val Leu Thr Thr Gly Leu Ala Ala Trp Ile Ser Trp Ile
1               5                   10                  15

Lys Arg Lys Arg
            20
```

```
<210> SEQ ID NO 144
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 144

Leu Lys Val Leu Thr Thr Gly Leu Ala Ala Trp Ile Ser Trp Ile Lys
1               5                   10                  15

Arg Lys Arg Gln Gln
            20

<210> SEQ ID NO 145
<211> LENGTH: 20
<212> TYPE: PRT
<213> ORGANISM: Artificial Sequence
<220> FEATURE:
<223> OTHER INFORMATION: based on Apis mellifera

<400> SEQUENCE: 145

Leu Lys Val Leu Thr Thr Gly Leu Ala Ala Trp Ile Ser Trp Ile Lys
1               5                   10                  15

Arg Lys Arg Gln
            20

<210> SEQ ID NO 146
<211> LENGTH: 19
<212> TYPE: PRT
<213> ORGANISM: Artificial Sequence
<220> FEATURE:
<223> OTHER INFORMATION: based on Apis mellifera

<400> SEQUENCE: 146

Leu Lys Val Leu Thr Thr Gly Leu Ala Ala Trp Ile Ser Trp Ile Lys
1               5                   10                  15

Arg Lys Arg

<210> SEQ ID NO 147
<211> LENGTH: 20
<212> TYPE: PRT
<213> ORGANISM: Artificial Sequence
<220> FEATURE:
<223> OTHER INFORMATION: based on Apis mellifera

<400> SEQUENCE: 147

Lys Val Leu Thr Thr Gly Leu Ala Ala Trp Ile Ser Trp Ile Lys Arg
1               5                   10                  15

Lys Arg Gln Gln
            20

<210> SEQ ID NO 148
<211> LENGTH: 19
<212> TYPE: PRT
<213> ORGANISM: Artificial Sequence
<220> FEATURE:
<223> OTHER INFORMATION: based on Apis mellifera

<400> SEQUENCE: 148

Lys Val Leu Thr Thr Gly Leu Ala Ala Trp Ile Ser Trp Ile Lys Arg
1               5                   10                  15

Lys Arg Gln

<210> SEQ ID NO 149
<211> LENGTH: 18
```

-continued

```
<212> TYPE: PRT
<213> ORGANISM: Artificial Sequence
<220> FEATURE:
<223> OTHER INFORMATION: based on Apis mellifera

<400> SEQUENCE: 149

Lys Val Leu Thr Thr Gly Leu Ala Ala Trp Ile Ser Trp Ile Lys Arg
1               5                   10                  15

Lys Arg

<210> SEQ ID NO 150
<211> LENGTH: 19
<212> TYPE: PRT
<213> ORGANISM: Artificial Sequence
<220> FEATURE:
<223> OTHER INFORMATION: based on Apis mellifera

<400> SEQUENCE: 150

Val Leu Thr Thr Gly Leu Ala Ala Trp Ile Ser Trp Ile Lys Arg Lys
1               5                   10                  15

Arg Gln Gln

<210> SEQ ID NO 151
<211> LENGTH: 18
<212> TYPE: PRT
<213> ORGANISM: Artificial Sequence
<220> FEATURE:
<223> OTHER INFORMATION: based on Apis mellifera

<400> SEQUENCE: 151

Val Leu Thr Thr Gly Leu Ala Ala Trp Ile Ser Trp Ile Lys Arg Lys
1               5                   10                  15

Arg Gln

<210> SEQ ID NO 152
<211> LENGTH: 17
<212> TYPE: PRT
<213> ORGANISM: Artificial Sequence
<220> FEATURE:
<223> OTHER INFORMATION: based on Apis mellifera

<400> SEQUENCE: 152

Val Leu Thr Thr Gly Leu Ala Ala Trp Ile Ser Trp Ile Lys Arg Lys
1               5                   10                  15

Arg

<210> SEQ ID NO 153
<211> LENGTH: 18
<212> TYPE: PRT
<213> ORGANISM: Artificial Sequence
<220> FEATURE:
<223> OTHER INFORMATION: based on Apis mellifera

<400> SEQUENCE: 153

Leu Thr Thr Gly Leu Ala Ala Trp Ile Ser Trp Ile Lys Arg Lys Arg
1               5                   10                  15

Gln Gln

<210> SEQ ID NO 154
<211> LENGTH: 17
<212> TYPE: PRT
<213> ORGANISM: Artificial Sequence
<220> FEATURE:
<223> OTHER INFORMATION: based on Apis mellifera
```

```
<400> SEQUENCE: 154

Leu Thr Thr Gly Leu Ala Ala Trp Ile Ser Trp Ile Lys Arg Lys Arg
1               5                   10                  15

Gln

<210> SEQ ID NO 155
<211> LENGTH: 16
<212> TYPE: PRT
<213> ORGANISM: Artificial Sequence
<220> FEATURE:
<223> OTHER INFORMATION: based on Apis mellifera

<400> SEQUENCE: 155

Leu Thr Thr Gly Leu Ala Ala Trp Ile Ser Trp Ile Lys Arg Lys Arg
1               5                   10                  15

<210> SEQ ID NO 156
<211> LENGTH: 17
<212> TYPE: PRT
<213> ORGANISM: Artificial Sequence
<220> FEATURE:
<223> OTHER INFORMATION: based on Apis mellifera

<400> SEQUENCE: 156

Thr Thr Gly Leu Ala Ala Trp Ile Ser Trp Ile Lys Arg Lys Arg Gln
1               5                   10                  15

Gln

<210> SEQ ID NO 157
<211> LENGTH: 16
<212> TYPE: PRT
<213> ORGANISM: Artificial Sequence
<220> FEATURE:
<223> OTHER INFORMATION: based on Apis mellifera

<400> SEQUENCE: 157

Thr Thr Gly Leu Ala Ala Trp Ile Ser Trp Ile Lys Arg Lys Arg Gln
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: based on Apis mellifera

<400> SEQUENCE: 158

Thr Thr Gly Leu Ala Ala Trp Ile Ser Trp Ile Lys Arg Lys Arg
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: based on Apis mellifera

<400> SEQUENCE: 159

Thr Gly Leu Ala Ala Trp Ile Ser Trp Ile Lys Arg Lys Arg Gln Gln
1               5                   10                  15

<210> SEQ ID NO 160
<211> LENGTH: 15
<212> TYPE: PRT
<213> ORGANISM: Artificial Sequence
<220> FEATURE:
```

<223> OTHER INFORMATION: based on Apis mellifera

<400> SEQUENCE: 160

Thr Gly Leu Ala Ala Trp Ile Ser Trp Ile Lys Arg Lys Arg Gln
1               5                   10                  15

<210> SEQ ID NO 161
<211> LENGTH: 14
<212> TYPE: PRT
<213> ORGANISM: Artificial Sequence
<220> FEATURE:
<223> OTHER INFORMATION: based on Apis mellifera

<400> SEQUENCE: 161

Thr Gly Leu Ala Ala Trp Ile Ser Trp Ile Lys Arg Lys Arg
1               5                   10

<210> SEQ ID NO 162
<211> LENGTH: 15
<212> TYPE: PRT
<213> ORGANISM: Artificial Sequence
<220> FEATURE:
<223> OTHER INFORMATION: based on Apis mellifera

<400> SEQUENCE: 162

Gly Leu Ala Ala Trp Ile Ser Trp Ile Lys Arg Lys Arg Gln Gln
1               5                   10                  15

<210> SEQ ID NO 163
<211> LENGTH: 14
<212> TYPE: PRT
<213> ORGANISM: Artificial Sequence
<220> FEATURE:
<223> OTHER INFORMATION: based on Apis mellifera

<400> SEQUENCE: 163

Gly Leu Ala Ala Trp Ile Ser Trp Ile Lys Arg Lys Arg Gln
1               5                   10

<210> SEQ ID NO 164
<211> LENGTH: 13
<212> TYPE: PRT
<213> ORGANISM: Artificial Sequence
<220> FEATURE:
<223> OTHER INFORMATION: based on Apis mellifera

<400> SEQUENCE: 164

Gly Leu Ala Ala Trp Ile Ser Trp Ile Lys Arg Lys Arg
1               5                   10

<210> SEQ ID NO 165
<211> LENGTH: 14
<212> TYPE: PRT
<213> ORGANISM: Artificial Sequence
<220> FEATURE:
<223> OTHER INFORMATION: based on Apis mellifera

<400> SEQUENCE: 165

Leu Ala Ala Trp Ile Ser Trp Ile Lys Arg Lys Arg Gln Gln
1               5                   10

<210> SEQ ID NO 166
<211> LENGTH: 13
<212> TYPE: PRT
<213> ORGANISM: Artificial Sequence
<220> FEATURE:
<223> OTHER INFORMATION: based on Apis mellifera

```
<400> SEQUENCE: 166

Leu Ala Ala Trp Ile Ser Trp Ile Lys Arg Lys Arg Gln
1               5                   10

<210> SEQ ID NO 167
<211> LENGTH: 12
<212> TYPE: PRT
<213> ORGANISM: Artificial Sequence
<220> FEATURE:
<223> OTHER INFORMATION: based on Apis mellifera

<400> SEQUENCE: 167

Leu Ala Ala Trp Ile Ser Trp Ile Lys Arg Lys Arg
1               5                   10

<210> SEQ ID NO 168
<211> LENGTH: 13
<212> TYPE: PRT
<213> ORGANISM: Artificial Sequence
<220> FEATURE:
<223> OTHER INFORMATION: base don Apis mellifera

<400> SEQUENCE: 168

Ala Ala Trp Ile Ser Trp Ile Lys Arg Lys Arg Gln Gln
1               5                   10

<210> SEQ ID NO 169
<211> LENGTH: 12
<212> TYPE: PRT
<213> ORGANISM: Artificial Sequence
<220> FEATURE:
<223> OTHER INFORMATION: based on Apis mellifera

<400> SEQUENCE: 169

Ala Ala Trp Ile Ser Trp Ile Lys Arg Lys Arg Gln
1               5                   10

<210> SEQ ID NO 170
<211> LENGTH: 11
<212> TYPE: PRT
<213> ORGANISM: Artificial Sequence
<220> FEATURE:
<223> OTHER INFORMATION: based on Apis mellifera

<400> SEQUENCE: 170

Ala Ala Trp Ile Ser Trp Ile Lys Arg Lys Arg
1               5                   10

<210> SEQ ID NO 171
<211> LENGTH: 12
<212> TYPE: PRT
<213> ORGANISM: Artificial Sequence
<220> FEATURE:
<223> OTHER INFORMATION: based on Apis mellifera

<400> SEQUENCE: 171

Ala Trp Ile Ser Trp Ile Lys Arg Lys Arg Gln Gln
1               5                   10

<210> SEQ ID NO 172
<211> LENGTH: 11
<212> TYPE: PRT
<213> ORGANISM: Artificial Sequence
<220> FEATURE:
<223> OTHER INFORMATION: based on Apis mellifera

<400> SEQUENCE: 172
```

```
Ala Trp Ile Ser Trp Ile Lys Arg Lys Arg Gln
1               5                   10

<210> SEQ ID NO 173
<211> LENGTH: 10
<212> TYPE: PRT
<213> ORGANISM: Artificial Sequence
<220> FEATURE:
<223> OTHER INFORMATION: based on Apis mellifera

<400> SEQUENCE: 173

Ala Trp Ile Ser Trp Ile Lys Arg Lys Arg
1               5                   10

<210> SEQ ID NO 174
<211> LENGTH: 25
<212> TYPE: PRT
<213> ORGANISM: Artificial Sequence
<220> FEATURE:
<223> OTHER INFORMATION: based on Apis mellifera

<400> SEQUENCE: 174

Ile Gly Ala Val Leu Lys Val Leu Thr Thr Gly Leu Pro Ala Trp Ile
1               5                   10                  15

Ser Trp Ile Lys Arg Lys Arg Gln Gln
            20                  25

<210> SEQ ID NO 175
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 175

Ile Gly Ala Val Leu Lys Val Leu Thr Thr Gly Leu Pro Ala Trp Ile
1               5                   10                  15

Ser Trp Ile Lys Arg Lys Arg Gln
            20

<210> SEQ ID NO 176
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 176

Ile Gly Ala Val Leu Lys Val Leu Thr Thr Gly Leu Pro Ala Trp Ile
1               5                   10                  15

Ser Trp Ile Lys Arg Lys Arg
            20

<210> SEQ ID NO 177
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 177

Gly Ala Val Leu Lys Val Leu Thr Thr Gly Leu Pro Ala Trp Ile Ser
1               5                   10                  15

Trp Ile Lys Arg Lys Arg Gln Gln
            20
```

-continued

<210> SEQ ID NO 178
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 178

Gly Ala Val Leu Lys Val Leu Thr Thr Gly Leu Pro Ala Trp Ile Ser
1               5                   10                  15

Trp Ile Lys Arg Lys Arg Gln
            20

<210> SEQ ID NO 179
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 179

Gly Ala Val Leu Lys Val Leu Thr Thr Gly Leu Pro Ala Trp Ile Ser
1               5                   10                  15

Trp Ile Lys Arg Lys Arg
            20

<210> SEQ ID NO 180
<211> LENGTH: 23
<212> TYPE: PRT
<213> ORGANISM: Artificial Sequence
<220> FEATURE:
<223> OTHER INFORMATION: based on Apis mellifera

<400> SEQUENCE: 180

Ala Val Leu Lys Val Leu Thr Thr Gly Leu Pro Ala Trp Ile Ser Trp
1               5                   10                  15

Ile Lys Arg Lys Arg Gln Gln
            20

<210> SEQ ID NO 181
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 181

Ala Val Leu Lys Val Leu Thr Thr Gly Leu Pro Ala Trp Ile Ser Trp
1               5                   10                  15

Ile Lys Arg Lys Arg Gln
            20

<210> SEQ ID NO 182
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 182

Ala Val Leu Lys Val Leu Thr Thr Gly Leu Pro Ala Trp Ile Ser Trp
1               5                   10                  15

Ile Lys Arg Lys Arg
            20

```
<210> SEQ ID NO 183
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 183

Val Leu Lys Val Leu Thr Thr Gly Leu Pro Ala Trp Ile Ser Trp Ile
1               5                   10                  15

Lys Arg Lys Arg Gln Gln
            20

<210> SEQ ID NO 184
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 184

Val Leu Lys Val Leu Thr Thr Gly Leu Pro Ala Trp Ile Ser Trp Ile
1               5                   10                  15

Lys Arg Lys Arg Gln
            20

<210> SEQ ID NO 185
<211> LENGTH: 20
<212> TYPE: PRT
<213> ORGANISM: Artificial Sequence
<220> FEATURE:
<223> OTHER INFORMATION: basd on Apis mellifera

<400> SEQUENCE: 185

Val Leu Lys Val Leu Thr Thr Gly Leu Pro Ala Trp Ile Ser Trp Ile
1               5                   10                  15

Lys Arg Lys Arg
            20

<210> SEQ ID NO 186
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 186

Leu Lys Val Leu Thr Thr Gly Leu Pro Ala Trp Ile Ser Trp Ile Lys
1               5                   10                  15

Arg Lys Arg Gln Gln
            20

<210> SEQ ID NO 187
<211> LENGTH: 20
<212> TYPE: PRT
<213> ORGANISM: Artificial Sequence
<220> FEATURE:
<223> OTHER INFORMATION: based on Apis mellifera

<400> SEQUENCE: 187

Leu Lys Val Leu Thr Thr Gly Leu Pro Ala Trp Ile Ser Trp Ile Lys
1               5                   10                  15

Arg Lys Arg Gln
            20
```

```
<210> SEQ ID NO 188
<211> LENGTH: 19
<212> TYPE: PRT
<213> ORGANISM: Artificial Sequence
<220> FEATURE:
<223> OTHER INFORMATION: based on Apis mellifera

<400> SEQUENCE: 188

Leu Lys Val Leu Thr Thr Gly Leu Pro Ala Trp Ile Ser Trp Ile Lys
 1               5                  10                  15

Arg Lys Arg

<210> SEQ ID NO 189
<211> LENGTH: 20
<212> TYPE: PRT
<213> ORGANISM: Artificial Sequence
<220> FEATURE:
<223> OTHER INFORMATION: based on Apis mellifera

<400> SEQUENCE: 189

Lys Val Leu Thr Thr Gly Leu Pro Ala Trp Ile Ser Trp Ile Lys Arg
 1               5                  10                  15

Lys Arg Gln Gln
            20

<210> SEQ ID NO 190
<211> LENGTH: 19
<212> TYPE: PRT
<213> ORGANISM: Artificial Sequence
<220> FEATURE:
<223> OTHER INFORMATION: based on Apis mellifera

<400> SEQUENCE: 190

Lys Val Leu Thr Thr Gly Leu Pro Ala Trp Ile Ser Trp Ile Lys Arg
 1               5                  10                  15

Lys Arg Gln

<210> SEQ ID NO 191
<211> LENGTH: 18
<212> TYPE: PRT
<213> ORGANISM: Artificial Sequence
<220> FEATURE:
<223> OTHER INFORMATION: based on Apis mellifera

<400> SEQUENCE: 191

Lys Val Leu Thr Thr Gly Leu Pro Ala Trp Ile Ser Trp Ile Lys Arg
 1               5                  10                  15

Lys Arg

<210> SEQ ID NO 192
<211> LENGTH: 19
<212> TYPE: PRT
<213> ORGANISM: Artificial Sequence
<220> FEATURE:
<223> OTHER INFORMATION: based on Apis mellifera

<400> SEQUENCE: 192

Val Leu Thr Thr Gly Leu Pro Ala Trp Ile Ser Trp Ile Lys Arg Lys
 1               5                  10                  15

Arg Gln Gln

<210> SEQ ID NO 193
<211> LENGTH: 18
<212> TYPE: PRT
```

```
<213> ORGANISM: Artificial Sequence
<220> FEATURE:
<223> OTHER INFORMATION: based on Apis mellifera

<400> SEQUENCE: 193

Val Leu Thr Thr Gly Leu Pro Ala Trp Ile Ser Trp Ile Lys Arg Lys
1               5                   10                  15

Arg Gln

<210> SEQ ID NO 194
<211> LENGTH: 17
<212> TYPE: PRT
<213> ORGANISM: Artificial Sequence
<220> FEATURE:
<223> OTHER INFORMATION: based on Apis mellifera

<400> SEQUENCE: 194

Val Leu Thr Thr Gly Leu Pro Ala Trp Ile Ser Trp Ile Lys Arg Lys
1               5                   10                  15

Arg

<210> SEQ ID NO 195
<211> LENGTH: 18
<212> TYPE: PRT
<213> ORGANISM: Artificial Sequence
<220> FEATURE:
<223> OTHER INFORMATION: based on Apis mellifera

<400> SEQUENCE: 195

Leu Thr Thr Gly Leu Pro Ala Trp Ile Ser Trp Ile Lys Arg Lys Arg
1               5                   10                  15

Gln Gln

<210> SEQ ID NO 196
<211> LENGTH: 17
<212> TYPE: PRT
<213> ORGANISM: Artificial Sequence
<220> FEATURE:
<223> OTHER INFORMATION: based on Apis mellifera

<400> SEQUENCE: 196

Leu Thr Thr Gly Leu Pro Ala Trp Ile Ser Trp Ile Lys Arg Lys Arg
1               5                   10                  15

Gln

<210> SEQ ID NO 197
<211> LENGTH: 16
<212> TYPE: PRT
<213> ORGANISM: Artificial Sequence
<220> FEATURE:
<223> OTHER INFORMATION: based on Apis mellifera

<400> SEQUENCE: 197

Leu Thr Thr Gly Leu Pro Ala Trp Ile Ser Trp Ile Lys Arg Lys Arg
1               5                   10                  15

<210> SEQ ID NO 198
<211> LENGTH: 17
<212> TYPE: PRT
<213> ORGANISM: Artificial Sequence
<220> FEATURE:
<223> OTHER INFORMATION: based on Apis mellifera

<400> SEQUENCE: 198

Thr Thr Gly Leu Pro Ala Trp Ile Ser Trp Ile Lys Arg Lys Arg Gln
```

```
                  1               5                  10                  15
Gln

<210> SEQ ID NO 199
<211> LENGTH: 16
<212> TYPE: PRT
<213> ORGANISM: Artificial Sequence
<220> FEATURE:
<223> OTHER INFORMATION: based on Apis mellifera

<400> SEQUENCE: 199

Thr Thr Gly Leu Pro Ala Trp Ile Ser Trp Ile Lys Arg Lys Arg Gln
  1               5                  10                  15

<210> SEQ ID NO 200
<211> LENGTH: 15
<212> TYPE: PRT
<213> ORGANISM: Artificial Sequence
<220> FEATURE:
<223> OTHER INFORMATION: based on Apis mellifera

<400> SEQUENCE: 200

Thr Thr Gly Leu Pro Ala Trp Ile Ser Trp Ile Lys Arg Lys Arg
  1               5                  10                  15

<210> SEQ ID NO 201
<211> LENGTH: 16
<212> TYPE: PRT
<213> ORGANISM: Artificial Sequence
<220> FEATURE:
<223> OTHER INFORMATION: based on Apis mellifera

<400> SEQUENCE: 201

Thr Gly Leu Pro Ala Trp Ile Ser Trp Ile Lys Arg Lys Arg Gln Gln
  1               5                  10                  15

<210> SEQ ID NO 202
<211> LENGTH: 15
<212> TYPE: PRT
<213> ORGANISM: Artificial Sequence
<220> FEATURE:
<223> OTHER INFORMATION: based on Apis mellifera

<400> SEQUENCE: 202

Thr Gly Leu Pro Ala Trp Ile Ser Trp Ile Lys Arg Lys Arg Gln
  1               5                  10                  15

<210> SEQ ID NO 203
<211> LENGTH: 14
<212> TYPE: PRT
<213> ORGANISM: Artificial Sequence
<220> FEATURE:
<223> OTHER INFORMATION: based on Apis mellifera

<400> SEQUENCE: 203

Thr Gly Leu Pro Ala Trp Ile Ser Trp Ile Lys Arg Lys Arg
  1               5                  10

<210> SEQ ID NO 204
<211> LENGTH: 15
<212> TYPE: PRT
<213> ORGANISM: Artificial Sequence
<220> FEATURE:
<223> OTHER INFORMATION: based on Apis mellifera

<400> SEQUENCE: 204

Gly Leu Pro Ala Trp Ile Ser Trp Ile Lys Arg Lys Arg Gln Gln
```

<210> SEQ ID NO 205
<211> LENGTH: 14
<212> TYPE: PRT
<213> ORGANISM: Artificial Sequence
<220> FEATURE:
<223> OTHER INFORMATION: based on Apis mellifera

<400> SEQUENCE: 205

Gly Leu Pro Ala Trp Ile Ser Trp Ile Lys Arg Lys Arg Gln
1               5                   10

<210> SEQ ID NO 206
<211> LENGTH: 13
<212> TYPE: PRT
<213> ORGANISM: Artificial Sequence
<220> FEATURE:
<223> OTHER INFORMATION: based on Apis mellifera

<400> SEQUENCE: 206

Gly Leu Pro Ala Trp Ile Ser Trp Ile Lys Arg Lys Arg
1               5                   10

<210> SEQ ID NO 207
<211> LENGTH: 14
<212> TYPE: PRT
<213> ORGANISM: Artificial Sequence
<220> FEATURE:
<223> OTHER INFORMATION: based on Apis mellifera

<400> SEQUENCE: 207

Leu Pro Ala Trp Ile Ser Trp Ile Lys Arg Lys Arg Gln Gln
1               5                   10

<210> SEQ ID NO 208
<211> LENGTH: 13
<212> TYPE: PRT
<213> ORGANISM: Artificial Sequence
<220> FEATURE:
<223> OTHER INFORMATION: based on Apis mellifera

<400> SEQUENCE: 208

Leu Pro Ala Trp Ile Ser Trp Ile Lys Arg Lys Arg Gln
1               5                   10

<210> SEQ ID NO 209
<211> LENGTH: 12
<212> TYPE: PRT
<213> ORGANISM: Artificial Sequence
<220> FEATURE:
<223> OTHER INFORMATION: based on Apis mellifera

<400> SEQUENCE: 209

Leu Pro Ala Trp Ile Ser Trp Ile Lys Arg Lys Arg
1               5                   10

<210> SEQ ID NO 210
<211> LENGTH: 13
<212> TYPE: PRT
<213> ORGANISM: Artificial Sequence
<220> FEATURE:
<223> OTHER INFORMATION: based on Apis mellifera

<400> SEQUENCE: 210

Pro Ala Trp Ile Ser Trp Ile Lys Arg Lys Arg Gln Gln
1               5                   10

```
<210> SEQ ID NO 211
<211> LENGTH: 12
<212> TYPE: PRT
<213> ORGANISM: Artificial Sequence
<220> FEATURE:
<223> OTHER INFORMATION: based on Apis mellifera

<400> SEQUENCE: 211

Pro Ala Trp Ile Ser Trp Ile Lys Arg Lys Arg Gln
1               5                   10

<210> SEQ ID NO 212
<211> LENGTH: 11
<212> TYPE: PRT
<213> ORGANISM: Artificial Sequence
<220> FEATURE:
<223> OTHER INFORMATION: based on Apis mellifera

<400> SEQUENCE: 212

Pro Ala Trp Ile Ser Trp Ile Lys Arg Lys Arg
1               5                   10

<210> SEQ ID NO 213
<211> LENGTH: 26
<212> TYPE: PRT
<213> ORGANISM: Artificial Sequence
<220> FEATURE:
<223> OTHER INFORMATION: based on Apis mellifera

<400> SEQUENCE: 213

Gly Ile Gly Ala Val Leu Lys Val Leu Thr Thr Gly Leu Pro Ala Trp
1               5                   10                  15

Ile Ser Trp Ile Lys Arg Lys Arg Gln Gln
            20                  25

<210> SEQ ID NO 214
<211> LENGTH: 25
<212> TYPE: PRT
<213> ORGANISM: Artificial Sequence
<220> FEATURE:
<223> OTHER INFORMATION: based on Apis mellifera

<400> SEQUENCE: 214

Gly Ile Gly Ala Val Leu Lys Val Leu Thr Thr Gly Leu Pro Ala Trp
1               5                   10                  15

Ile Ser Trp Ile Lys Arg Lys Arg Gln
            20                  25

<210> SEQ ID NO 215
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 215

Gly Ile Gly Ala Val Leu Lys Val Leu Thr Thr Gly Leu Pro Ala Trp
1               5                   10                  15

Ile Ser Trp Ile Lys Arg Lys Arg
            20

<210> SEQ ID NO 216
<211> LENGTH: 23
<212> TYPE: PRT
<213> ORGANISM: Artificial Sequence
<220> FEATURE:
```

<223> OTHER INFORMATION: based on Apis mellifera

<400> SEQUENCE: 216

Gly Ile Gly Ala Val Leu Lys Val Leu Thr Thr Gly Leu Pro Ala Trp
1               5                   10                  15

Ile Ser Trp Ile Lys Arg Lys
            20

<210> SEQ ID NO 217
<211> LENGTH: 22
<212> TYPE: PRT
<213> ORGANISM: Artificial Sequence
<220> FEATURE:
<223> OTHER INFORMATION: based on Apis mellifera

<400> SEQUENCE: 217

Gly Ile Gly Ala Val Leu Lys Val Leu Thr Thr Gly Leu Pro Ala Trp
1               5                   10                  15

Ile Ser Trp Ile Lys Arg
            20

<210> SEQ ID NO 218
<211> LENGTH: 21
<212> TYPE: PRT
<213> ORGANISM: Artificial Sequence
<220> FEATURE:
<223> OTHER INFORMATION: based on Apis mellifera

<400> SEQUENCE: 218

Gly Ile Gly Ala Val Leu Lys Val Leu Thr Thr Gly Leu Pro Ala Trp
1               5                   10                  15

Ile Ser Trp Ile Lys
            20

<210> SEQ ID NO 219
<211> LENGTH: 26
<212> TYPE: PRT
<213> ORGANISM: Artificial Sequence
<220> FEATURE:
<223> OTHER INFORMATION: based on Apis mellifera

<400> SEQUENCE: 219

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 220
<211> LENGTH: 37
<212> TYPE: PRT
<213> ORGANISM: Artificial Sequence
<220> FEATURE:
<223> OTHER INFORMATION: based on Apis mellifera

<400> SEQUENCE: 220

Gly Ile Gly Ala Val Leu Lys Val Leu Thr Thr Gly Leu Pro Ala Leu
1               5                   10                  15

Ile Ser Trp Ile Lys Arg Lys Arg Gln Gln Thr Ala Leu Asp Trp Ser
            20                  25                  30

Trp Leu Gln Thr Glu
        35

<210> SEQ ID NO 221
<211> LENGTH: 37

```
<212> TYPE: PRT
<213> ORGANISM: Artificial Sequence
<220> FEATURE:
<223> OTHER INFORMATION: based on Apis mellifera

<400> SEQUENCE: 221

Thr Ala Leu Asp Trp Ser Trp Leu Gln Thr Glu Gly Ile Gly Ala Val
1               5                   10                  15

Leu Lys Val Leu Thr Thr Gly Leu Pro Ala Leu Ile Ser Trp Ile Lys
            20                  25                  30

Arg Lys Arg Gln Gln
        35

<210> SEQ ID NO 222
<211> LENGTH: 7
<212> TYPE: PRT
<213> ORGANISM: Artificial Sequence
<220> FEATURE:
<223> OTHER INFORMATION: based on Apis mellifera

<400> SEQUENCE: 222

Val His Pro Lys Gln His Arg
1               5

<210> SEQ ID NO 223
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 223

Val Leu Thr Thr Gly Leu Pro Ala Leu Ile Ser Trp Ile Lys Arg Gly
1               5                   10                  15

Gly Val His Pro Lys Gln His Arg
            20

<210> SEQ ID NO 224
<211> LENGTH: 24
<212> TYPE: PRT
<213> ORGANISM: Artificial Sequence
<220> FEATURE:
<223> OTHER INFORMATION: based on Apis mellifera

<400> SEQUENCE: 224

Val His Pro Lys Gln His Arg Gly Gly Val Leu Thr Thr Gly Leu Pro
1               5                   10                  15

Ala Leu Ile Ser Trp Ile Lys Arg
            20

<210> SEQ ID NO 225
<211> LENGTH: 32
<212> TYPE: PRT
<213> ORGANISM: Artificial Sequence
<220> FEATURE:
<223> OTHER INFORMATION: SYNTHESIZED

<400> SEQUENCE: 225

Thr Ala Leu Asp Trp Ser Trp Leu Gln Thr Glu Gly Gly Val Leu Thr
1               5                   10                  15

Thr Gly Leu Pro Ala Leu Ile Ser Trp Ile Lys Arg Lys Arg Gln Gln
            20                  25                  30
```

UNIVERSAL ANCHOR PEPTIDE FOR NANOPARTICLES

CROSS REFERENCE TO RELATED APPLICATIONS

This application claims the priority of PCT/US2009/041000, filed Apr. 17, 2009, which claims the priority of U.S. provisional application No. 61/047,013, filed Apr. 22, 2008, each of which is hereby incorporated by reference in its entirety.

GOVERNMENTAL RIGHTS

This invention was made with government support under grant number U54CA119342 awarded by the National Cancer Center and HL073646 awarded by the National Heart Lung and Blood Institute. The government has certain rights in the invention.

FIELD OF THE INVENTION

The present invention generally relates to a universal anchor peptide that is capable of stably inserting into lipid membranes. In particular, the anchor peptide is a cationic amphipathic alpha helical peptide that is capable of integrating into lipid membranes of nanoparticle or cells. Moreover, the anchor peptide may be conjugated to a variety of different cargo complexes.

BACKGROUND OF THE INVENTION

One of the vexing problems with targeted delivery of chemotherapeutic agents or other forms of therapy with the use of nanoparticle carriers is how to associate these agents with specific cells to achieve selective molecular imaging or site targeted drug therapy. This requires the incorporation of a targeting ligand that can bind to a specific molecular epitope on the cell surface, which subsequently allows detection of particle binding by imaging methods, or drug delivery to the cell of choice. Generally, this targeting ligand is formulated into the nanoparticle by a chemical reaction or by physical association, in a process that is integral to the very construction of the nanoparticle itself such that at the end of the process, a singular and highly specific targeting delivery system is produced. In order to produce an alternatively targeted delivery system, the entire formulation process must be recapitulated for another targeting ligand, typically requiring new design strategies for ligand association that could change the formulation process dramatically and affect its performance as a targeted delivery system. Consequently, there is a need in the art for a universal anchor peptide that would allow the pre-formed construction of carrier systems, and then later allow their flexible association with a particular ligand for targeting, therapeutic, reporting, or imaging purposes.

SUMMARY OF THE INVENTION

Among the various aspects of the present invention is the provision of a nanoparticle comprising an anchor peptide that is substantially non-lytic and non-cytotoxic. The nanoparticle comprises a core encapsulated by a lipid layer, wherein the anchor peptide is stably inserted into the lipid layer.

Another aspect of the present invention encompasses a kit for preparing a nanoparticle comprising an anchor peptide. The kit comprises a first composition comprising a nanoparticle that comprises a core encapsulated by a lipid layer. The kit also comprises a second composition comprising the anchor peptide that is substantially non-lytic, non-cytotoxic, and is capable of stably inserting into the lipid layer of the nanoparticle.

A further aspect of the present invention provides a method for adding a cargo complex to a nanoparticle. The method comprises contacting the nanoparticle comprising a lipid layer with an substantially non-lytic, non-cytotoxic anchor peptide that is conjugated to the cargo complex, wherein the anchor peptide stably inserts into the lipid layer of the nanoparticle.

Yet another aspect of the invention encompasses an anchor peptide. The anchor peptide is cationic, comprises at least one amphipathic alpha helix, and is substantially non-lytic and non-cytotoxic.

Other aspects and features of the invention are detailed below.

DETAILED DESCRIPTION OF THE INVENTION

Figure 1:
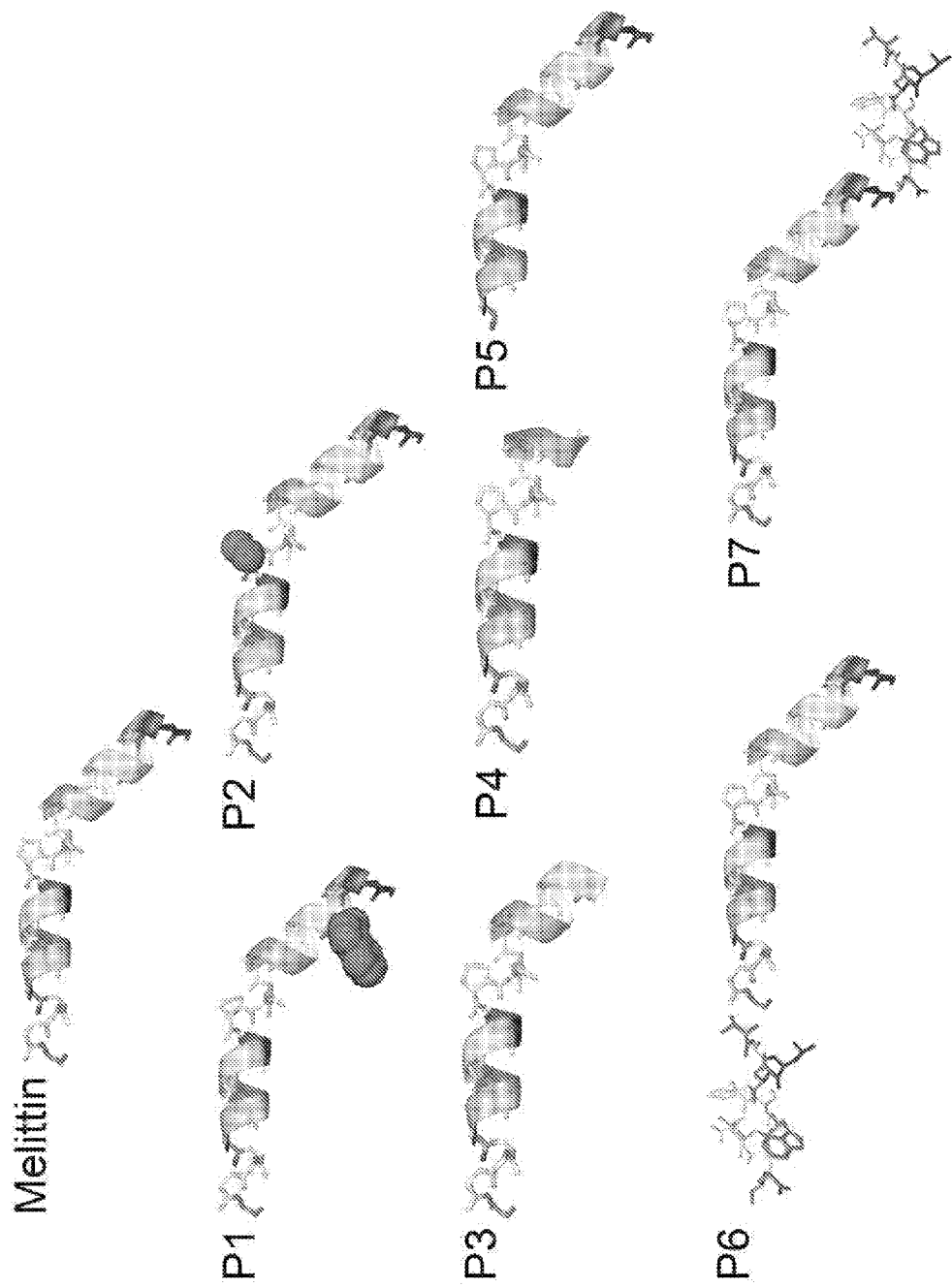
FIG. 1 depicts structures of melittin (2mlt) and seven derivatives of melittin (P1 to P7). PDB file of 2mlt was downloaded from protein data bank, and B chain of the 2mlt was used for presenting the structures of melittin and the seven derivatives by PyMOL. The structures are presented with the C-terminal on the left and the N-terminal on the right. P1 had the 5th amino acid valine substituted by tryptophan, which is depicted in a space filling view. P2 had the 14th amino acid proline substituted by alanine, which is also shown in a space filling model. P3 had the first 4 N-terminal amino acids deleted. P4 had first 7 N-terminal amino acids deleted. P5 had the last 4 C-terminal amino acids deleted. P6 and P7 had another small peptide added to the C- and N-terminal of melittin, respectively.

The present invention provides an anchor peptide that may be utilized in several applications to link a variety of cargo complexes to a nanoparticle and facilitate the delivery of the cargo complex to a cell. In particular, the anchor peptide is a cationic, amphipathic alpha helical peptide that is capable of stably inserting into lipid membranes. Furthermore, the anchor peptide is typically functionalized so that it may bind a variety of cargo complexes. Suitable cargo complexes may include imaging, therapeutic, cytotoxic, or targeting complexes. Accordingly, the anchor peptide, which may be linked to a cargo complex, is capable of stably inserting into the lipid membrane of a nanoparticle. Upon delivery of the nanoparticle to a cell, the anchor peptide-cargo complex is capable of dissociating from the lipid membrane of the nanoparticle and stably associating with the lipid membrane of the cell, thereby delivering the cargo complex to the cell. In some embodiments, the anchor peptide may stably insert into the lipid bilayer of the cell, such that the associated cargo complex may be displayed on the surface of the cell. In other embodiments, the anchor peptide may penetrate the lipid bilayer of the cell, thereby delivering the associated cargo complex to the interior of the cell.

Accordingly, the present invention provides a nanoparticle comprising a stably inserted anchor peptide, a kit for preparing a nanoparticle comprising a stably inserted anchor peptide, and methods for adding cargo complexes to the nanoparticles.

(I) Nanoparticles Comprising a Universal Anchor Peptide (a) Anchor Peptide

One aspect of the present invention encompasses an anchor peptide that is capable of stably inserting into a lipid membrane. The lipid membrane may be a monolayer, a bilayer, or a multilaminar bilayer. Accordingly, the lipid membrane may be part of a nanoparticle, a cell, or a liposome.

In general, the anchor peptide comprises at least one hydrophobic segment. More specifically, the hydrophobic segment of the anchor peptide comprises at least one amphipathic alpha helix. In some embodiments, the anchor peptide may comprise two amphipathic alpha helices. In other embodiments, the anchor peptide may comprise more than two alpha helices. The anchor peptide may also contain at least one hydrophilic segment. In some embodiments, the hydrophilic segment is positively charged. That is, the hydrophilic segment comprises a majority of positively charged amino acids (i.e., Arg, Lys, or His). Preferably, the overall charge of the anchor peptide is cationic. Thus, an exemplary anchor peptide comprises a cationic amphipathic alpha helical peptide. Accordingly, the amphipathic alpha helical segment stably inserts into a lipid membrane and the hydrophilic cationic segment remains on the surface of the lipid membrane.

As used herein, the terms "stably inserts" or "stably inserted" indicate that the hydrophobic segment of the anchor peptide integrates into the midst of a lipid monolayer or bilayer membrane. Stated another way, the amphipathic alpha helical segment of the anchor peptide interdigitates with the lipid membrane. The interactions between the hydrophobic amino acids of the anchor peptide and the lipid membrane are non-covalent hydrophobic interactions and/or van der Waals interactions. In embodiments in which the overall charge of the anchor peptide is positive, the stable integration of the anchor peptide into a lipid membrane may be assessed by changes in the zeta potential of the membrane. Specifically, the zeta potential shifts to a more positive value upon stable insertion of the positively charged anchor peptide into the lipid membrane.

In general, the anchor peptide has a high association affinity for a lipid membrane and a small dissociation constant, which allows it to rapidly and stably insert into a lipid membrane. In general, the association rate is typically greater than about $9.0 \times 10^5$ $M^{-1}$ $s^{-1}$. In some embodiments, the association rate may be greater than about $1.0 \times 10^6$, $2.0 \times 10^6$, $3.0 \times 10^6$, $4.0 \times 10^6$, $5.0 \times 10^6$, $6.0 \times 10^6$, $7.0 \times 10^6$, $8.0 \times 10^6$, $9.0 \times 10^6$, or $1.0 \times 10^7$ $M^{-1}$ $s^{-1}$. In an exemplary embodiment, the association rate may be greater than about $4.0 \times 10^6$ $M^{-1}$ $s^{-1}$. Methods of calculating the association rate are known in the art, and may, for instance, be calculated using the Biacore system.

The dissociation constant typically is less than about $1.0 \times 10^{-6}$ M. In some embodiments, the dissociation constant may be between about $1.0 \times 10^{-6}$ and $1.0 \times 10^{-7}$ M. In other embodiments, the dissociation constant may be between about $1.0 \times 10^{-7}$ and $1.0 \times 10^{-8}$ M. In still other embodiments, the dissociation constant may be between about $1.0 \times 10^{-8}$ and $1.0 \times 10^{-9}$ M. In yet other embodiments, the dissociation constant may be less than $9.9 \times 10^{-10}$ M. Methods of calculating the dissociation rate are known in the art, and may, for instance, be calculated using the Biacore system, as detailed in Example 2.

Furthermore, the anchor peptide is substantially non-lytic and non-cytotoxic to cells. Although the anchor peptide is substantially non-lytic and non-cytotoxic, a cargo complex conjugated to the anchor peptide may be lytic or cytotoxic (as detailed below). The term "non-lytic" means that the lipid bilayer of the cell typically is not compromised upon contact with the anchor peptide. The integrity of the lipid bilayer may be assessed by the improper entry or exit of cellular or extracellular components into a cell. For example, cellular proteins and/or organelles may leak out of a cell with a compromised lipid bilayer. Alternatively, extracellular components (i.e., those that normally do not enter via gap junctions, for example) may enter a cell with a compromised lipid bilayer. It should be noted, however, that the anchor peptide may penetrate the lipid bilayer of a cell and enter the interior of the cell, but in doing so the integrity of the lipid bilayer is not affected. The term "non-cytotoxic" indicates that the cell typically is not killed upon contact with the anchor peptide. For example, in one embodiment, more than 95% of the cells are viable after contact with the anchor peptide for at least 3 hours. More preferably, more than 99% of the cells are viable after contact with the anchor peptide for at least 3 hours. In embodiments in which the anchor peptide is a derivative or mutant of melittin (see below), the cytotoxicity index or IC50 of the anchor peptide will generally be at least about 50-fold higher than that of melittin.

As stated above, the anchor peptide comprises at least one hydrophobic segment and preferably at least one hydrophilic segment. The hydrophobic segment comprises mainly non-polar amino acids, such as Phe (F), Met (M), Ala (A), Gly (G), Ile (I), Leu (L), Val (V), Pro (P), Cys (C), or Trp (W). In some embodiments about 70%, 75%, 80%, 85%, 90%, 95%, or 100% of the amino acids of a hydrophobic segment of an anchor peptide are hydrophobic as defined herein. The optional hydrophilic segment of the anchor peptide comprises primarily polar amino acids, such as, Tyr (Y), Ser (S), Thr (T), Lys (K), His (H), Gln (Q), Glu (E), Arg (R), Asp (D), or Asn (N). In some embodiments about 70%, 75%, 80%, 85%, 90%, 95%, or 100% of the amino acids of a hydrophilic segment of an anchor peptide are hydrophilic as defined herein.

The length of the anchor peptide can and will vary depending upon the intended use of the anchor peptide and/or the intended cargo complex to be linked to the anchor peptide. The anchor peptide (i.e., in the absence of any conjugated cargo) may range from about 10 amino acids to about 50 amino acids in length. In general, at least one amphipathic alpha helical segment of the anchor peptide is long enough to stably interact with the lipid membrane, but short enough to avoid unwanted molecular interactions. In some embodiments, the amphipathic alpha helical segment may be between about 5 amino acids and about 20 amino acids in length. In other embodiments, the amphipathic alpha helical segment may be between about 5 amino acids and about 18 amino acids in length. In certain embodiments, the amphipathic alpha helical segment may be between about 5 amino acids and about 13 amino acids in length. In still other embodiments, the amphipathic alpha helical segment may be between about 5 amino acids and about 10 amino acids in length. In yet other embodiments, the amphipathic alpha helical segment may be between about 5 amino acids and about 8 amino acids in length. Similarly, the optional hydrophilic segment of the anchor peptide may range from about 3 amino acids to about 10 amino acids in length. In some embodiments, however, the hydrophilic segment may represent a conjugated cargo complex. Thus, depending on the role of the hydrophobic anchoring segment, the hydrophilic segment may be a cargo peptide or protein, an antibody or antibody fragment, genomic material (i.e., DNA or RNA), or a natural or synthetic small molecule (see section (I)(c) below).

In one preferred embodiment, the at least one hydrophobic segment of the anchor peptide may comprise at least the amino acid sequence ALISWI (SEQ ID NO:1) or the amino acid sequence AWISWI (SEQ ID NO:2). In another embodiment, the hydrophobic segment may comprise SEQ ID NO:1 or SEQ ID NO:2 and additional N-terminal or C-terminal hydrophobic amino acid residues or a substantially hydrophobic amino acid sequence. The at least one hydrophilic segment of the anchor peptide may be located on the N-terminal side of the hydrophobic or amphipathic alpha helical segment, or alternatively, on the C-terminal side of the hydrophobic or amphipathic alpha helical segment. In some preferred embodiments, the hydrophilic segment may comprise at least the amino acid sequence KRKRQQ (SEQ ID NO:3) or C-terminal truncations thereof.

In other preferred embodiments, the anchor peptide may comprise the amino acid sequence $X_{aa1}$ALISWI$X_{aa2}$, (SEQ ID NO:4) or the amino acid sequence $X_{aa1}$AWISWI$X_{aa2}$ (SEQ ID NO:5), wherein $X_{aa1}$ represents a hydrophobic amino acid as defined above, and $X_{aa2}$ represents a hydrophilic amino acid as defined above. In another preferred embodiment, the anchor peptide may comprise the amino acid sequence $X_{aa1}$GLX$_{aa3}$ALISWIKRKRQQ (SEQ ID NO:6) or the amino acid sequence $X_{aa1}$GLX$_{aa3}$AWISWIKRKRQQ (SEQ ID NO:7), wherein $X_{aa1}$ is as defined above, and $X_{aa3}$ may represent an amino acid selected from the group comprising Pro (P), Ala (A), Met (M), Leu (L), Ile (I), or Trp (W). In some embodiments, $X_{aa3}$ may be located on the same face of the alpha helix as other non-polar amino acids and may be a non-polar amino acid. If $X_{aa3}$ is a non-polar amino acid on the same face of the alpha helix as other non-polar amino acids, $X_{aa3}$ may facilitate association with a lipid membrane.

In still yet another embodiment, the anchor peptide may comprise the amino acid sequence $X_{aa1}$TTGLX$_{aa3}$ALISWIKRKRQQ (SEQ ID NO:8) or the amino acid sequence $X_{aa1}$TTGLX$_{aa3}$AWISWIKRKRQQ (SEQ ID NO:9), wherein $X_{aa1}$ and $X_{aa3}$ are as defined above. As above, in some embodiments $X_{aa3}$ may be located on the same face of the alpha helix as other non-polar amino acids and may be a non-polar amino acid. If $X_{aa3}$ is a non-polar amino acid on the same face of the alpha helix as other non-polar amino acids, $X_{aa3}$ may facilitate association with a lipid membrane.

In exemplary embodiments, the anchor peptide may consist of an amino acid sequence selected from the group consisting of SEQ ID NO:10 to SEQ ID NO:218, as detailed in Table A. In an especially exemplary embodiment, the anchor peptide may consist of the amino acid sequence of SEQ ID NO:88.

TABLE A

Exemplary Amino Acid Sequences of the Anchor Peptide

| Amino Acid Sequence | SEQ ID NO: |
| --- | --- |
| GIGAWLKVLTTGLPALISWIKRKRQQ | 10 |
| GIGAWLKVLTTGLPALISWIKRKRQ | 11 |
| GIGAWLKVLTTGLPALISWIKRKR | 12 |
| IGAWLKVLTTGLPALISWIKRKRQQ | 13 |
| IGAWLKVLTTGLPALISWIKRKRQ | 14 |
| IGAWLKVLTTGLPALISWIKRKR | 15 |
| GAWLKVLTTGLPALISWIKRKRQQ | 16 |
| GAWLKVLTTGLPALISWIKRKRQ | 17 |
| GAWLKVLTTGLPALISWIKRKR | 18 |
| AWLKVLTTGLPALISWIKRKRQQ | 19 |
| AWLKVLTTGLPALISWIKRKRQ | 20 |
| AWLKVLTTGLPALISWIKRKR | 21 |
| WLKVLTTGLPALISWIKRKRQQ | 22 |
| WLKVLTTGLPALISWIKRKRQ | 23 |
| WLKVLTTGLPALISWIKRKR | 24 |
| GIGAVLKVLTTGLAALISWIKRKRQQ | 25 |
| GIGAVLKVLTTGLAALISWIKRKRQ | 26 |

TABLE A-continued

Exemplary Amino Acid Sequences of the Anchor Peptide

| Amino Acid Sequence | SEQ ID NO: |
|---|---|
| GIGAVLKVLTTGLAALISWIKRKR | 27 |
| IGAVLKVLTTGLAALISWIKRKRQQ | 28 |
| IGAVLKVLTTGLAALISWIKRKRQ | 29 |
| IGAVLKVLTTGLAALISWIKRKR | 30 |
| GAVLKVLTTGLAALISWIKRKRQQ | 31 |
| GAVLKVLTTGLAALISWIKRKRQ | 32 |
| GAVLKVLTTGLAALISWIKRKR | 33 |
| AVLKVLTTGLAALISWIKRKRQQ | 34 |
| AVLKVLTTGLAALISWIKRKRQ | 35 |
| AVLKVLTTGLAALISWIKRKR | 36 |
| VLKVLTTGLAALISWIKRKRQQ | 37 |
| VLKVLTTGLAALISWIKRKRQ | 38 |
| VLKVLTTGLAALISWIKRKR | 39 |
| LKVLTTGLAALISWIKRKRQQ | 40 |
| LKVLTTGLAALISWIKRKRQ | 41 |
| LKVLTTGLAALISWIKRKR | 42 |
| KVLTTGLAALISWIKRKRQQ | 43 |
| KVLTTGLAALISWIKRKRQ | 44 |
| KVLTTGLAALISWIKRKR | 45 |
| VLTTGLAALISWIKRKRQQ | 46 |
| VLTTGLAALISWIKRKRQ | 47 |
| VLTTGLAALISWIKRKR | 48 |
| LTTGLAALISWIKRKRQQ | 49 |
| LTTGLAALISWIKRKRQ | 50 |
| LTTGLAALISWIKRKR | 51 |
| TTGLAALISWIKRKRQQ | 52 |
| TTGLAALISWIKRKRQ | 53 |
| TTGLAALISWIKRKR | 54 |
| TGLAALISWIKRKRQQ | 55 |
| TGLAALISWIKRKRQ | 56 |
| TGLAALISWIKRKR | 57 |
| GLAALISWIKRKRQQ | 58 |
| GLAALISWIKRKRQ | 59 |
| GLAALISWIKRKR | 60 |
| LAALISWIKRKRQQ | 61 |
| LAALISWIKRKRQ | 62 |
| LAALISWIKRKR | 63 |
| AALISWIKRKRQQ | 64 |
| AALISWIKRKRQ | 65 |
| AALISWIKRKR | 66 |
| ALISWIKRKRQQ | 67 |
| ALISWIKRKRQ | 68 |
| ALISWIKRKR | 69 |
| IGAVLKVLTTGLPALISWIKRKRQQ | 70 |
| IGAVLKVLTTGLPALISWIKRKRQ | 71 |
| IGAVLKVLTTGLPALISWIKRKR | 72 |
| GAVLKVLTTGLPALISWIKRKRQQ | 73 |
| GAVLKVLTTGLPALISWIKRKRQ | 74 |
| GAVLKVLTTGLPALISWIKRKR | 75 |
| AVLKVLTTGLPALISWIKRKRQQ | 76 |
| AVLKVLTTGLPALISWIKRKRQ | 77 |
| AVLKVLTTGLPALISWIKRKR | 78 |
| VLKVLTTGLPALISWIKRKRQQ | 79 |
| VLKVLTTGLPALISWIKRKRQ | 80 |
| VLKVLTTGLPALISWIKRKR | 81 |
| LKVLTTGLPALISWIKRKRQQ | 82 |
| LKVLTTGLPALISWIKRKRQ | 83 |
| LKVLTTGLPALISWIKRKR | 84 |
| KVLTTGLPALISWIKRKRQQ | 85 |
| KVLTTGLPALISWIKRKRQ | 86 |
| KVLTTGLPALISWIKRKR | 87 |
| VLTTGLPALISWIKRKRQQ | 88 |
| VLTTGLPALISWIKRKRQ | 89 |
| VLTTGLPALISWIKRKR | 90 |
| LTTGLPALISWIKRKRQQ | 91 |
| LTTGLPALISWIKRKRQ | 92 |
| LTTGLPALISWIKRKR | 93 |
| TTGLPALISWIKRKRQQ | 94 |
| TTGLPALISWIKRKRQ | 95 |
| TTGLPALISWIKRKR | 96 |
| TGLPALISWIKRKRQQ | 97 |
| TGLPALISWIKRKRQ | 98 |
| TGLPALISWIKRKR | 99 |
| GLPALISWIKRKRQQ | 100 |

TABLE A-continued

Exemplary Amino Acid Sequences of the Anchor Peptide

| Amino Acid Sequence | SEQ ID NO: |
|---|---|
| GLPALISWIKRKRQ | 101 |
| GLPALISWIKRKR | 102 |
| LPALISWIKRKRQQ | 103 |
| LPALISWIKRKRQ | 104 |
| LPALISWIKRKR | 105 |
| PALISWIKRKRQQ | 106 |
| PALISWIKRKRQ | 107 |
| PALISWIKRKR | 108 |
| GIGAVLKVLTTGLPALISWIKRKRQ | 109 |
| GIGAVLKVLTTGLPALISWIKRKR | 110 |
| GIGAVLKVLTTGLPALISWIKRK | 111 |
| GIGAVLKVLTTGLPALISWIKR | 112 |
| GIGAVLKVLTTGLPALISWIK | 113 |
| GIGAWLKVLTTGLPAWISWIKRKRQQ | 114 |
| GIGAWLKVLTTGLPAWISWIKRKRQ | 115 |
| GIGAWLKVLTTGLPAWISWIKRKR | 116 |
| IGAWLKVLTTGLPAWISWIKRKRQQ | 117 |
| IGAWLKVLTTGLPAWISWIKRKRQ | 118 |
| IGAWLKVLTTGLPAWISWIKRKR | 119 |
| GAWLKVLTTGLPAWISWIKRKRQQ | 120 |
| GAWLKVLTTGLPAWISWIKRKRQ | 121 |
| GAWLKVLTTGLPAWISWIKRKR | 122 |
| AWLKVLTTGLPAWISWIKRKRQQ | 123 |
| AWLKVLTTGLPAWISWIKRKRQ | 124 |
| AWLKVLTTGLPAWISWIKRKR | 125 |
| WLKVLTTGLPAWISWIKRKRQQ | 126 |
| WLKVLTTGLPAWISWIKRKRQ | 127 |
| WLKVLTTGLPAWISWIKRKR | 128 |
| GIGAVLKVLTTGLAAWISWIKRKRQQ | 129 |
| GIGAVLKVLTTGLAAWISWIKRKRQ | 130 |
| GIGAVLKVLTTGLAAWISWIKRKR | 131 |
| IGAVLKVLTTGLAAWISWIKRKRQQ | 132 |
| IGAVLKVLTTGLAAWISWIKRKRQ | 133 |
| IGAVLKVLTTGLAAWISWIKRKR | 134 |
| GAVLKVLTTGLAAWISWIKRKRQQ | 135 |
| GAVLKVLTTGLAAWISWIKRKRQ | 136 |
| GAVLKVLTTGLAAWISWIKRKR | 137 |
| AVLKVLTTGLAAWISWIKRKRQQ | 138 |
| AVLKVLTTGLAAWISWIKRKRQ | 139 |
| AVLKVLTTGLAAWISWIKRKR | 140 |
| VLKVLTTGLAAWISWIKRKRQQ | 141 |
| VLKVLTTGLAAWISWIKRKRQ | 142 |
| VLKVLTTGLAAWISWIKRKR | 143 |
| LKVLTTGLAAWISWIKRKRQQ | 144 |
| LKVLTTGLAAWISWIKRKRQ | 145 |
| LKVLTTGLAAWISWIKRKR | 146 |
| KVLTTGLAAWISWIKRKRQQ | 147 |
| KVLTTGLAAWISWIKRKRQ | 148 |
| KVLTTGLAAWISWIKRKR | 149 |
| VLTTGLAAWISWIKRKRQQ | 150 |
| VLTTGLAAWISWIKRKRQ | 151 |
| VLTTGLAAWISWIKRKR | 152 |
| LTTGLAAWISWIKRKRQQ | 153 |
| LTTGLAAWISWIKRKRQ | 154 |
| LTTGLAAWISWIKRKR | 155 |
| TTGLAAWISWIKRKRQQ | 156 |
| TTGLAAWISWIKRKRQ | 157 |
| TTGLAAWISWIKRKR | 158 |
| TGLAAWISWIKRKRQQ | 159 |
| TGLAAWISWIKRKRQ | 160 |
| TGLAAWISWIKRKR | 161 |
| GLAAWISWIKRKRQQ | 162 |
| GLAAWISWIKRKRQ | 163 |
| GLAAWISWIKRKR | 164 |
| LAAWISWIKRKRQQ | 165 |
| LAAWISWIKRKRQ | 166 |
| LAAWISWIKRKR | 167 |
| AAWISWIKRKRQQ | 168 |
| AAWISWIKRKRQ | 169 |
| AAWISWIKRKR | 170 |
| AWISWIKRKRQQ | 171 |
| AWISWIKRKRQ | 172 |
| AWISWIKRKR | 173 |
| IGAVLKVLTTGLPAWISWIKRKRQQ | 174 |

TABLE A-continued

Exemplary Amino Acid Sequences of the Anchor Peptide

| Amino Acid Sequence | SEQ ID NO: |
|---|---|
| IGAVLKVLTTGLPAWISWIKRKRQ | 175 |
| IGAVLKVLTTGLPAWISWIKRKR | 176 |
| GAVLKVLTTGLPAWISWIKRKRQQ | 177 |
| GAVLKVLTTGLPAWISWIKRKRQ | 178 |
| GAVLKVLTTGLPAWISWIKRKR | 179 |
| AVLKVLTTGLPAWISWIKRKRQQ | 180 |
| AVLKVLTTGLPAWISWIKRKRQ | 181 |
| AVLKVLTTGLPAWISWIKRKR | 182 |
| VLKVLTTGLPAWISWIKRKRQQ | 183 |
| VLKVLTTGLPAWISWIKRKRQ | 184 |
| VLKVLTTGLPAWISWIKRKR | 185 |
| LKVLTTGLPAWISWIKRKRQQ | 186 |
| LKVLTTGLPAWISWIKRKRQ | 187 |
| LKVLTTGLPAWISWIKRKR | 188 |
| KVLTTGLPAWISWIKRKRQQ | 189 |
| KVLTTGLPAWISWIKRKRQ | 190 |
| KVLTTGLPAWISWIKRKR | 191 |
| VLTTGLPAWISWIKRKRQQ | 192 |
| VLTTGLPAWISWIKRKRQ | 193 |
| VLTTGLPAWISWIKRKR | 194 |
| LTTGLPAWISWIKRKRQQ | 195 |
| LTTGLPAWISWIKRKRQ | 196 |
| LTTGLPAWISWIKRKR | 197 |
| TTGLPAWISWIKRKRQQ | 198 |
| TTGLPAWISWIKRKRQ | 199 |
| TTGLPAWISWIKRKR | 200 |
| TGLPAWISWIKRKRQQ | 201 |
| TGLPAWISWIKRKRQ | 202 |
| TGLPAWISWIKRKR | 203 |
| GLPAWISWIKRKRQQ | 204 |
| GLPAWISWIKRKRQ | 205 |
| GLPAWISWIKRKR | 206 |
| LPAWISWIKRKRQQ | 207 |
| LPAWISWIKRKRQ | 208 |
| LPAWISWIKRKR | 209 |
| PAWISWIKRKRQQ | 210 |
| PAWISWIKRKRQ | 211 |
| PAWISWIKRKR | 212 |
| GIGAVLKVLTTGLPAWISWIKRKRQQ | 213 |
| GIGAVLKVLTTGLPAWISWIKRKRQ | 214 |
| GIGAVLKVLTTGLPAWISWIKRKR | 215 |
| GIGAVLKVLTTGLPAWISWIKRK | 216 |
| GIGAVLKVLTTGLPAWISWIKR | 217 |
| GIGAVLKVLTTGLPAWISWIK | 218 |

The anchor peptide of the invention may be produced using means commonly known in the art.

(b) Functionalization

As stated above, the anchor peptide may be functionalized so as to form a bond with a cargo complex. Generally speaking, the anchor peptide may be functionalized with any of a variety of active groups known in the art so as to facilitate bond formation with a cargo complex. The bond may be a covalent bond or a non-covalent bond. For instance, the bond may be a covalent bond, a hydrogen bond, an ionic bond, a bond based on van der Waals, or a hydrophobic bond. One of skill in the art would recognize that the choice of functional group can and will vary depending on the cargo complex.

By way of non-limiting example, the anchor peptide may be functionalized with an active group, such as a photo-reactive group, that when contacted with light may become activated, and capable of covalently attaching to the cargo complex. Exemplary reactive groups include, but are not limited to, reactive groups typically used in the preparation of chromatography media which include: epoxides, oxiranes, esters of N-hydroxysuccinimide, aldehydes, hydrazines, maleimides, mercaptans, amino groups, alkylhalides, isothiocyanates, carbodiimides, diazo compounds, tresyl chloride, tosyl chloride, and trichloro S-triazine. Exemplary photo-reactive groups include aryl azides, diazarenes, beta-carbonyldiazo, and benzophenones. The reactive species are nitrenes, carbenes, and radicals. These reactive species are generally capable of covalent bond formation.

In some embodiments, the anchor peptide may be functionalized with a bi-functional peptide that would connect the anchor peptide to the cargo complex. The bi-functional peptide may be homo-bi-functional or hetero-bi-functional.

Methods of functionalizing the anchor peptide are known in the art.

(c) Cargo Complex

The anchor peptide may be bound to a cargo complex. The means by which the complex is associated with the anchor peptide can and will vary depending on the embodiment. The cargo complex may be covalently or non-covalently bound to the anchor peptide, as detailed above. The cargo complex may be any molecule or agent that may be carried by or bound to the anchor peptide of a nanoparticle, and in some instances, may even be a complex of micron size. For instance, the cargo complex may be an imaging cargo, a therapeutic cargo, a cytotoxic cargo, or a targeting cargo.

(i) Imaging Cargo

Non-limiting examples of imaging cargo molecules and agents may include any molecule, agent, or material having a detectable physical or chemical property. Such imaging cargos have been well-developed in the field of fluorescent imaging, magnetic resonance imaging, positron emission tomography, Raman imaging, optical coherence tomography, photoacoustic imaging, Fourier transform infrared imaging, or immunoassays and, in general, most any label useful in such methods may be applied to the present invention. Thus, an imaging cargo may be any molecule or agent detectable by spectroscopic, photochemical, biochemical, immunochemical, electrical, optical, physical (e.g. atomic force microscopy) or chemical means. Useful imaging molecules and agents in the present invention may include visible or infrared fluorescent dyes (e.g., fluorescein isothiocyanate, AlexaFluor555, Texas red, rhodamine, and the like), radiolabels (e.g., $^{3}H$, $^{14}C$, $^{35}S$, $^{125}I$, $^{121}I$, $^{112}In$, $^{99}mTc$), other imaging agents such as microbubbles or nanobubbles (for ultrasound imaging), $^{18}F$, $^{11}C$, $^{15}O$, (for positron emission tomography), $^{99}mTC$, $^{111}In$ (for single photon emission tomography), gadolinium chelate or iron (for magnetic resonance imaging), enzymes (e.g., horse radish peroxidase, alkaline phosphatase and others commonly used in an ELISA), and calorimetric labels such as colloidal gold or colored glass or plastic (e.g. polystyrene, polypropylene, latex, and the like) beads. Patents that describe the use of such imaging molecules include U.S. Pat. Nos. 3,817,837; 3,850,752; 3,939,350; 3,996,345; 4,277,437; 4,275,149; and 4,366,241, each incorporated herein by reference in their entirety. See also Handbook of Fluorescent Probes and Research Chemicals, 6th Ed., Molecular Probes, Inc., Eugene Oreg.

The anchor peptide may also be conjugated directly to signal generating compounds, e.g., by conjugation with an enzyme or fluorophore. Enzymes of interest may be hydrolases, particularly phosphatases, esterases and glycosidases, or oxidoreductases, particularly peroxidases. Fluorescent compounds may include fluorescein and its derivatives, rhodamine and its derivatives, dansyl, umbelliferone, and the like. Chemiluminescent compounds may include luciferin, and 2,3-dihydrophthalazinediones, e.g., luminol. For a review of various labeling or signal producing systems that may be used, see U.S. Pat. No. 4,391,904, incorporated herein by reference in its entirety.

(ii) Therapeutic Cargo

Non-limiting examples of therapeutic cargo may include any substance that has a biological activity, such as pharmacological agents. Such therapeutic cargo may include analgesics, antipyretics, antiasthamatics, antibiotics, antidepressants, antidiabetics, antifungal agents, antihypertensive agents, anti-inflammatories including non-steroidal and steroidal, antineoplastics, antianxiety agents, immunosuppressive agents, antimigraine agents, sedatives, hypnotics, anti-anginal agents, antipsychotic agents, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines, anti-restenosis agents, antipruritics, agents useful for calcium regulation, antibacterial agents, antiviral agents, antimicrobials, anti-infectives, bronchodilators, steroidal compounds and hormones, and combinations thereof. Alternatively, the cargo complex could be in the form of components of molecular complexes or pharmacologically acceptable salts.

Suitable therapeutic cargos include, without limit, immune-related agents such as immune serums, antitoxins, antivenoms bacterial vaccines, viral vaccines, rabies prophylaxis products; thyroid agents such as iodine products and anti-thyroid agents; respiratory products such as xanthine derivatives theophylline and aminophylline; antineoplastic agents such as platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, paclitaxel and other taxenes, rapamycin, manumycin A, TNP-470, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, interferon α-2a, interferon α-2b, teniposide (VM-26), vinblastine sulfate (VLB), vincristine sulfate, bleomycin sulfate, hydroxyurea, procarbazine, and dacarbazine; anti-helmintics such as pyrantel pamoate, piperazine, tetrachloroethylene, thiabendazole, and niclosamide; antimalarials such as chloroquine, amodiaquine, antifolate drugs, proguanil (chloroguanide), mefloquine, quinine, halofantrine, artemesinin and derivaties, primaquine, doxycycline, tetracycline, and clindamycin; mitotic inhibitors such as tauromustine, bofumustine, fotemustine, etoposide, colchicine, methotrexate, fluorouracil, 5-bromodeoxyuridine, 6-azacytidine, cytarabine and the vinca alkaloids, such as vincristine, paclitaxel, etoposide, nocodazole, indirubin, anthracycline derivatives, daunorubicin, daunomycin, plicamycin, and the like; hormones such as androgens, progestins, estrogens and antiestrogens, growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, vassopressin, glucagon and their derivatives; antiprotozoans such as chloroquine, hydroxychloroquine, metronidazole, quinine, and meglumine antimonite; antituberculars such as para-aminosalicylic acid, isoniazid, capreomycin sulfate cycloserine, ethambutol hydrochloride ethionamide, pyrazinamide, rifampin, and streptomycin sulfate; cardiovascular products such as chelating agents and mercurial diuretics and cardiac glycosides; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-alanyl-D-isoglutamine, and the like; anti-fungal agents such as ketoconazole, nystatin, griseofulvin, flucytosine (5-fc), miconazole, amphotericin B, ricin, cyclosporins, and β-lactam antibiotics (e.g., sulfazecin); vitamins such as cyanocobalamin neinoic acid, retinoids and derivatives such as retinol palmitate, and α-tocopherol; peptides such as manganese super oxide dismutase; enzymes such as alkaline phosphatase; anti-allergic agents such as amelexanox; anti-coagulation agents such as phenprocoumon, and heparin; circulatory drugs such as propranolol and other beta blockers;

metabolic potentiators such as glutathione; antivirals such as acyclovir, amantadine azidothymidine (AZT, DDI, Foscarnet, or Zidovudine), ribavirin and vidarabine monohydrate (adenine arabinoside, ara-A); antianginals such as diltiazem, nifedipine, verapamil, erythritol tetranitrate, isosorbide dinitrate, nitroglycerin (glyceryl trinitrate) and pentaerythritol tetranitrate; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin, aminoglycosides, and tetracycline; antiinflammatories such as diflunisal, ibuprofen, indomethacin, meclofenamate, mefenamic acid, naproxen, oxyphenbutazone, phenylbutazone, piroxicam, sulindac, tolmetin, aspirin, and salicylates; antirheumatics such as adalimumab, azathioprine, chloroquine and hydroxychloroquine (antimalarials), cyclosporine (Cyclosporin A), D-penicillamine, etanercept, gold salts (sodium aurothiomalate, auranofin), infliximab, leflunomide, methotrexate, minocycline (a tetracycline antibiotic), and sulfasalazine; narcotics such as paregoric, opiates, codeine, heroin, methadone, morphine, and opium; cardiac glycosides such as deslanoside, digitoxin, digoxin, digitalin, and digitalis; neuromuscular blockers such as atracurium mesylate, gallamine triethiodide, hexafluorenium bromide, metocurine iodide, pancuronium bromide, succinylcholine chloride (suxamethonium chloride), tubocurarine chloride, and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam, and triazolam; local anesthetics such as bupivacaine hydrochloride, chloroprocaine hydrochloride, etidocaine hydrochloride, lidocaine hydrochloride, mepivacaine hydrochloride, procaine hydrochloride, and tetracaine hydrochloride; general anesthetics such as droperidol, etomidate, fentanyl citrate with droperidol, ketamine hydrochloride, methohexital sodium, and thiopental sodium; radioactive particles or ions such as strontium, iodide rhenium, yttrium; and radiopharmaceuticals such as radioactive iodine and phosphorus products.

(iii) Cytotoxic Cargo

Cytotoxic cargo refers to a molecule or agent that is detrimental to (e.g., kills or damages) a cell. Examples may include anti-microtubule drugs such as the taxols (paclitaxel, docetaxel) and vinca alkaloids (vincristine, vinblastine). For instance, examples may include taxol, cytochalasin B, gramicidin D, ethidium bromide, emetine, mitomycin, etoposide, tenoposide, vincristine, vinblastine, colchicin, doxorubicin, daunorubicin, dihydroxy anthracin didne, mitoxantrone, mithramycin, actinomycin D, 1-dehydrotestosterone, glucocorticoids, procaine, tetracaine, lidocaine, propranolol, and puromycin and analogs or homologs thereof.

Non-limiting examples of cytotoxic cargo may also include radionuclides suitable for pharmacological administration. Such radionuclides may include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Additionally, cytotoxic agents may include chemotoxic agents or toxins. Examples of chemotoxic agents may include small-molecule drugs such as methotrexate, and pyrimidine and purine analogs.

Proteins that may be used as cytotoxic agents may include ricin, abrin, diphtheria toxin, cholera toxin, gelonin, *Pseudomonas* exotoxin, *Shigella* toxin, pokeweed antiviral protein, and other toxin proteins known in the medicinal biochemistry arts.

(iv) Targeting Cargo

Targeting cargo may be any molecule or agent that directs a nanoparticle to a specific location. Non-limiting examples of targeting agents may include an antibody or antibody fragment, receptor ligand, small molecule, peptide, polypeptide, lipid, carbohydrate, nucleic acid, siRNA, shRNA, antisense RNA, dendrimer, microbubble, or aptamer. A targeting cargo may be directed to a eukaryotic target cell or a prokaryotic target cell.

(d) Nanoparticles

Generally speaking, the nanoparticle comprises a core encapsulated by a lipid layer. The lipid membrane of the nanoparticle may comprise a single lipid layer, two lipid layers (a bilayer), more than two lipid layers, a multilaminar lipid layer, and the like. As used herein, the term nanoparticle encompasses particle carriers that may be nano scale, micro scale, or macro scale. Suitable particle carriers include nanoparticles, nanospheres, nanostructures, liposomes, micelles, microbubbles, gas-filled microbubbles, dendrimers, polymeric structures, or any such carrier (naturally occurring or synthetic) that has an exterior lipid layer into which the anchor peptide may stably insert. Bacteria, viruses, prions, red blood cells, white blood cells, isolated tissue cells, platelets, and other such biologically derived, lipid-encased structures also may be carriers of the anchor peptide. Structures comprising a glycolipid membrane surrounding a cell (animal or vegetable) or particle or synthetic nanostructure also are potential hosts for the anchor peptide. In exemplary embodiments, the particle carrier may be a lipid-encapsulated nanoparticle.

In some embodiments, the anchor peptide may be bound to a cargo complex, as described above. The anchor peptide itself is generally non-lytic and non-cytotoxic, but the cargo complex may be lytic or cytotoxic. In some embodiments, a single nanoparticle may be associated with more than one type of cargo complex. For instance, a nanoparticle may be associated with both an anchor peptide bound to a targeting cargo and an anchor peptide bound to a therapeutic cargo. In one embodiment, a nanoparticle may be associated with at least 2, 3, 4, 5, 6, 7, 8, 9, or 10 different cargo complexes. In another embodiment, a nanoparticle may be associated with at least one therapeutic cargo, at least one imagining cargo, at least one cytotoxic cargo, at least one targeting cargo, or any combination thereof.

Methods of making lipid-encapsulated nanoparticles are well known in the art. For instance, see U.S. Pat. Nos. 6,676, 963, 7,255,875 and 7,186,399, herein incorporated by reference in their entirety. As described below, a nanoparticle may be initially produced with an anchor peptide, or, alternatively, a nanoparticle may be pre-formed, and the anchor peptide subsequently added to the lipid membrane. Methods of adding an anchor peptide to a pre-formed nanoparticle are described in more detail below.

(e) Administration

Nanoparticles comprising an anchor peptide, which may be linked to a cargo complex, may be administered to a subject. Suitable subjects include, but are not limited to, mammals, amphibians, reptiles, birds, fish, insects, and plants. In certain embodiments, nanoparticles of the invention may be used to image a tissue from a subject. Tissue, as used herein, may refer to cells, organs, tumors, or material associated with cells, organs, or tumors, such as blood clots. Suitable tissues may include, but are not limited to, heart, lungs, brain, eye, stomach, spleen, bones, pancreas, kidneys, liver, intestines, skin, uterus, bladder, eyes, lymph nodes, blood vessels, and blood and lymph components.

The nanoparticles may be formulated and administered to a subject by several different means. For instance, nanoparticles may generally be administered parenteraly, intraperitoneally, intravascularly, topically, or intrapulmonarily in dosage unit formulations containing conventional nontoxic pharmaceutically acceptable carriers, adjuvants, and vehicles as desired. The term parenteral as used herein includes subcutaneous, intravenous, intramuscular, intrathecal, or intrasternal injection, or infusion techniques. In one embodiment, the composition may be administered in a bolus. In a preferred embodiment, the composition may be administered intravenously. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

For imaging purposes, formulations for parenteral administration may be in the form of aqueous or non-aqueous isotonic or hypotonic sterile injection solutions or suspensions. These solutions and suspensions may be prepared from sterile powders or granules having one or more carriers or diluents. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

One of skill in the art will recognize that the amount and concentration of the composition administered to a subject will depend in part on the subject and the reason for the administration (i.e. imaging, drug delivery, etc.). Methods for determining optimal amounts are known in the art. In one embodiment, the amount administered may be between about 0.1 cc/kg to about 5 cc/kg. In another embodiment, the amount administered may be about 0.5, 1.0, 1.5, 2.0, 2.5, 3.0, 3.5, 4.0, 4.5, or 5.0 cc/kg. In yet another embodiment, the amount may be 1 cc/kg.

Figure 7:
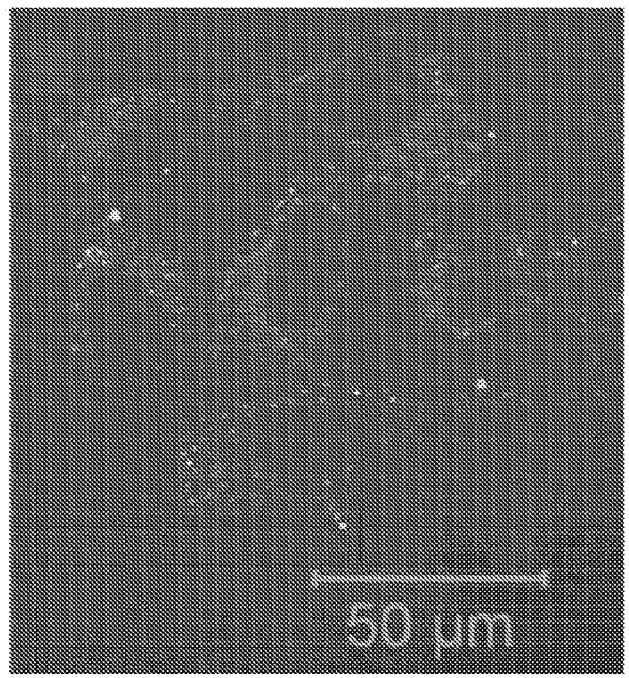
FIG. 7 presents a micrograph showing the cellular distributions of FITC labeled linker peptide 1-associated PFOB nanoparticles in C-32 melanoma cells as visualized by confocal microscopy. (A) Cells exposed to FITC labeled linker peptide 1-associated PFOB nanoparticles. (B) Cells exposed to plain PFOB nanoparticles.
Figure 7:
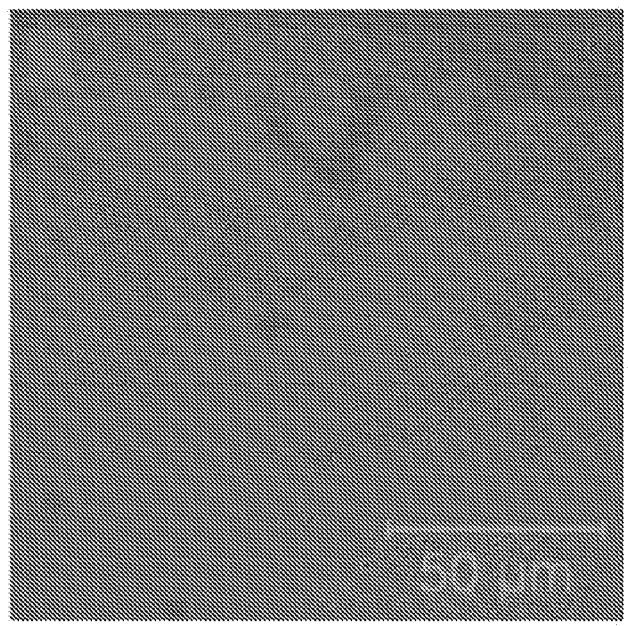
Figure 11:
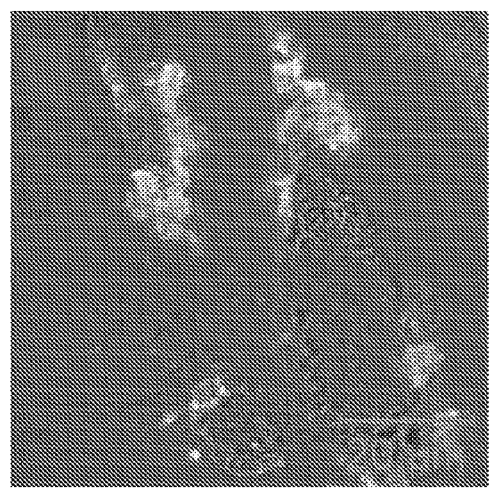
FIG. 11 presents micrographs showing the cellular distribution of Alexa Fluor 488 labeled nanoparticles with VCAM-targeting peptide TCP1 (A), Alexa Fluor 488 labeled nanoparticles with VCAM-targeting peptide TCP2 (B), and nanoparticles without the VCAM-targeting peptide (C) in mouse endothelial cells (2F2B cells).
Figure 11:
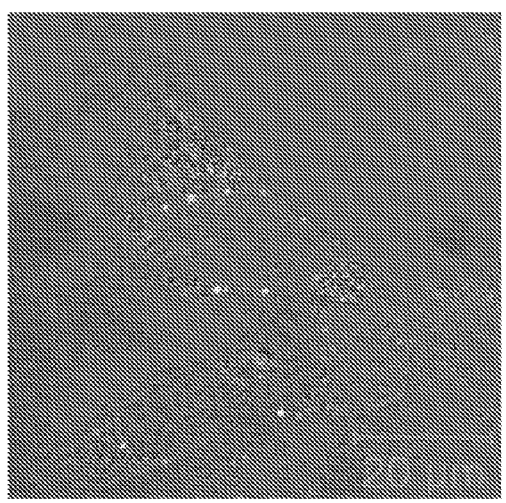
Figure 11:
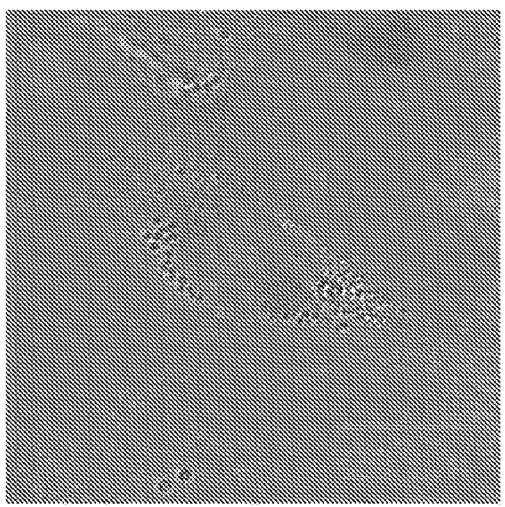

Following administration, the nanoparticle comprising the anchor peptide contacts a cell. As detailed above and demonstrated in Example 5, the nanoparticle may be targeted to a particular cell by linking a specific targeting cargo to the anchor peptide of the nanoparticle. Upon contact with the cell, the anchor peptide of the nanoparticle may be transferred or move from the lipid monolayer of the nanoparticle and interact with and stably insert into the lipid bilayer of the cell. Depending upon the type of cargo complex that is linked to the anchor peptide, the anchor peptide may remain tethered to the lipid membrane of the cell. In such an embodiment, the cargo complex is on the surface of the cell via its attachment to the hydrophilic segment of the anchor peptide, whereas the hydrophobic segment of the anchor peptide is stably integrated into the lipid bilayer of the cell. In other embodiments, the anchor peptide and linked cargo complex may penetrate the lipid bilayer and enter the cell cytoplasm (as demonstrated in Examples 3 and 5, and depicted in FIG. 7 and FIG. 11). In such an embodiment, the cargo that is linked to the anchor peptide may be an imaging agent or a therapeutic agent, for example. Those of skill in the art will appreciate that a number of scenarios are possible, depending upon the properties of the anchor peptide and the conjugated cargo complex.

(II) Kits

In some embodiments, the invention encompasses a kit. The kit generally comprises a first composition comprising a nanoparticle, and a second composition comprising an anchor peptide. In exemplary embodiments, the nanoparticle of the kit may be pre-formed. By following directions provided by the kit, a user of the kit may bind the anchor peptide to a cargo complex of interest, and then mix the conjugated anchor peptide/cargo complex with the pre-formed nanoparticles, so as to incorporate the anchor peptide into the lipid membrane of the pre-formed nanoparticle. In some embodiments, the pre-formed nanoparticles may be sterile.

(III) Methods

Yet another aspect of the present invention encompasses methods for adding a cargo complex to a nanoparticle. A first method generally comprises contacting the nanoparticle with an anchor peptide that is bound to a cargo complex. The anchor peptide stably inserts into the lipid membrane of the nanoparticle, thereby linking the cargo complex with the nanoparticle. This method advantageously allows the nanoparticle to be pre-formed and then loaded with one or more cargo complexes at a later time.

In one embodiment, a nanoparticle may be contacted with an anchor peptide by combining a composition comprising a nanoparticle with a composition comprising an anchor peptide under conditions suitable for the anchor peptide to stably insert into the lipid membrane of the nanoparticle. Typically, such conditions may comprise a temperature of about 20° C. to about 30° C., and incubation times of between about 30 sec and 30 min. In some embodiments, a nanoparticle may be incubated with the anchor peptide for about 5, 10, 15, 20, or 25 minutes at a temperature between about 20° C. and 30° C. One skilled in the art will appreciate that the length and temperature of incubation can and will vary depending on the composition of the nanoparticle, the anchor peptide, and the cargo complex.

The ratio of the anchor peptide to the nanoparticle will also vary depending on the composition of the nanoparticle, the anchor peptide, and the cargo complex. Molar membrane lipid to anchor peptide ratios may range from about 1500 to about 20. In some embodiments, the ratio may range from about 1000 to about 40. In other embodiments, the ratio may be about 900, 800, 700, 600, 500, 400, 300, 200, 100, 90, 80, 70, 60, 50, 40, 30 or 20.

In one example, nanoparticles may be formulated by mixing known amounts of anchor peptides to perfluorocarbon nanoparticles. An anchor peptide may be dissolved in 100 mM KCl (pH 7, 10 mM HEPES) at 0.1 mM and 2×20 mL may be added to 50 ml of nanoparticle suspension with mixing. After incubation at room temperature for 10 min, the nanoparticles may be washed twice by centrifugation (100 g, 10 min) to remove unbound anchor peptide. In some embodiments in which the anchor peptide contains a tryptophan residue, the anchor peptide in the supernatant may be quantified by measuring the tryptophan fluorescence using methods known in the art.

A second method comprises adding a cargo complex to a nanoparticle comprising a stably inserted (functionalized) anchor peptide. The starting nanoparticle may already comprise at least one cargo complex that was previously conjugated with the stably inserted anchor peptide. The method comprises contacting the nanoparticle with the cargo complex, wherein the cargo complex forms a bond with the functionalized anchor peptide. The conditions under which the nanoparticle comprising the stably inserted anchor peptide is contacted with the cargo complex can and will vary depending upon, for example, the type of cargo complex and the type of functionalization of the anchor peptide. Those of skill in the art are familiar with suitable reaction conditions.

(IV) Anchor Peptides

A further aspect of the invention comprises an anchor peptide as detailed above in section (I)(a). In particular, an anchor peptide comprises a substantially non-lytic, non-cytotoxic, amphipathic alpha helical peptide that is capable of stably inserting into a lipid membrane. In general, the anchor peptide is cationic and comprises at least one amphipathic alpha helix.

Figure 15:
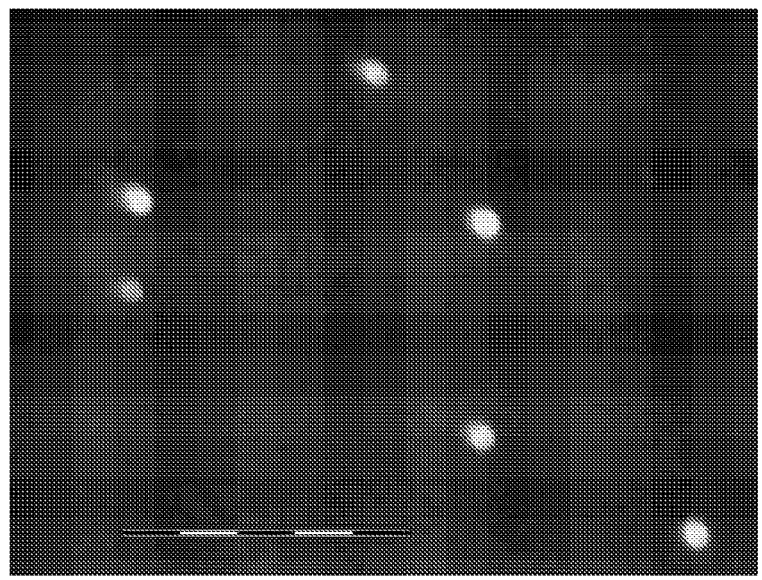
FIG. 15 shows that the linker peptide 1 itself can be used to label cells. FITC-conjugated linker peptide 1 was incubated with human red blood cells for 1 hour, and a fluorescence image (A) and a bright field image (B) were taken after washing. The scale bars represent 100 μm.
Figure 15:
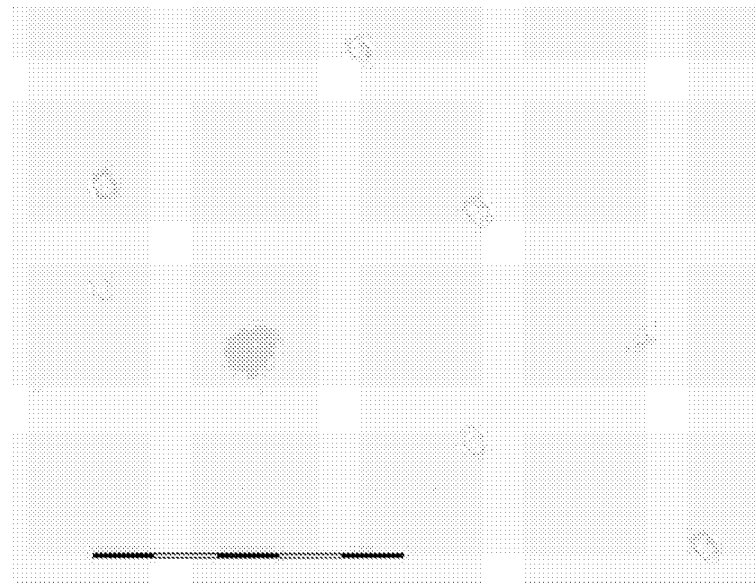

The anchor peptide may be associated with nanoparticles to facilitate the delivery of cargo complexes to cells, as detailed above in section (I). Alternatively, the anchor peptide itself may associate with and insert into the cell membranes of cells. Thus, the anchor peptide itself may be used to label cells, target cells, or deliver cargos to cells. As an example, the anchor peptide may be conjugated to a fluorescent molecule, wherein the anchor peptide may stably insert into the lipid bilayer of a cell and "label" the cell (as demonstrated in Example 7 and FIG. 15). In other embodiments, the anchor peptide may be conjugated to a specific targeting agent and/or therapeutic agent, such that conjugated anchor peptide is targeted to a specific cell or a therapeutic agent is delivered to the cell. As detailed above, the anchor peptide may stably integrate into the lipid membrane of the cell such that the conjugated agent is displayed on the cell surface. Alternatively, the anchor peptide may penetrate the cell membrane and deliver the conjugated agent to the interior of the cell. In general, the nature of the anchor peptide and the conjugated agent will determine the eventual fate of the conjugated anchor peptide. The anchor peptides of the invention, therefore, may be used as research tools or as medical tools for imaging and/or therapeutics.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1

Lytic Activity of Anchor Peptide

Typically, cargos such as targeting ligands, imaging agents, and/or drugs are incorporated into nanocariers during the formulation process, which requires a dedicated particle design and preformulation for each individual application. In contrast, a strategy designed to accommodate swapping and/or combining multiple cargos in generic base nanocarriers would enable flexible and personalized decision making for application to any disease. Despite the myriad regulatory hurdles to the adoption of such a paradigm, the design of flexible nanocarriers with polyvalent and rapidly swappable targeting and drug delivery cargos represents a necessary first step.

The first goal was to design an appropriate anchoring agent that could be used with generic nanoparticle carriers, and for this purpose the model peptide, melittin (MMLT), was selected. Melittin is a 26 amino acid peptide that comprises more than half of the dry weight of the venom of the honeybee *Apis mellifera*. Residues 1-20 of melittin form two amphipathic α-helixes with an intervening proline hinge, while residues 21-26 of melittin are highly positively charged. Both hydrophobic and hydrophilic segments of melittin are essential for its lytic activity. It was hypothesized that the structure of melittin could be modified to attenuate its lytic activity while retaining the property of stable insertion into perfluorocarbon (PFC) nanoparticles. Accordingly, the native melittin sequence was altered by selective point mutations and truncations. Table 1 presents the amino acid sequences of the various peptides and FIG. 1 presents schematics of their secondary structures.

TABLE 1

Melittin and Derivatives of Melittin

| Name(s) | Peptide Sequence | SEQ ID NO: |
|---|---|---|
| MMLT | GIGAVLKVLTTGLPALISWIKRKRQQ | 219 |
| P1 | GIGAWLKVLTTGLPALISWIKRKRQQ | 10 |
| P2 (LP2) | GIGAVLKVLTTGLAALISWIKRKRQQ | 25 |
| P3 | VLKVLTTGLPALISWIKRKRQQ | 79 |
| P4 (LP1) | VLTTGLPALISWIKRKRQQ | 88 |
| P5 | GIGAVLKVLTTGLPALISWIKR | 112 |
| P6 | GIGAVLKVLTTGLPALISWIKRKRQQALDWSWLQTE | 220 |
| P7 | TALDWSWLQTEGIGAVLKVLTTGLPALISWIKRKRQQ | 221 |

The peptides were synthesized automatically by Fmoc solid-phase peptide synthesis. The product identities were assessed by mass spectrometry (Washington University Proteomics Center, St. Louis, Mo.) and the purity (>99%) was determined by analytical HPLC. All the peptides contained N-terminal acetylation and C-terminal amidation to mimic the situation of covalent cargo attachment that would apply when these peptides would be used as a linker on the nanocarriers.

For each peptide, cytotoxicity was assessed in 2F2B mouse endothelial cells by the XTT cell viability assay (Biotium, Hayward, Calif.). Cells were seeded in 96-well plates at 10,000 cells/well 24 hours before treatment with melittin and mutated melittins at selected concentrations. After 3 hours of treatment at 37° C., 25 µl of activated XTT solution was added to each well and incubated at 37° C. for 5 hours. After 5 hours of incubation, plates were gently shaken to achieve even dye distribution. The absorbances of the samples were measured by a microplate reader (Biorad, Model 550, Hercules, Calif.) at a wavelength of 450 nm. Background was subtracted and the results were normalized to untreated control cells.

Figure 2:
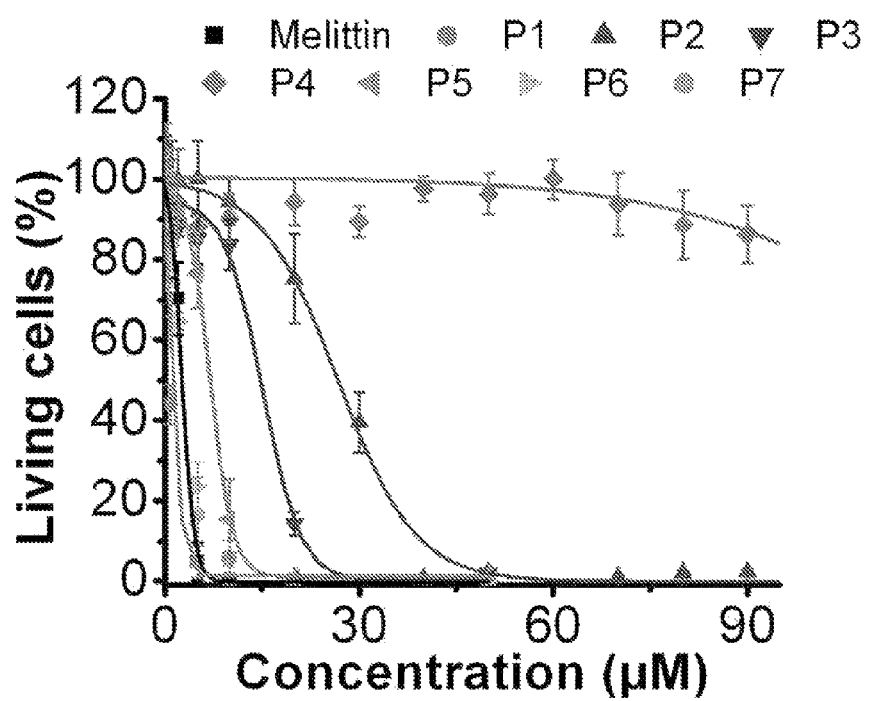
FIG. 2 presents a graph showing the cell lytic actions of native melittin and the melittin derivatives, as defined in FIG. 1. Plotted is the percent of live cells as a function of peptide concentration.

FIG. 2 presents the cytotoxicity results. Among the modified peptides, P2 and P4 exhibited the least cytotoxicity. In particular, P4 had essentially no cell toxicity up to a concentration of 90 µM. Table 2 presents the IC50 (µM) values of some of the tested peptides. The cytotoxicity index of P4 (114.4±10.2) was reduced most compared to that of MMLT (2.36±0.23), representing about a 50-fold decrease in cytotoxicity. From this point forward, P4 is referred to as linker peptide 1 (LP1) and P2 is referred to as linker peptide 2 (LP2).

TABLE 2

Cytotoxicity of Peptides

| Peptide | IC50 (µM) |
|---|---|
| MMLT | 2.36 ± 0.23 |
| P1 | 0.75 ± 0.04 |
| P2 | 26.56 ± 0.56 |
| P3 | 14.44 ± 0.92 |
| P4 | 114.6 ± 10.2 |
| P5 | 6.41 ± 0.64 |

Example 2

Anchor Peptide Affinity for Lipid Membranes

In order to evaluate whether linker peptide 1 (LP1) and linker peptide 2 (LP2) still retained high affinity on a lipid monolayer of the nanoparticles, surface plasmon resonance (SPR) studies were performed by using Biacore X 100 (Biacore Inc, Piscataway, N.J.). The binding kinetics and affinity of LP1 and LP2 on two type of nanoparticles were studied. One type was perfluorocarbon nanoparticles (e.g., perfluorooctylbromide, PFOB), the other type was oil-based (safflower core) nanoparticles. PBS ($Ca^{2+}$ and $Mg^{2+}$ free) was used as the running buffer. Nanoparticles were immobilized on Biacore sensor chip L1 by injecting nanoparticles at a flow rate of 1 µl/min for 30 minutes, followed by a running buffer wash at a flow rate of 100 µl/min for 50 seconds. Peptides in selected concentrations, prepared in running buffer, were then injected at a flow rate of 30 µl/min for 1 minute. At the end of each experiment, the sensor chip surface was regenerated by injection of 3-[(3-cholamidopropyl)dimethylammonio]-1-propanesulfonate (CHAPS) at a flow rate of 100 µl/min for 24 seconds.

Figure 3:
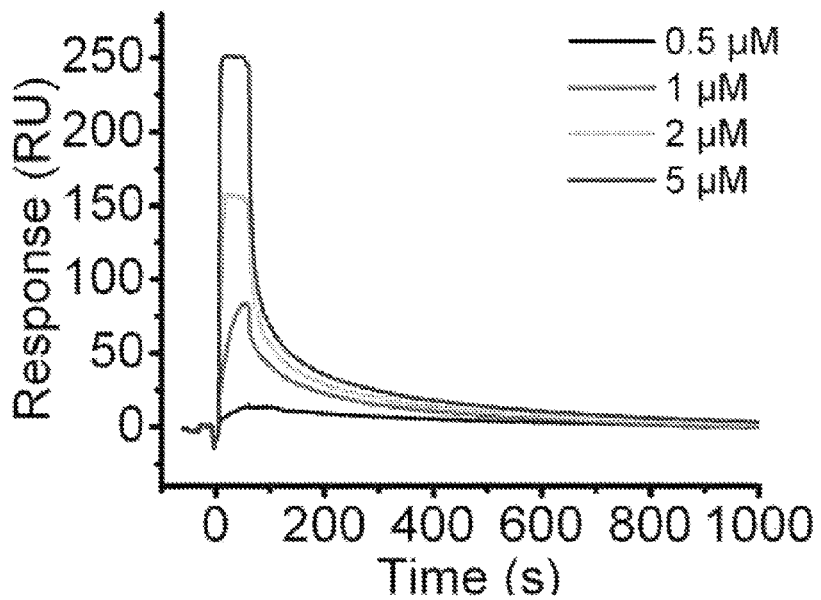
FIG. 3 depicts a series of graphs showing the binding kinetics of linker peptide 1 and linker peptide 2 on perfluorocarbon and oil-based nanoparticles immobilized on Biacore Sensor chip L1. Selected sensorgrams are shown at the indicated concentrations. (A, B) Sensorgrams of linker peptide 1 on perfluorocarbon and oil-based nanoparticles. (C, D) Sensorgrams of linker peptide 2 on perfluorocarbon and oil-based nanoparticles.
Figure 3:
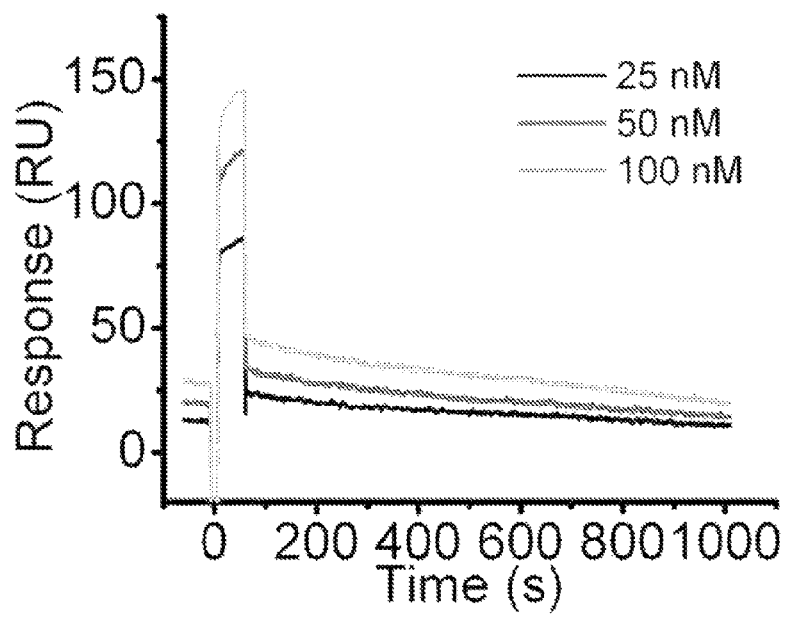
Figure 3:
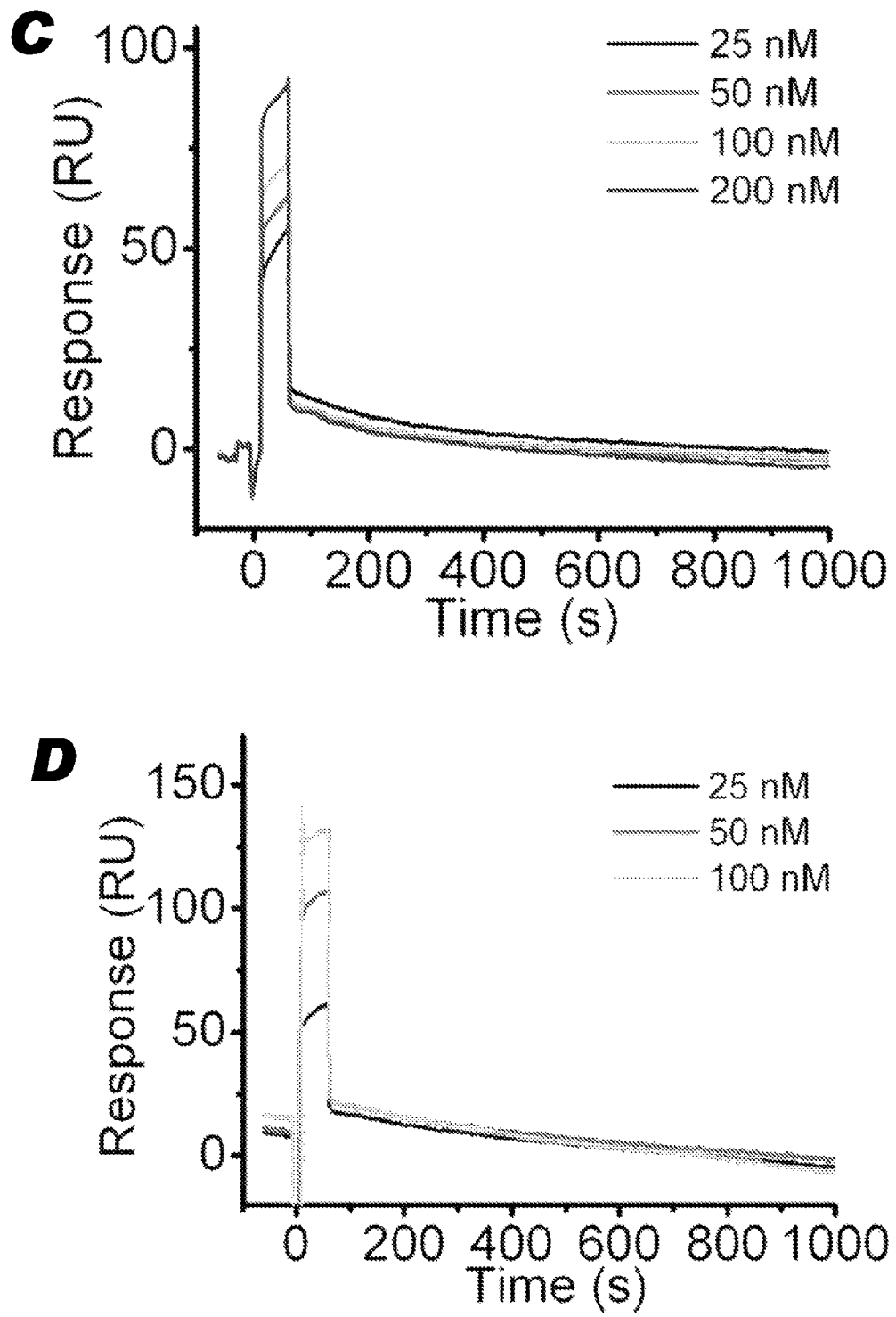

Selected sensorgrams are shown in FIG. 3. The dissociation constants of LP1 and LP2 on perfluorocarbon nanoparticles were $2.25 \times 10^{-7}$ M and $5.48 \times 10^{-9}$ M, respectively. The dissociation constants of linker peptides 1 and 2 on oil-based nanoparticles were $2.29 \times 10^{-8}$ and $6.4 \times 10^{-10}$ M, respectively. These results indicated that both anchor peptides retained high affinity with both perfluorocarbon and oil-based nanoparticles. These results compare with a previously measured dissociation constant for melittin on perfluorocarbon nanoparticles of $1.5 \times 10^{-9}$ M.

Figure 4:
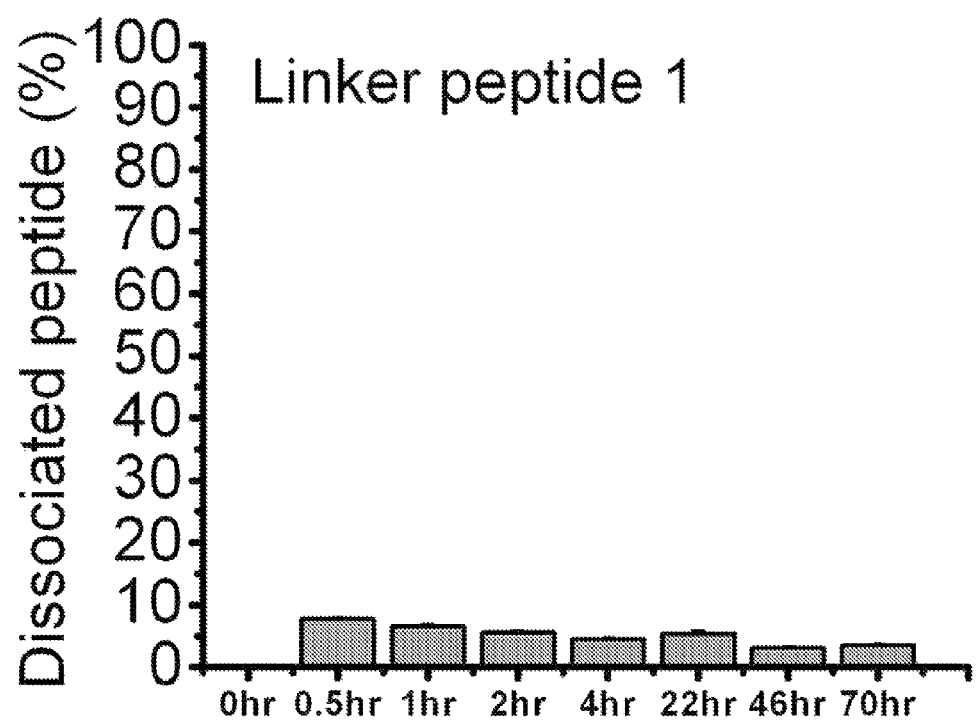
FIG. 4 illustrates dissociation of loaded linker peptide 1 from PFOB nanoparticles at different time points after the loading.

The dissociation of the peptide from linker peptide 1-loaded PFOB nanoparticles is depicted in FIG. 4. After being loaded with the linker peptide 1, the loaded PFOB nanoparticles were stored at 4° C. for 30 minutes, 1 hour, 2 hours, 4 hours, 22 hours, 46 hours, and 70 hours. The loaded nanoparticles were centrifuged at 100 g for 10 minutes, and the dissociated linker peptide 1 was measured by using tryptophan fluorescence after excitation at 280 nm in a fluorescent spectrofluorometer (Varian Inc, Palo Alto, Calif.). The results showed that less 10% of the loaded linker peptide 1 was dissociated from the PFOB nanoparticles for up 70 hours after being loaded. These data suggest that the association between linker peptide 1 and the PFOB nanoparticles was stable.

Figure 5:
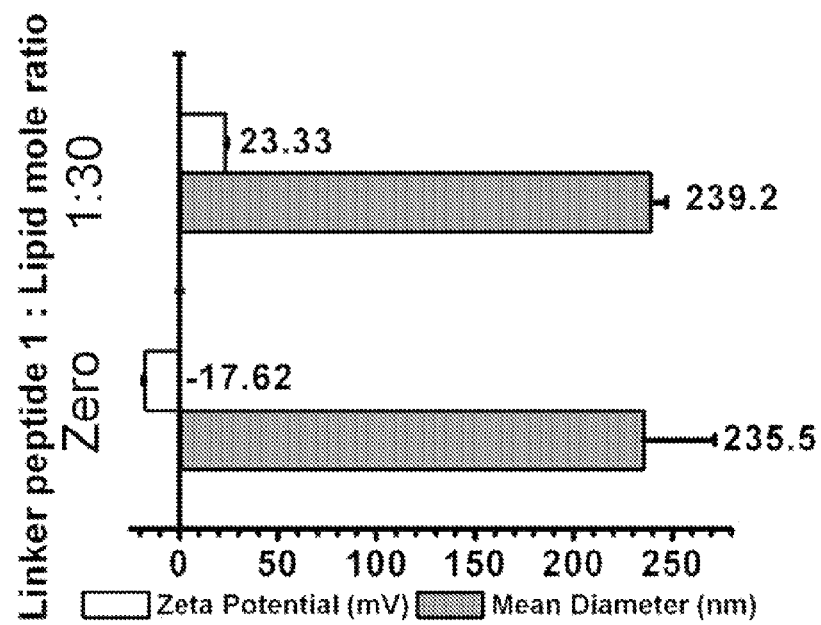
FIG. 5 shows that insertion of the linker peptide 1 into PFOB nanoparticles forms stable peptide-nanoparticle complexes. (A) Presents a plot of the average hydrodynamic diameters and the zeta potentials of PFOB nanoparticles with or without insertion of linker peptide 1. (B) Presents a transmission electron microscopy image of linker peptide 1 inserted PFOB nanoparticles in which the lipid membrane of the PFOB nanoparticles appears intact.
Figure 5:
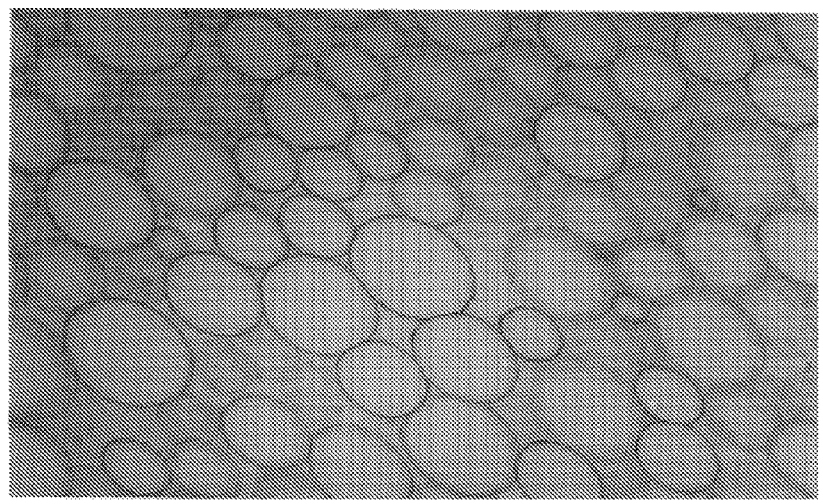

The size distributions of the nanoparticles with or without the linker peptide were analyzed by dynamic light scattering (Brookhaven Instruments Corp., Holtsville, N.Y.). Zeta potential (ζ) values were determined with a Brookhaven Instruments PALS Zeta Potential Analyzer (Brookhaven Instruments Corp., Holtsville, N.Y.). Data were acquired in the phase-analysis light scattering (PALS) mode following solution equilibration at 25° C. FIG. 5A shows that the average hydrodynamic diameter of the PFOB nanoparticles was not affected by linker peptide 1 insertion, and after incorporating the positively charged linker peptide 1, the PFOB nanoparticles exhibited a zeta potential shift from −17.62 mV to +23.33 mV. This change further confirms the insertion of the linker peptide 1 into the PFOB nanoparticles. Furthermore, the structural integrity of linker peptide 1 inserted PFOB nanoparticles was confirmed by transmission electron microscopy. As shown in FIG. 5B, the lipid membrane of the PFOB nanoparticles appears to remain intact.

Figure 6:
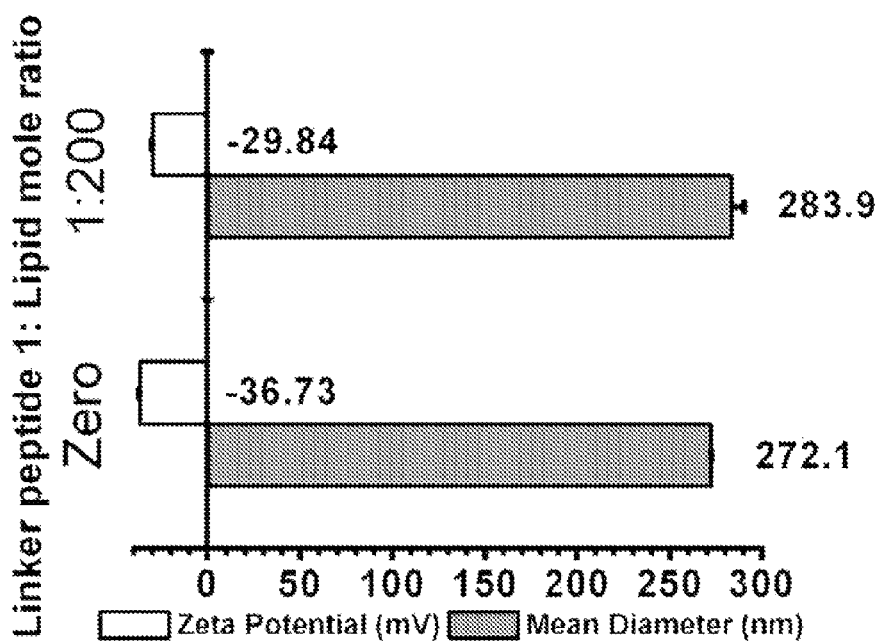
FIG. 6 illustrates that insertion of linker peptide 1 into the liposomes forms stable peptide-liposome complexes. (A) Presents a plot of the average hydrodynamic diameters and the zeta potentials of liposomes with or without insertion of linker peptide 1. (B) Presents a transmission electron microscopy image of linker peptide 1 inserted liposomes in which the lipid membrane of the liposomes appears intact.
Figure 6:
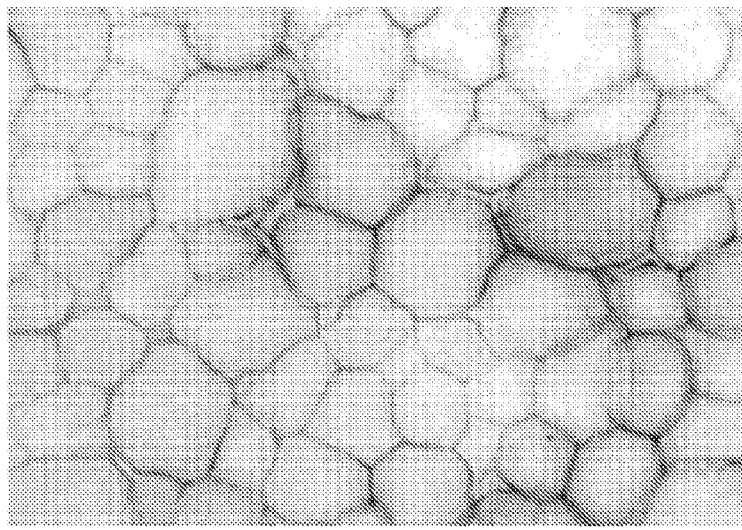

The interactions between linker peptide 1 and liposomes are depicted in FIG. 6. FIG. 6A shows that the average hydrodynamic diameter of the liposomes was not affected by the insertion of linker peptide 1, and after incorporating the positively charged linker peptide 1, the liposomes exhibited a zeta potential shift from −36.73 mV to −29.843 mV. This change further confirms that the linker peptide 1 inserted into the liposomes. Furthermore, transmission electron microscopy of linker peptide 1-loaded liposomes revealed that the lipid membrane of the liposomes appeared intact (FIG. 6B).

Example 3

Cellular Delivery of an Anchor Peptide

The cellular delivery of FITC-labeled peptide 1, incorporated onto perfluorocarbon nanoparticles, was visualized in C-32 melanoma cells by confocal microscopy. PFOB nanoparticles incorporated with FITC labeled linker peptide 1 or plain PFOB nanoparticles were incubated with C-32 melanoma cells in Delta T Culture dish (0.17 mm, Biotech's Inc., Butler, Pa.) at 37° C. for 1 hour, followed by 5 PBS washes. The cells were fixed by incubating in 1 ml of 4% paraformaldehyde at 37° C. for 5 minutes. After the fixation, cells were washed with PBS for 5 times and visualized by using a Zeiss 510 confocal microscope.

As shown in FIG. 7A, the FITC signal was detected both on the cell surface and in the cytoplasm of cells incubated with the linker-loaded nanoparticles. In contrast, cells exposed to plain PFOB nanoparticles displayed no FITC signal (FIG.

7B). These results demonstrate that linker peptide 1 retained the sufficient stability on the lipid monolayer of the nanoparticles for cellular delivery.

Example 4

VCAM-Targeting Anchor Peptide Affinity for Lipid Membranes

To evaluate the function of a cargo complex, two VCAM-targeting peptides were synthesized. For this, an anti-VCAM peptide, VHPKQHR (SEQ ID NO:222), was fused on the N-terminal side or C-terminal side of linker peptide 1 with two glycines as a spacer, as depicted in Table 3.

TABLE 3

VCAM-targeting peptides

| Name | Sequence | SEQ ID NO: |
|------|----------|------------|
| TCP1 | VLTTGLPALISWIKRggVHPKQHR | 223 |
| TCP2 | VHPKQHRggVLTTGLPALISWIKR | 224 |

Figure 8:
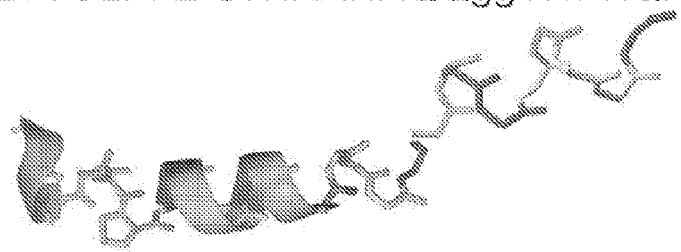
FIG. 8 depicts the binding kinetic of two VCAM-targeting peptides on PFOB nanoparticles immobilized on Biacore Sensor chip L1. (A) The sequence and structure of the VCAM-targeting peptide (TCP1), which is an anti-VCAM peptide fused on the C-terminal of linker peptide 1 with two glycines as a spacer. (B) The sequence and structure of the VCAM-targeting peptide (TCP2), which is an anti-VCAM peptide fused on the N-terminal of linker peptide 1 with two glycines as a spacer. (C) Sensorgram of the VCAM-targeting peptide (TCP1) at the indicated concentrations. (D) Sensorgram of the VCAM-targeting peptide (TCP2) at the indicated concentrations.
Figure 8:
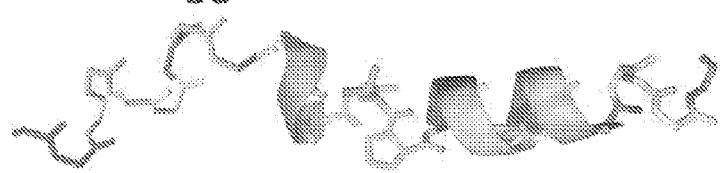
Figure 8:
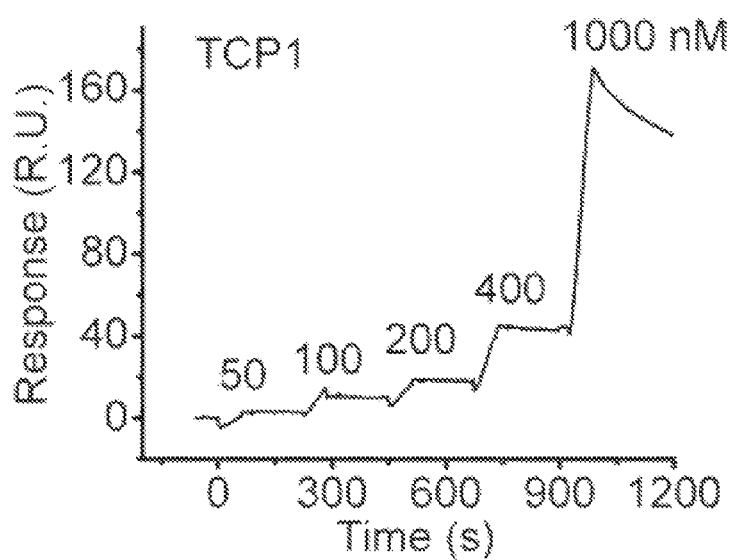
Figure 8D:
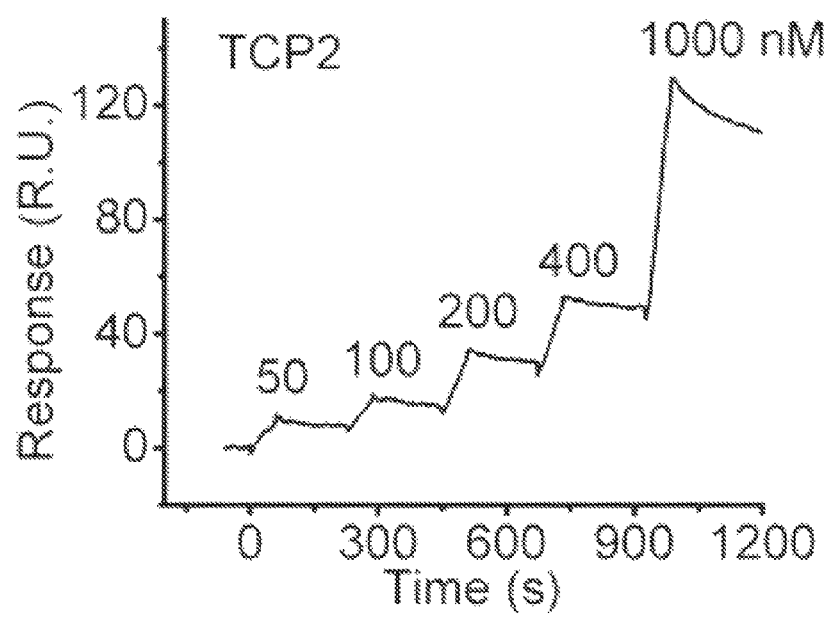

The binding kinetics of the resulting VCAM-targeting peptides (i.e., TCP1 and TCP2) on perfluorocarbon nanoparticles were examined using Biacore X 100. PBS ($Ca^{2+}$ and $Mg^{2+}$ free) was used as the running buffer. Nanoparticles were immobilized on Biacore sensor chip L1 by injecting nanoparticles at a flow rate of 1 µl/min for 30 minutes, followed by a running buffer wash at a flow rate of 100 µl/min for 50 seconds. Targeting peptide prepared at selected concentrations in running buffer was sequentially injected at a flow rate of 30 µl/min for 1 minute. At the end of each experiment, the sensor chip surface was regenerated by injection of 3-[(3-cholamidopropyl)dimethylammonio]-1-propanesulfonate (CHAPS) at a flow rate of 100 µl/min for 24 seconds. FIG. 8 presents selected sensorgrams at several different concentrations of the two VCAM-targeting peptides. The dissociation constant of TCP1 and TCP2 were 0.13 µM and 0.04 µM, respectively. These data suggest that the insertion of linker peptide 1 into PFC nanoparticles was not affected by addition of a targeting ligand cargo.

Figure 9:
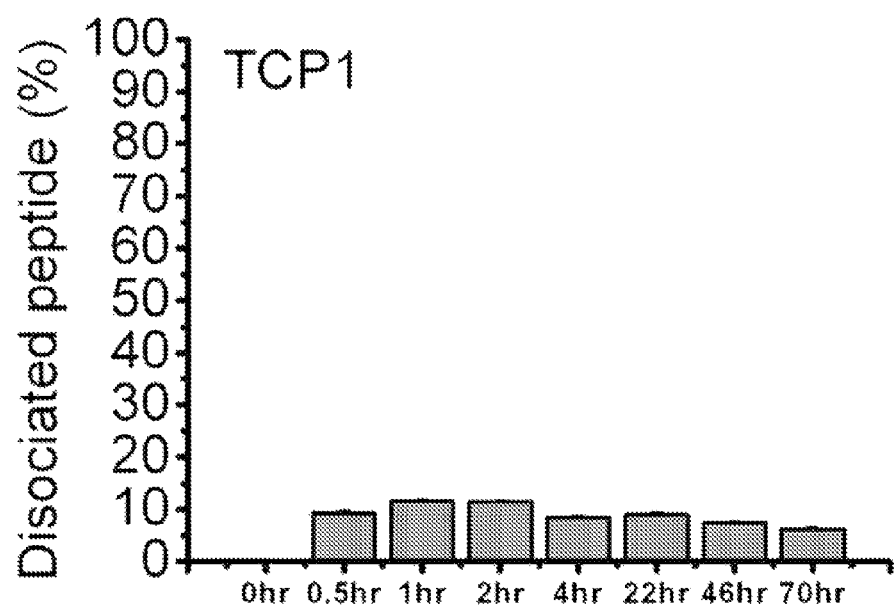
FIG. 9 depicts dissociation of loaded TCP1 (A) or TCP2 (B) from PFOB nanoparticles at different time points after the loading.
Figure 9:
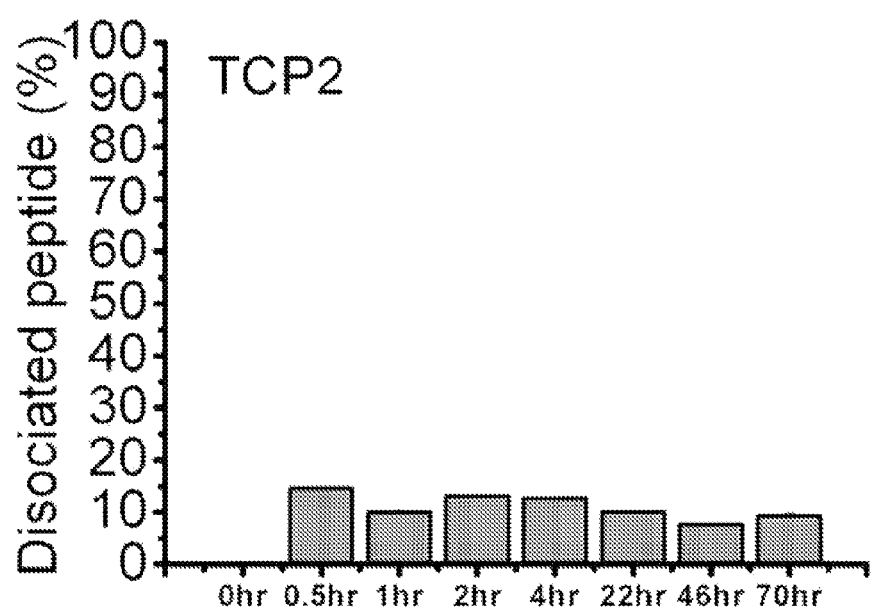

FIG. 9 presents the dissociation of TCP1 or TCP2 from loaded PFOB nanoparticles as a function of time after loading. After loaded with TCP1 or TCP2, the PFOB nanoparticles were stored at 4° C. for 30 minutes, 1 hour, 2 hours, 4 hours, 22 hours, 46 hours, and 70 hours. The stored nanoparticles were then centrifuged at 100 g for 10 minutes and dissociated TCP1 or TCP2 was measured using tryptophan fluorescence after excitation at 280 nm in a fluorescent spectrofluorometer (Varian Inc, Palo Alto, Calif.). The results showed that up to 70 hours after being loaded into the PFOB nanoparticles, less 15% of the loaded TCP1 or TCP2 had dissociated. Furthermore, these data suggest that targeting peptide-loaded PFOB nanoparticles are stable.

Figure 10:
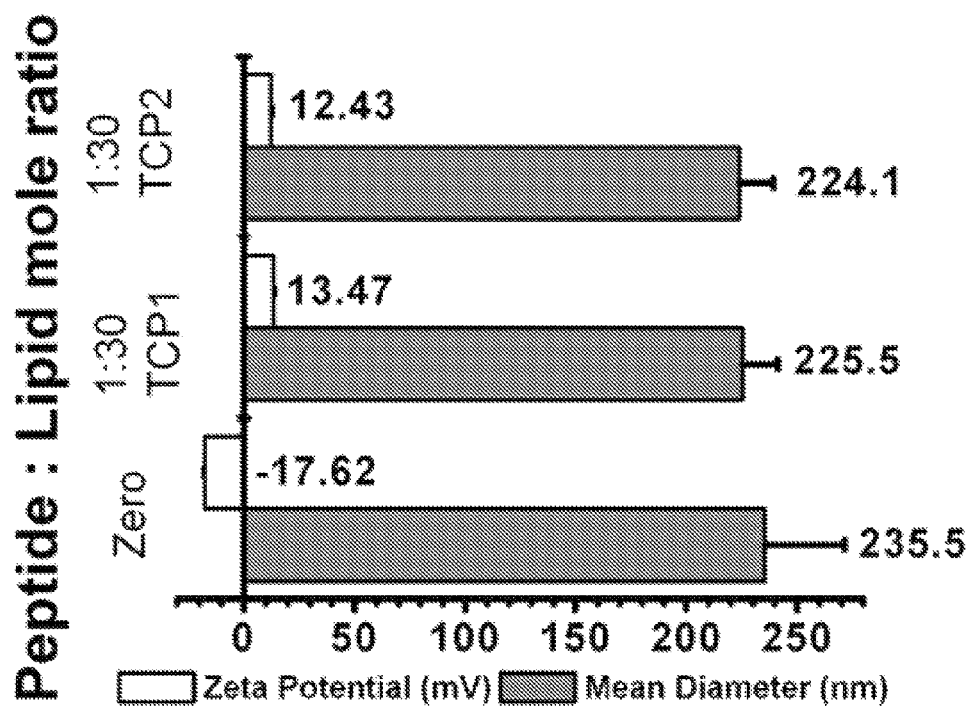
FIG. 10 illustrates that insertion of TCP1 or TCP2 into PFOB nanoparticles forms stable peptide-nanoparticle complexes. The average hydrodynamic diameters and zeta potentials of PFOB nanoparticles with TCP1, TCP2, or no peptide are shown.

The average hydrodynamic diameter of the PFOB nanoparticles was not affected by the insertion of TCP1 and TCP2 (see FIG. 10). Additionally, after incorporation of the positively charged TCP1 or TCP2, the PFOB nanoparticles exhibited a zeta potential shift from −17.62 mV to 13.47 mV or 12.43 mV, respectively. These data further confirm the stable insertion of TCP1 and TCP2 into the PFOB nanoparticles.

Example 5

Specific Targeting Nanoparticles

The specific binding of VCAM targeted nanoparticles was evaluated by confocal microscopy in 2F2B cells, which express VCAM-1 on the cell surface after TNF-α stimulation. Alexa Fluor 488 labeled PFOB nanoparticles comprising the VCAM-targeting peptide (TCP1 or TCP2) or nanoparticles themselves were incubated with TNF-α stimulated 2F2B cells in Delta T Culture dish at 37° C. for 1 hour, followed by five PBS washes. Cells were then fixed by incubation in 1 ml of 4% paraformaldehyde at 37° C. for 5 minutes. After fixation, the cells were washed with PBS for 5 times and the cells were visualized using a confocal microscope (Zeiss Meta 510, Thornwood, N.Y.) with standard filter sets. Concomitant differential interference contrast (DIC) imaging was used to determine the location of nanoparticles in the cells.

Manifestly stronger fluorescent signals emanated from the cells treated with VCAM-targeted nanoparticles (FIGS. 11A and 11B) than from cells treated with nontargeted nanoparticles (FIG. 11C), which demonstrates the specific binding of targeted nanoparticles to cellular VCAM-1. It is also clear that the exposure of VCAM-1 targeting peptides fused on the C-terminus of the linker (i.e., TCP1) exhibited better binding (FIG. 11A) than when VCAM-1 targeting peptide is attached to the N-terminus (i.e., TCP2) of the linker (FIG. 11B). These findings conform to the known orientation of melittin in membranes where the N-terminus situates more deeply into the lipid membrane and the C-terminus remains exposed on the surface.

Two formulations of VCAM-1-Targeted NanoParticles (VTNP) were prepared by using the anchor peptide strategy. The first formulation of VCAM-1-Targeted NanoParticles (VTNP1) was produced by mixing pre-formulated PFC nanoparticles with TCP1. The second formulation (VTNP2) was produced by mixing pre-formulated PFC nanoparticles with TCP2. All nanoparticles had a perfluoro-15-crown 5-ether (CE) core. VTNP1 or VTNP2 were generated by addition of 100 nmol of TCP1 or TCP2 on 20 µl CE nanoparticles, respectively.

Figure 12:
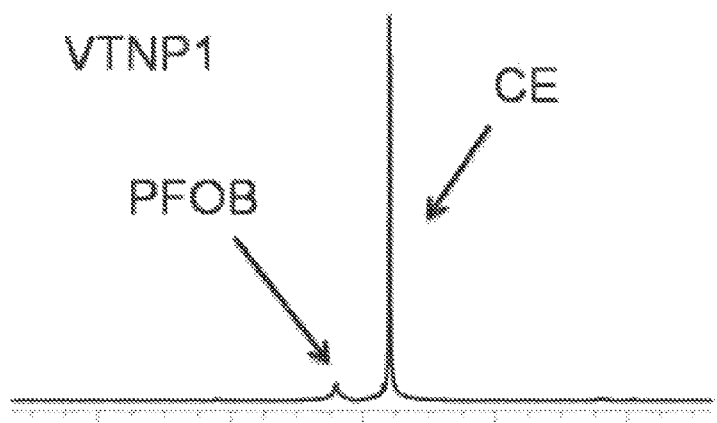
FIG. 12 depicts functional importance of specific linker-cargo conjugation site. (A-C) Representative $^{19}$F MR spectra of 2F2B endothelial cells treated with VTNP1, VTNP2, or non-targeted PFC nanoparticles, respectively. (D) Quantification of specific delivery of VTNP1, VTNP2, and non-targeted nanoparticles (NP) to 2F2B cells calculated from $^{19}$F MR spectra. VTNP1 or VTNP2 were generated with addition of 100 nmol of TCP1 or TCP2 on 20 μl CE nanoparticles, respectively. Data are mean±STD (n=6). (E) Dose-dependent comparison between VTNP1 and VTNP2 at selected peptide loadings into 20 μl CE nanoparticles. X-axis represented the amount peptide; Y-axis represented the number of nanoparticles delivered to one 2F2B endothelial cell. A log scale was used. (F) Fluorine magnetic resonance image overlayed onto proton images of cell pellets in test tubes, acquired from cells treated with VTNP2, NP, or VTNP1, from top to bottom. The $^{19}$F signal (bright pellet) was apparent only in the cells treated with VTNP1.
Figure 12:
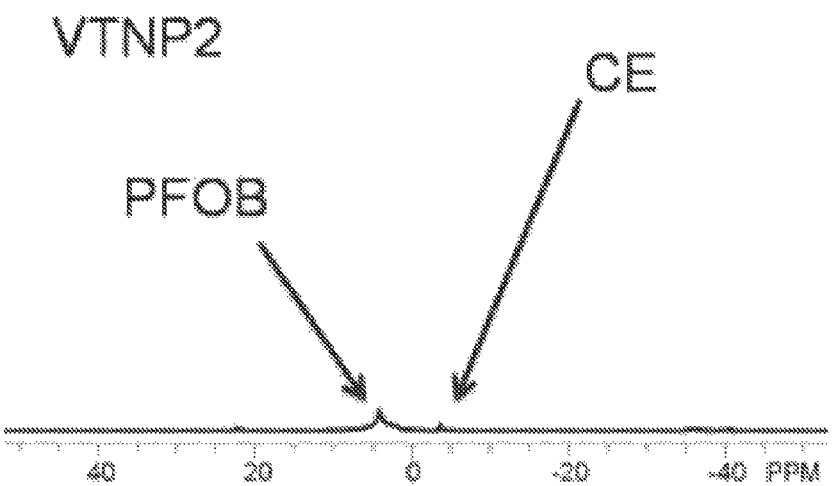
Figure 12:
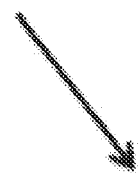
Figure 12:
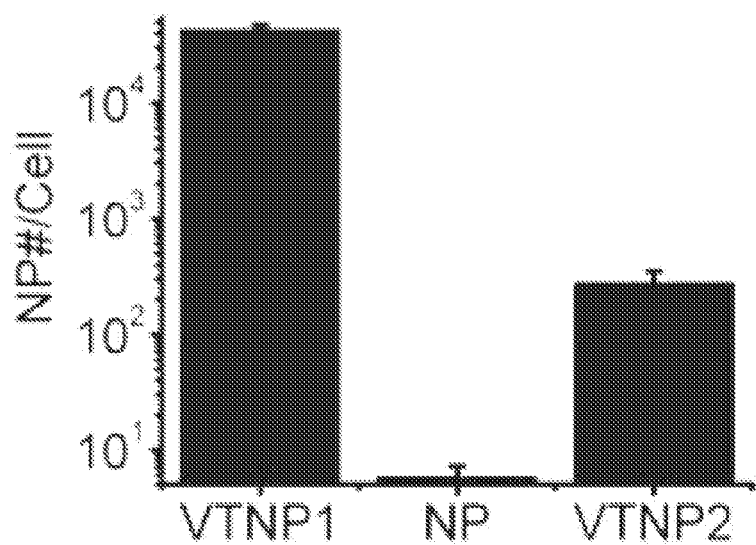
Figure 12:
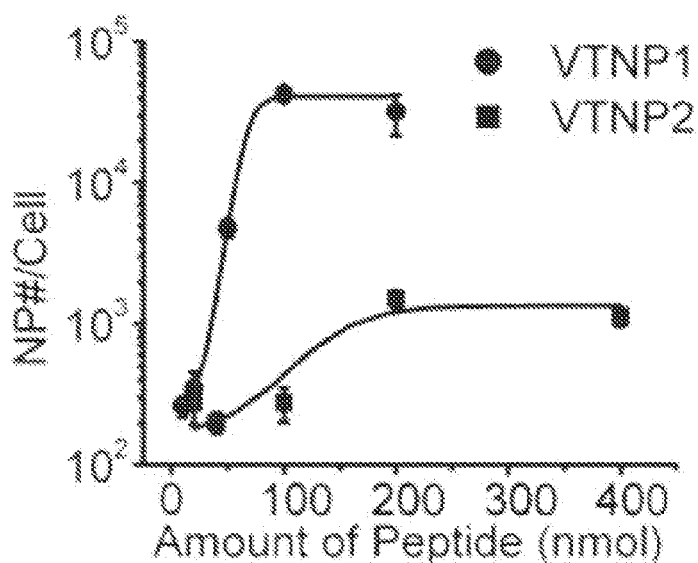
Figure 12:
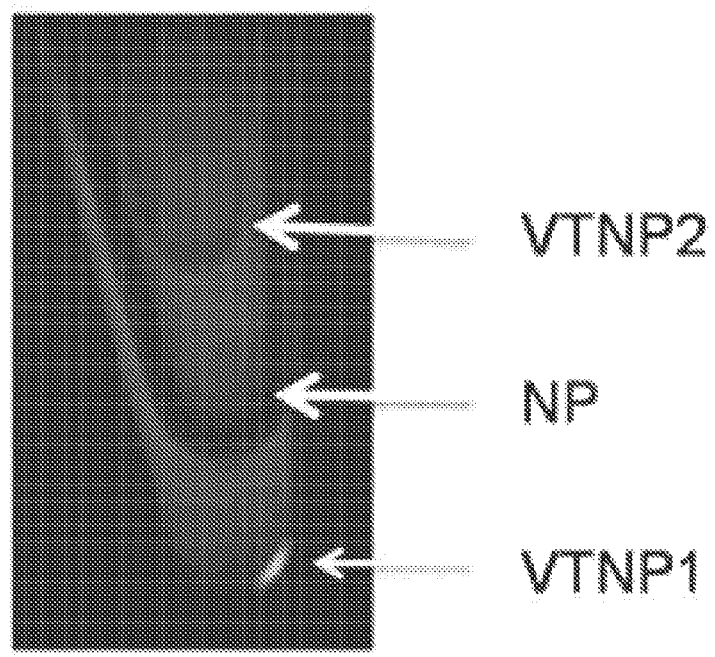

The $^{19}F$ perfluorocarbon core of PFC nanoparticles enabled these nanoparticles to serve as unique magnetic resonance spectroscopic and imaging agents with no background signal in vivo. Furthermore, the $^{19}F$ spectroscopic signature offered the potential for quantification of VCAM-1 biomarkers by providing a rough estimate of the number of delivered nanoparticles per cell. Using this approach, $^{19}F$ MR spectra of TNF-α stimulated 2F2B endothelial cells treated with VTNP1 (FIG. 12A), VTNP2 (FIG. 12B), and non-targeted (FIG. 12C) CE nanoparticles were acquired. Because of linear relation between $^{19}F$ signal intensity and the concentration of $^{19}F$ molecules, the amount of nanoparticles delivered to the cell could be estimated. The number of bound nanoparticles was normalized by the total number of measured cells to calculate the number of the bound nanoparticles per cell (FIG. 12D). These data further support the specific binding of targeted nanoparticles, and also confirmed that VTNP1 manifests better targeting efficiency than does VTNP2. Essentially then, the VTNP2 construct serves as a control scrambled peptide against the more specific VTNP1 sequence.

The dose dependency of targeting for VTNP1 and VTNP2 in selected concentrations was also evaluated in vitro. FIG.

12E again confirms the better targeting efficiency of VTNP1, while also demonstrating that the binding of VCAM-targeted nanoparticles was dependent upon the amount of targeting peptide incorporated onto the nanoparticle. Therefore, optimization of specific targeting might be achieved by adjusting the volume ratio of peptides and PFC nanoparticles. As expected the $^{19}$F image of the cells treated with VTNP1, VTNP2, or non-targeted nanoparticles showed the same preference for C-terminus addition of the targeting sequence (FIG. 12F). A stronger $^{19}$F signal was detected from the cells treated with VTNP1 than with VTNP2, whereas no $^{19}$F signal was detected from the cells treated with non-targeted nanoparticles.

Example 6

Cellular Response to VCAM-1-Targeted Nanoparticles

Figure 13:
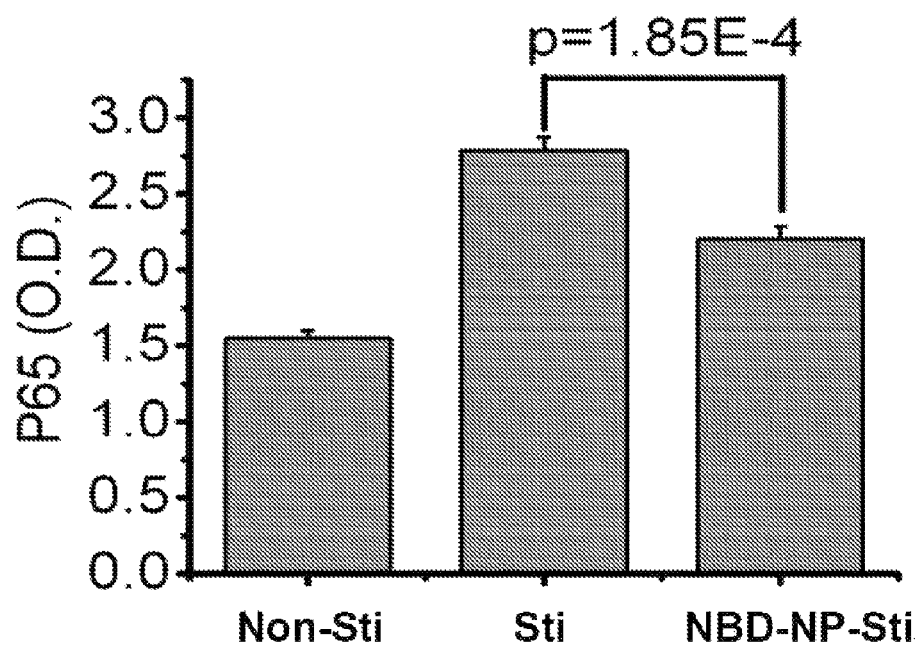
FIG. 13 illustrates that treatment with NBD loaded PFOB nanoparticles partially inhibit NF-kB activation. Plotted is the amount of p65 translocated into the nucleus without TNF-α stimulation (Non-Sti), after TNF-α stimulation for 4 hours (Sti), and after 1 hour pretreatment with VCAM-1 targeted NBD-loaded PFOB nanoparticles followed by TNF-α stimulation (NBD-NP-Sti).

Downstream signaling events were examined in cells exposed to VCAM-1-targeted nanoparticles. In particular, the inhibition of NF-kB activation was examined (see FIG. 13). Without TNF-α (10 ng/ml) stimulation, 2F2B cells had a baseline level of p65 translocated into the nuclear (Non-Sti). After the TNF-α (10 ng/ml) stimulation for 4 hours, NF-kB signaling pathway was upregulated, therefore, and more p65 translocated into the nucleus (Sti). After 1 hour pretreatment with VCAM-1 targeted NBD-loaded PFOB nanoparticles, 2F2B cells had statistically significant less nuclear translocation of p65 (NBD-NP-Sti) than 2F2B cells not pretreated with the VCAM-1 targeted nanoparticles.

Figure 14A:
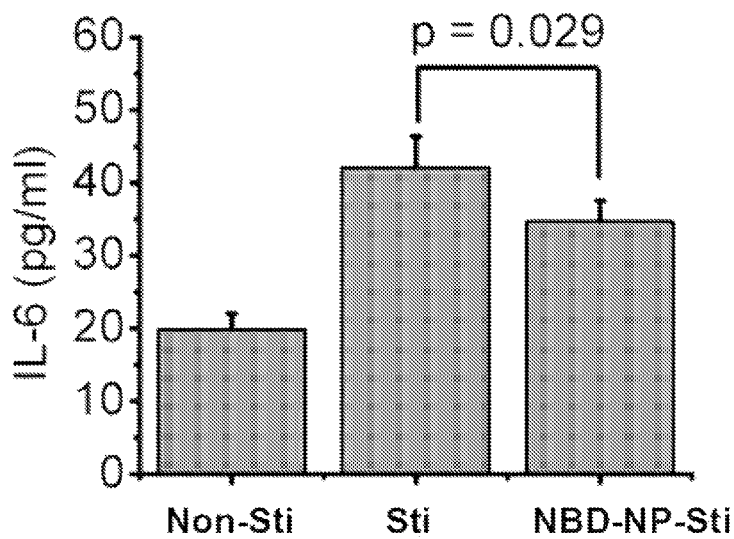
FIG. 14 depicts that treatment with NBD loaded PFOB nanoparticles decreases the expression of NF-kB dependent gene. (A) Plotted is the amount of IL-6 expressed without TNF-α stimulation (Non-Sti), after TNF-α stimulation for 4 hours (Sti), and after 1 hour pretreatment with VCAM-1 targeted NBD-loaded PFOB nanoparticles followed by TNF-α stimulation (NBD-NP-Sti). (B) Shown are micrographs of VCAM-1 expression on the cell membrane in the absence of TNF-α stimulation (Non-Sti), after TNF-α stimulation for 4 hours (Sti), and after 1 hour pretreatment with VCAM-1 targeted NBD-loaded PFOB nanoparticles followed by TNF-α stimulation (NBD-NP-Sti). VCAM-1 expression was detected with a FITC conjugated secondary antibody. Nuclei were stained with DAPI.
Figure 14B:
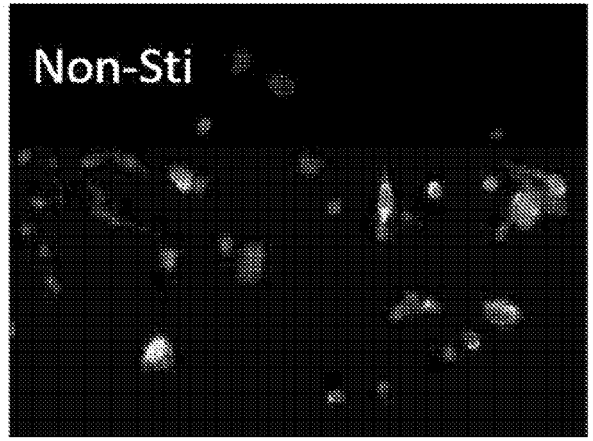
Figure 14B:
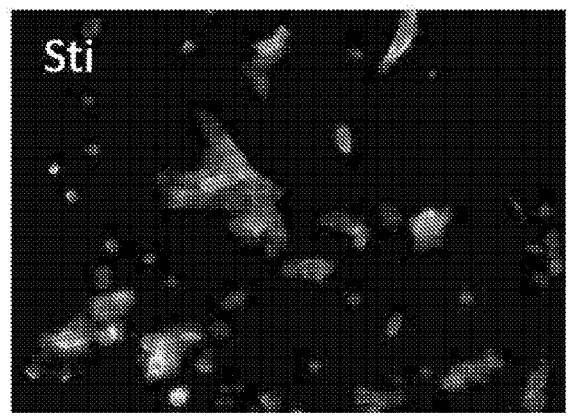
Figure 14B:
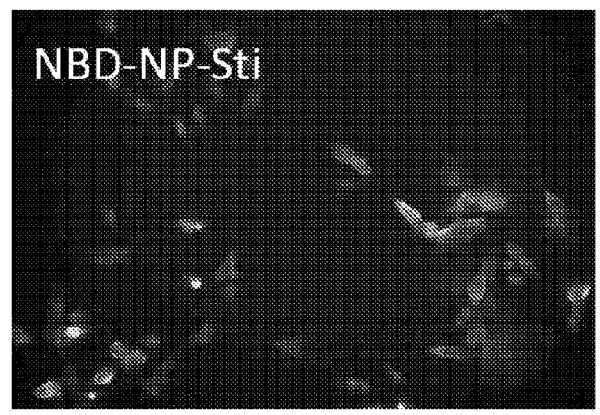

Cells treated with VCAM-1 targeted nanoparticles had decreased expression of a NF-kB dependent gene (see FIG. 14A). 2F2B cells produced a basal level of IL-6 in the absence of TNF-α stimulation (Non-stim). After TNF-α stimulation, the level of IL-6 increased (Sti). After 1 hour pretreatment with VCAM-1 targeted NBD-loaded PFOB nanoparticles, 2F2B cells produced statistically significant less IL-6 (NBD-NP-Sti) than the 2F2B cells that were not exposed to the nanoparticles. As shown in FIG. 14B, VCAM-1 expression on the cell membrane was also down regulated in the 2F2B cells after 1 hour pretreatment with VCAM-1 targeted NBD-loaded nanoparticles (NBD-NP-Sti), as compared to the 2F2B cells that were not pretreated with the nanoparticles (Sti).

Example 7

Cell Labeling

The linker peptide 1 not only can serve as an anchoring agent for synthesized nanoscale particles, but also it can be used for labeling cells. FITC-conjugated linker peptide 1 was incubated with human red blood cells for 1 hour, and a fluorescence image (FIG. 15A) and light image (FIG. 15B) were taken after washing. The green signal in fluorescence image indicates that linker peptide 1 may be used for cell labeling.

Example 8

Inhibition of NF-κB

NF-κB plays an essential role in the initiation and development of cancer and other chronic inflammatory diseases, by regulating a variety of genes that control inflammation, innate and adaptive immune response, cell cycle, and apoptosis [1-4]. As a mediator of oncogenic transformation, NF-κB is a well recognized target for anticancer treatment [5-7]. Also, NF-κB is required for proper immune cell function and, if depleted, can lead to inadequate surveillance against noxious agents and cancer [8]. Among signaling pathway inhibitors, peptide drugs represent a class of attractive therapeutic agents, because of their high specificity, affinity, activity, and low toxicity [9, 10]. However, because of inadequate delivery approaches, rapid proteolytic inactivation and poor bioavailability have limited clinic applications of peptide drugs [10].

One such peptide candidate for NF-κB inhibition is the Nemo Binding Domain (NBD) inhibitory peptide that has been shown to control the signaling events that release NF-κB from the cytoplasmic compartment to translocate to the nucleus and stimulate inflammatory responses [11]. We sought to develop a nanoparticle-based peptide therapeutic approach to the delivery of agents that would inhibit NF-κB but not result in complete suppression, instead eliciting a metered response that could be monitored and adjusted as needed depending on the condition being treated.

Materials and Methods

Nanoparticle and Alexa Fluor 488 Labeled Peptide Synthesis

Perfluorocarbon (PFC) nanoparticle emulsions were formulated using methods described previously [18]. Briefly, a lipid/surfactant co-mixture of 99 mol % egg lecithin and 1 mol % dipalmitoyl-phosphatidylethanolamine, DPPE (Avanti Polar Lipids, Piscataway, N.J.) was dissolved in methanol:chloroform (1:3 in volume). Solvent was evaporated under reduced pressure to produce a lipid film, which was dried in a 50° C. vacuum oven overnight to obtain the surfactant. Then the surfactant (2.0%, w/v), perfluorooctylbromide (PFOB) (Gateway Specialty Chemicals, St Peters, Mo.)(20%, w/v), and distilled, deionized water were blended and emulsified at 20,000 PSI for four minutes in an ice bath (S110 Microfluidics emulsifier, Microfluidics, Newton, Mass.). For fluorescent nanoparticles, Alexa Fluor 488 was incorporated into the surfactant layer. To incorporate NBD peptide (TALDWSWLQTE) or mutant NBD (mutNBD) peptide (TALDASALQTE) [11] into the PFC nanoparticles for protected delivery, we first fused NBD or mutNBD peptide onto the N-terminal of linker peptide (VLTTGLPAL-ISWIKRKRQQ) [17] with two glycines added as a spacer. These combination peptides, "NBD-linker" and "mutNBD-linker", were synthesized by GenScript Co. (Piscataway, N.J.). Conjugation of Alexa Flour 488 to the peptide NBD-Linker was carried out in solution. The TFP ester (2,3,5,6-tetrafluorophenyl) (Sigma, St. Louis, Mo.) of the dye was chosen for the labeling reaction since the TFP ester moiety is more stable in solution compared to the commonly used succinimidyl ester. The methodology for the labeling reaction is as follows: 5 mg of NBD-Linker was dissolved in 0.1 M of sodium bicarbonate buffer. The pH of the buffer was adjusted close to neutral (~7.3) to increase N-terminus selective labeling of the peptide. The required amount of the dye (1.84 mg, 1.5 equiv) was dissolved in 300 µL of DMF (N,N-Dimethylformamide). While stirring/vortexing the peptide solution, the dye solution was added slowly. The reaction was run in dark overnight. The completion of the reaction was monitored by analyzing an aliquot amount of the reaction mixture by reversed phase HPLC (C18 column, flow rate 0.7 ml/min) in 40 to 60% gradient of Acetonitrile (containing 0.075% TFA)/Water (containing 0.1% TFA). Based on HPLC, the reaction was ~87% complete. The labeled peptide was then purified on preparative HPLC (C18 column) following the same solvent gradient as mentioned above. The pure fractions were then lyophilized to obtain the final pure labeled peptide. Fluorescent labeling was further confirmed by FCS analysis.

Incorporation of NBD-Linker or mutNBD-Linker into PFC Nanoparticles

NBD peptide or mutNBD peptide incorporated nanoparticles were formulated by mixing PFC nanoparticles with known amount of NBD-linker or mutNBD-linker, which was dissolved in MilliQ H2O at 10 mM. 1-4 μl 1 mM or 1-15 μl 10 mM NBD-Linker was added to 30 μl of PFC nanoparticles with mixing. After incubation at 4° C. overnight, the mixture was centrifuged at 100 g for 10 minutes to remove unincorporated peptides. The peptide in the supernatant was quantified by measuring intrinsic tryptophan fluorescence (described below) with a standard curve.

Size Distribution and Zeta Potential of Nanoparticles

The size distributions of the nanoparticles with or without cargo incorporated were analyzed by dynamic light scattering (Brookhaven Instruments Corp., Holtsville, N.Y.). The size distribution was plotted by particle number. Zeta potential (ζ) values were determined with a Brookhaven Instruments PALS Zeta Potential Analyzer (Brookhaven Instruments Corp., Holtsville, N.Y.). Data were acquired in the phase-analysis light scattering (PALS) mode following solution equilibration at 25° C.

Electron Microscopy

NBD-Linker incorporated PFC nanoparticles were depicted by transmission electron microscopy. Procedures have been described in detail previously [19].

Giant Unilamellar Vesicles (GUV) Preparation and Confocal Microscopy

GUVs were prepared by the electroformation method [20] from a lipid mixture containing 99.9 mol % of 1,2-dioleoyl-sn-glycero-3-phosphocholine, DOPC (Avanti Polar Lipids, Piscataway, N.J.) and 0.1 mol % of fluorescent dye DiD (Invitrogen, Molecular Probes, Carlsbad, Calif.). Briefly, chloroform mixture of lipids and dye at 2 mg/ml total lipid concentration was dried on a surface of two parallel platinum electrodes resulting in a creation of a thin lipid film on each electrode. Next, platinum electrodes were immersed into a chamber containing 300 mM sucrose solution and connected to a power generator. Electroformation of GUVs attached to the platinum electrodes was performed at 2.3 V and 10 Hz for 1 hour at room temperature followed by the detachment of GUVs from the platinum electrodes done at 2.3 V, 2 Hz for 30 min. For GUV observation, 50 μl of solution containing GUVs was transferred into a Lab-Tek observation chamber (Fisher Scientific, Pittsburgh, Pa.) containing 450 μl of 10 mM HEPES, pH 7.2, 100 mM KCl and 20 μM of Alexa Fluor 546 (Invitrogen, Molecular Probes, Carlsbad, Calif.). Alexa Fluor 546 dye was used to assess the permeabilization of GUVs in the presence of mellitin with time. Observation of GUVs and confocal microscopy was done on Zeiss LSM 510 microscope (Zeiss, Thornwood, N.Y.).

Fluorescence Correlation Spectroscopy (FCS) [21]

FCS is a quantitative technique, which detects fluorescence intensity fluctuations as fluorescent molecules diffuse through a small observation volume (<1 femtoliter). Statistical analysis of these fluorescence intensity fluctuations allows simultaneous determination of the number of fluorescent species in the system and their mobility.

In our case the observation volume is defined by the focal volume of a laser scanning microscope, while the statistical analysis of the intensity trace is calculated as follows:

$$G(\tau) = \frac{\langle \delta F(t) \cdot \delta F(t+\tau) \rangle}{\langle F(t) \rangle^2} \quad (1)$$

where G is the autocorrelation function, F is the fluorescence intensity as a function of time, τ is the correlation time and the angular brackets refer to time averaging, while $\delta F(t) = F(t) - \langle F(t) \rangle$.

The correlation curve obtained from the experiment is fitted with a mathematical function which describes the fluorescence intensity fluctuations in the observation volume according to Brownian diffusion and it also accounts for the photophysical characteristics of the dye:

$$G_{3D}(\tau) = \frac{1}{N}\left[1 + T(1-T)^{-1}\exp\left(\frac{\tau}{\tau_T}\right)\right]\left(1 + \frac{\tau}{\tau_D}\right)^{-1}\left(1 + \frac{\tau}{\tau_D \cdot S^2}\right)^{-1/2} \quad (2)$$

where N is the average number of fluorescent particles in the observation volume, T is the fraction of fluorophores in the triplet state, $\tau_T$ is the lifetime of the triplet state of the fluorophore, $\tau_D$ is the characteristic diffusion time of the fluorophore, $\omega_0$ the waist radius of the laser focus. The structural parameter $S = \omega_z/\omega_0$ measures the aspect ratio of observation volume which is assumed to have Gaussian shape. The diffusion time $\tau_D$ is related to the diffusion coefficient D through the expression:

$$\tau_D = \omega_0^2/4D \quad (3)$$

The waist of the focus $\omega_0$ was determined by fitting the autocorrelation curve obtained in the same experimental conditions using free Alexa Fluor 488 [22]. In the case of labeled peptide binding to the nanoparticles the correlation curves were analyzed using the two component model as was described previously [23].

Surface Plasmon Resonance

The kinetics of NBD-Linker incorporation into lipid monolayers of PFC nanoparticles was studied by surface plasmon resonance (SPR). SPR detects change in the reflective index of a surface (Biacore-X 100 and carboxymethylated dextran chip L1 from Biacore Inc, Piscataway, N.J.). A uniform lipid monolayer on a L1 chip was created by injecting PFC nanoparticles (3 μl/min) for 30 minutes. Loosely deposited nanoparticles were removed by performing extra washing steps after immobilization to ensure a stable baseline. Complete coverage was confirmed by injecting the bovine serum albumin (1 mg/ml in PBS) at 15 μl/min for 2 minutes. Different peptides in selected concentrations were injected at a flow rate of 30 μl/min for 1 minute. At the end of each experiment the chip was regenerated by two consecutive injections of 3-[(3-cholamidopropyl)dimethylammonio]-1-propanesulfonate, CHAPS (50 μl, 100 μl/min). The data were analyzed with BiaEvaluation software (Biacore Inc, Piscataway, N.J.). A two-state model, [17].

Circular Dichroism Spectroscopy

Jasco J-810 spectropolarimeter (Jasco Inc, Eastern, Md.) was utilized for CD spectra measurements of free NBD-Linker and lipid bound NBD-Linker (lipid-peptide molar ratio was 10:1). Spectra were scanned in a 1 mm path length quartz cuvette in the far-UV range from 190-260 nm at a scan rate of 100 nm/min and all spectra were collected under argon. An average 20 scans was used for all spectra. Buffer used was 10 mM potassium phosphate buffer pH 7.0.

Tryptophan Fluorescence Spectroscopy of NBD-Linker-Nanoparticles

The proximity of NBD-Linker peptides with respect to the core perfluorocarbon structures can be defined by measuring their intrinsic tryptophan fluorescence. NBD-Linker contains three tryptophan residues at position 5, 7, and 25, which are potentially quenchable by the bromine atoms in the core perfluoroctylbromine material if in close proximity. [17] Tryptophan fluorescence emission spectra (300 nm to 500 nm) were measured after excitation at 280 nm in a fluorescent spectrofluorometer (Varian Inc, Palo Alto, Calif.).

Cell Culture

F8 cells (from the Lee Ratner laboratory) were maintained in a humidified atmosphere of 95% air and 5% CO2 in the cell culture medium: RPMI, 10% FBS, 4 mM glutamine, and 100 u penicillin/100 µg/ml strep (WashU Tissue Culture Support Center, St. Louis, Mo.).

Transcription Factor Assays and Akt Expression

Figure 19:
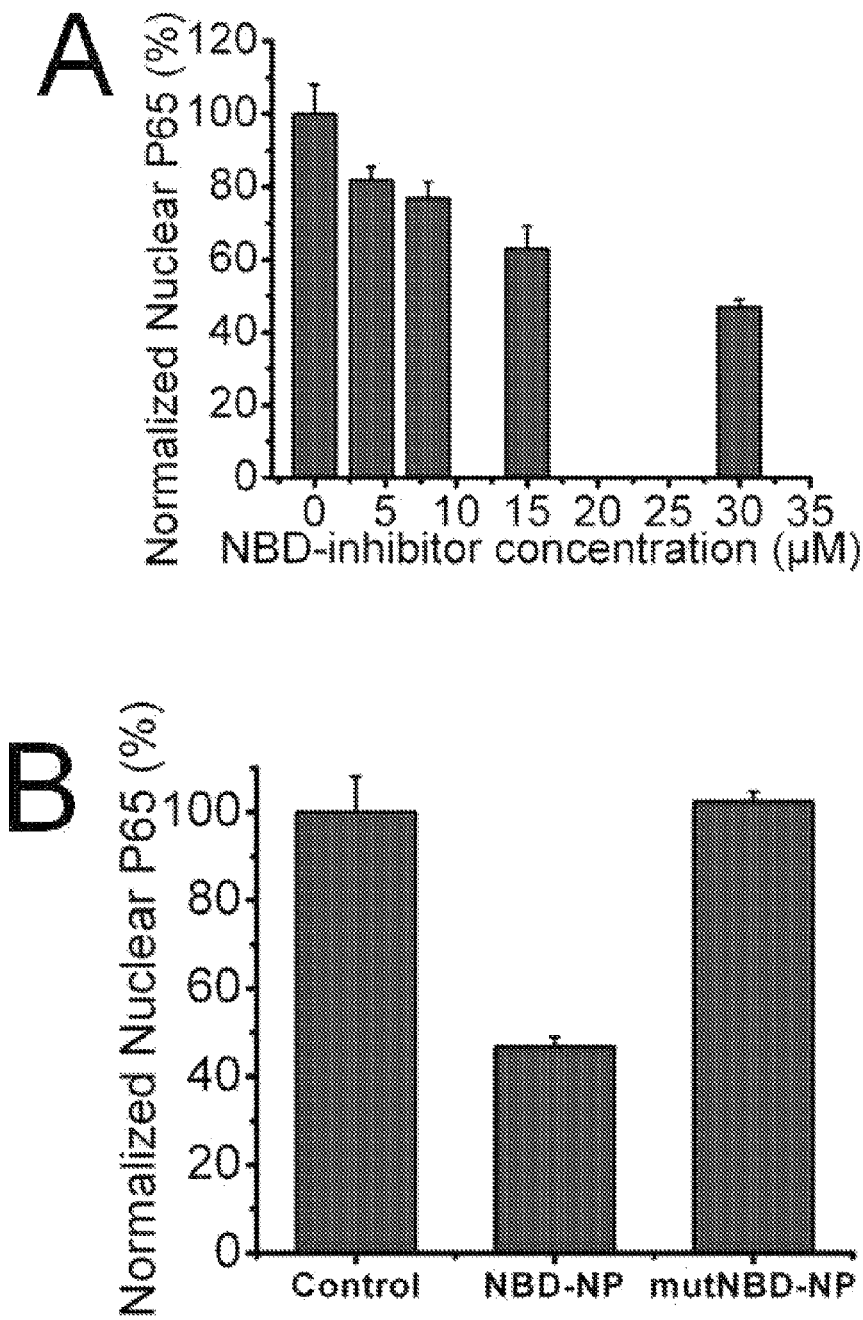
FIG. 19 depicts the inhibition of NF-kB signaling pathway by NBD-Linker incorporated PFC nanoparticles. A. NBD-Linker incorporated PFC nanoparticles inhibit NF-kB protein (P65) translocation into the nucleus in a dose-dependent fashion. Data presented as mean±s.d. (n=3). B. At a concentration of 30 μM, NBD-Linker loaded nanoparticles reduce P65 nuclear translocation by half, but mutNBD-Linker loaded nanoparticles do not inhibit P65 nuclear translocation. C. Expression of NF-kB dependent gene (ICAM-1) was inhibited by NBD-Linker incorporated PFC nanoparticle treatment. The histograms were from one of six sets of independent experiments. Black and grey curves represent ICAM-1 expression with and without treatment for 9.5 hours, respectively. D. Bar graph of mean fluorescence intensity from ICAM 1 stained F8 cells without treatment and with treatment of either NBD-Linker or mutNBD-Linker nanoparticles at concentration of 30 μM. ICAM-1 expression is not significantly affected by mutNBD-Linker nanoparticles. E-F. NBD-Linker incorporated PFC nanoparticles do not affect Akt signaling, an signaling pathway upstream of NF-κB. Total Akt (tAkt) (E) and phosphorylated Akt (pAkt) (F) levels do not differ significantly between F8 cells without or with treatment at selected concentrations. Data presented as mean±STD (n=6)
Figure 19:
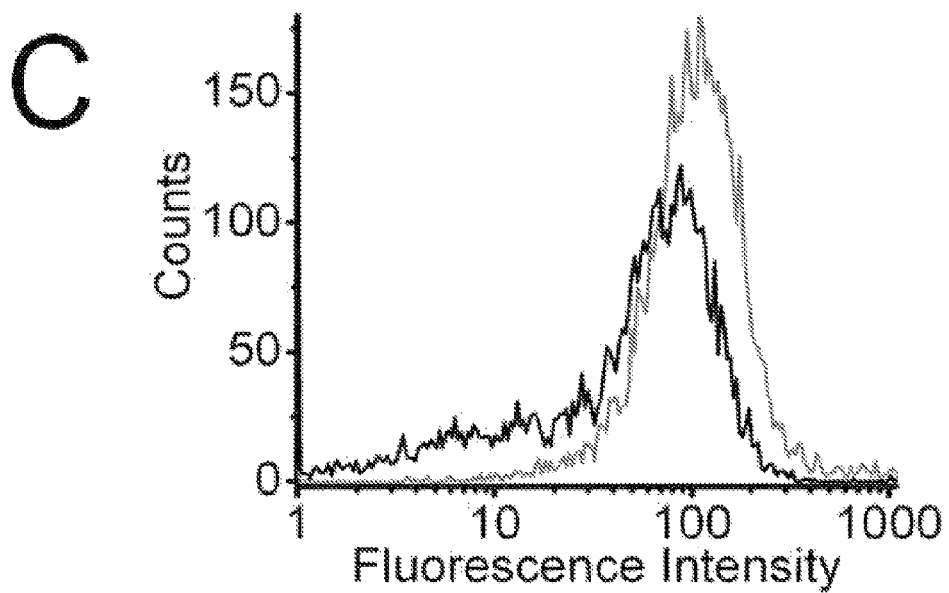
Figure 19:
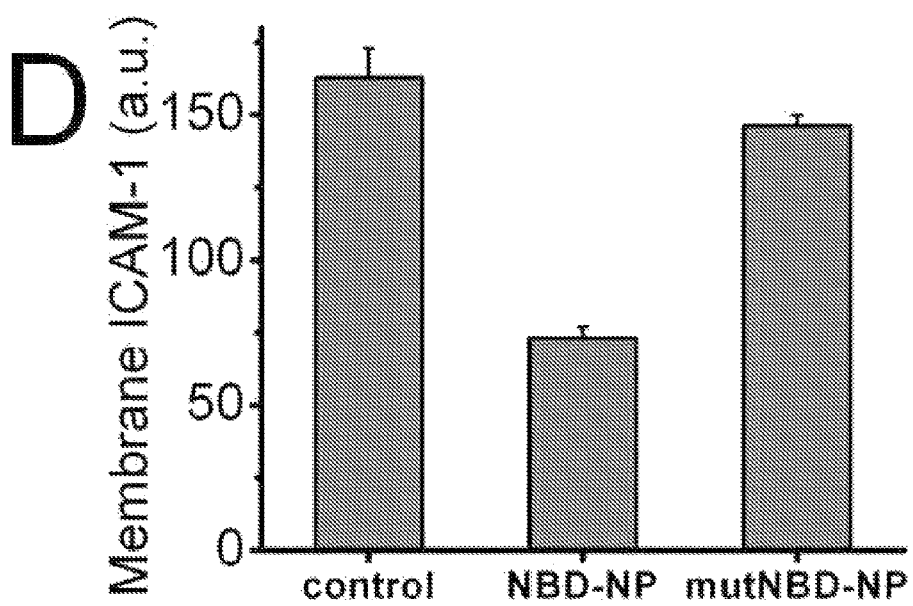
Figure 19:
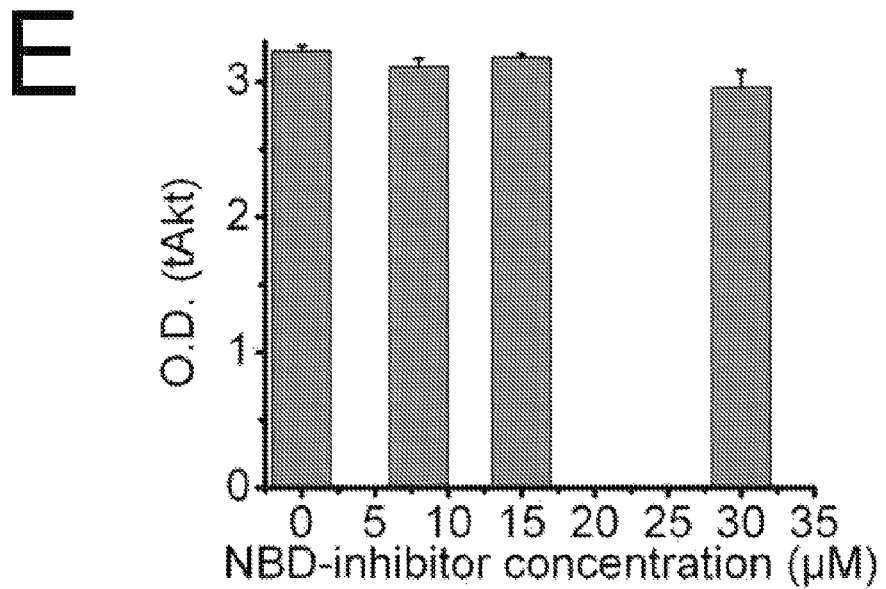
Figure 19:
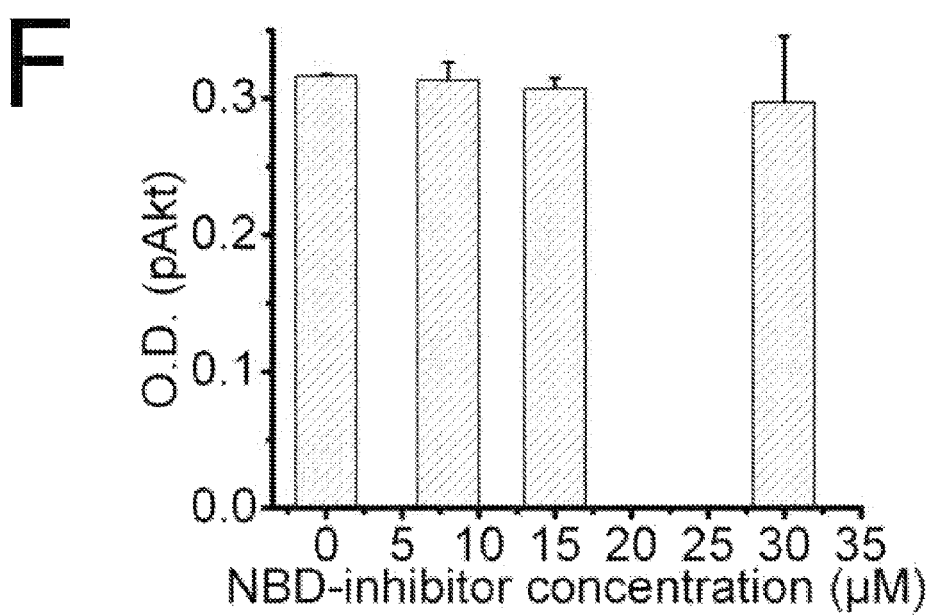

After F8 cells were treated with NBD-Linker or mutNBD-Linker loaded nanoparticles at various concentrations, indicated in the FIG. 19, for 8 hours, cytoplasmic and nuclear proteins were extracted by using a nuclear extract kit (Active Motif, Carlsbad, Calif.) following the manufacturer's instruction. Protein concentrations were determined by the BCA protein assay (Pierce, Rockford, Ill.). Transcription factor assays were perform by using TransAM™ NF-κB p65 Transcription Fact Assay Kit (Active Motif, Carlsbad, Calif.), according to the manufacturer's instruction. Total Akt (tAkt) and phosphorylated Akt (pAkt) expression were evaluated by ELISA (cell signaling technology, Boston, Mass.), according to the manufacturer's instruction.

Flow Cytometry Analysis and Antibodies

After F8 cells were treated with NBD-Linker loaded nanoparticles (30 µM) for 9.5 hours, cells were incubated with FITC Hamster Anti-Mouse CD54 (BD Pharmingen, San Jose, Calif.) and staining buffer (HBSS, 2% FBS, and 1 mM EDTA) for 60 min on ice and then washed before analyzed on flow cytometry (CyAn™ ADP with Summit™ Software, Dako, Carpinteria, Calif.).

Results

Physical Characterization of Peptide-Nanoparticle Constructs

Figure 16:
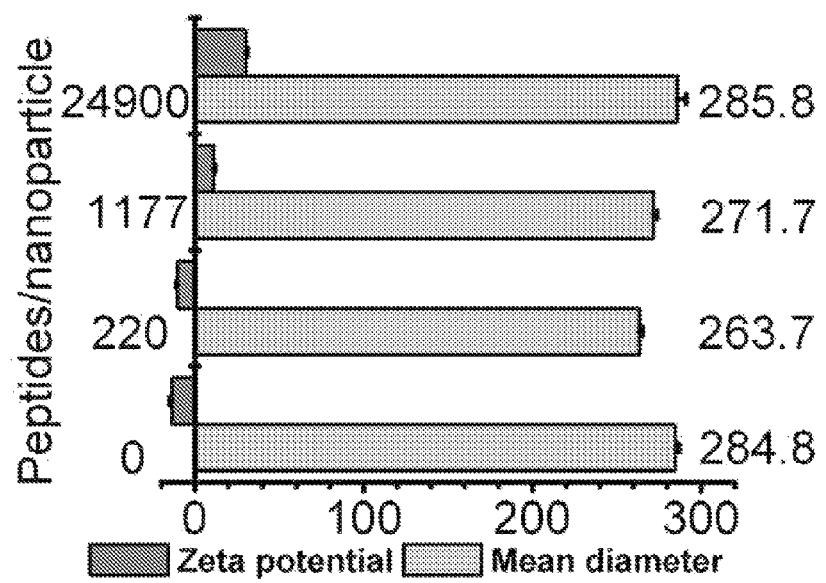
FIG. 16 depicts the characterization of NF-κB inhibiting PFC nanoparticles generated with the use of a linker peptide. (A) Sequence of the NBD peptide conjugated on the N-terminal of the linker peptide (Italic) with two Glycines (SEQ ID NO:225). (B) Mean hydrodynamic diameter and zeta potential of nanoparticles with or without incorporation of NBD-linker, respectively. (C) Transmission electron micrograph of PFC nanoparticles incorporated with NBD-Linker. Scale bar represents 250 nm. (D) A schematic illustration of PFC nanoparticle with enlarged NBD-Linkers incorporated in the lipid monolayer.
Figure 16:
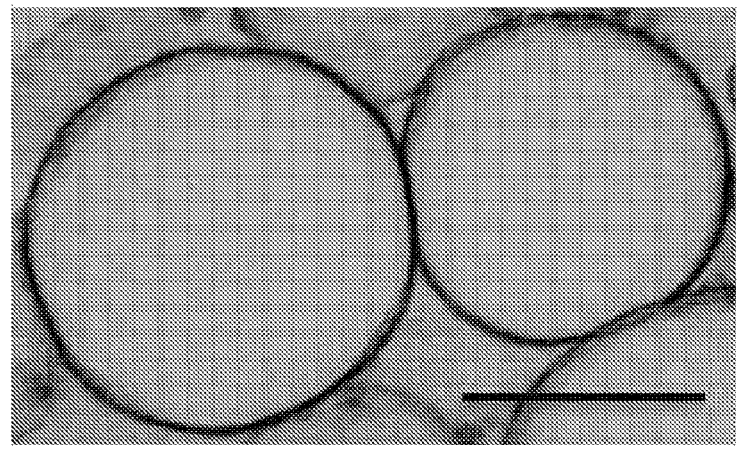
Figure 16:
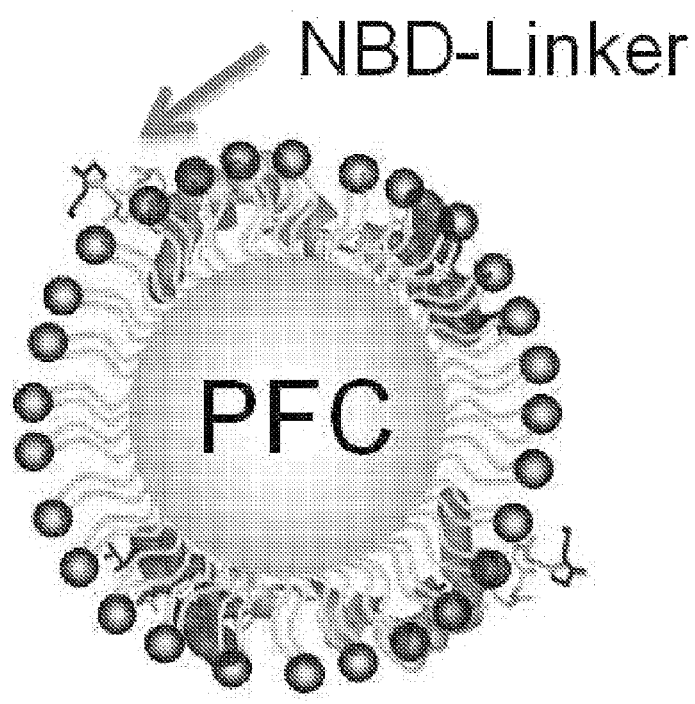

To generate NBD peptide loaded nanoparticles, we produced two discrete components: base PFC nanoparticles as delivery vehicles; and therapeutic NBD peptides fused onto the peptide linker. Base PFC nanoparticles, consisting of hydrophobic core surrounded by a lipid monolayer, are created according to our standard methods of formulation [18]. The NBD peptide is conjugated onto the N-terminal of the peptide linker with two glycines added as a spacer. The sequence of the new peptide (NBD-Linker) is shown in FIG. 16 A. Controlled incorporation of NBD-Linker into PFC nanoparticles is achieved by mixing selected amounts of NBD-Linker with PFC nanoparticles. Free (unloaded) NBD-Linker was removed by gentle centrifugation (10 min@100 g) and measured by tryptophan fluorescence to determine the amount of peptide that was retained on the nanoparticle. By varying the amount of NBD-Linker added to the nanoparticles, copies of NBD-Linker loaded into each nanoparticle ranged between 220 and 24900. The mean diameters of PFC nanoparticles without and with various amount of peptide loading are equivalent (FIG. 16B). The morphology and size of nanoparticles loaded with NBD-linker was also visualized by transmission electron microscopy with lipid membrane staining (FIG. 16C).

Zeta potential represents the surface charge status of nanoparticles. The native PFC nanoparticles exhibit negative zeta potential at −13.74±0.7 mV (FIG. 16 B) due to the negative electron density of the phosphate head groups of the lipid monolayer. The NBD-Linker construct carries 3 net positive charges. Thus, we anticipate that the zeta potential of PFC nanoparticles would shift to more positive values after the peptides are loaded. As shown in FIG. 16B, the more peptide that is loaded, the more positive is the zeta potential on the NBD-Linker loaded PFC nanoparticles. At a loading of 24900 copies of NBD-Linker peptides per nanoparticle, the NBD-Linker loaded PFC nanoparticles exhibit a zeta potential of +30.18±0.52 mV. The zeta potential change confirms the incorporation of NBD-Linker into PFC nanoparticles. The schematic illustration of the structure of the PFC nanoparticle with NBD-Linker incorporation in its lipid membrane is depicted in FIG. 16D.

NBD-Linker Incorporation Into the Lipid Membrane

To visually depict the lipid membrane incorporation of NBD-Linker into generic lipidic structures, we conjugated Alexa Fluor 488 Dye onto the NBD-Linker and mixed them with Giant Unilamellar Vesicles (GUV), which encapsulate a liquid core with a lipid bilayer. The fluorescence from the Alexa Fluor 488 Dye conjugated NBD-Linker (green rings in FIG. 17B) and that from lipophilic-stained (DiD dye) GUV (red rings in FIG. 17A) were co-localized (yellow rings in FIG. 17C). These results illustrate the integration of NBD-Linker into the lipid membrane of GUV.

Figure 17:
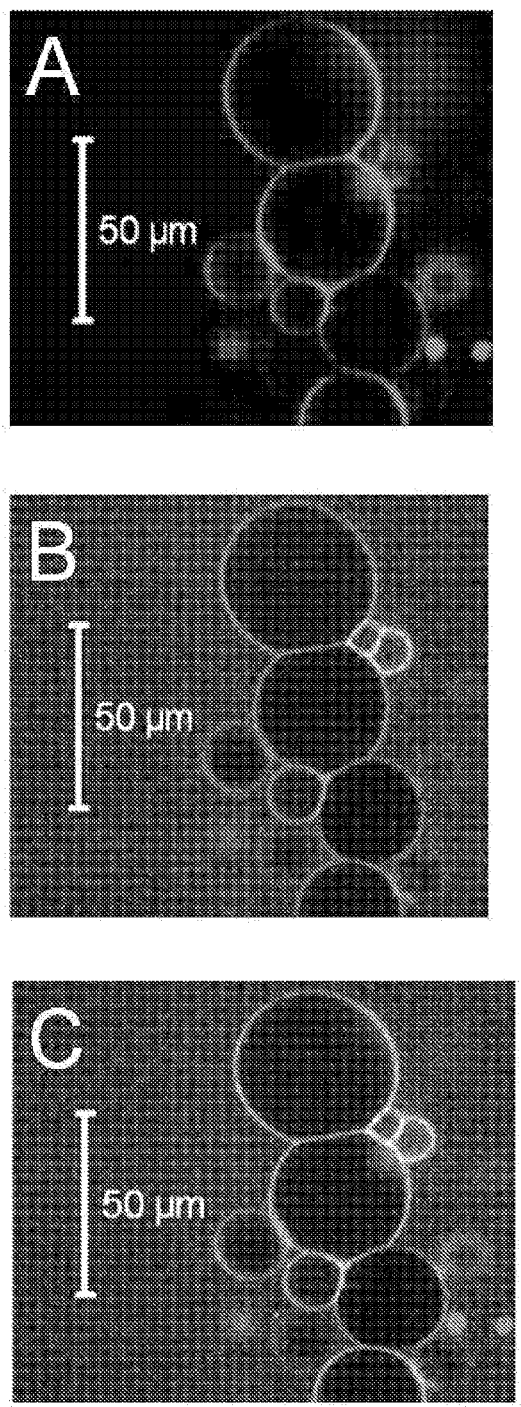
FIG. 17 depicts a visualization of NBD-Linker incorporation into the lipid membrane. A-C. Confocal microscope images show NBD-Linker incorporated onto the lipid membrane of Giant Unilamellar Vesicles (GUV). A. Confocal image of GUV with membrane labeled with lipophilic dye DiD (red rings). B. Confocal image of Alexa Fluor 488 labeled NBD-Linker (green rings). C. Co-localization of Alexa Fluor 488 labeled NBD-Linker and the lipid membrane of GUV (yellow rings). D. Schematic of the FCS observation volume formed by the focused laser beam (~1 femtoliter). E. Normalized auto-correlation curves for Alexa Fluor 488, Alexa Fluor 488 labeled NBD-Linker (NBD-Linker-488), nanoparticles incorporated with labeled peptide (NP-NBD-Linker-488). F. Diffusion time of Alexa Fluor 488, Alexa Fluor 488 labeled NBD-Linker (NBD-Linker-488), nanoparticles incorporated with labeled peptide (NP-NBD-Linker-488), and nanoparticles formulated with Alexa Fluor 488 conjugated lipids. Data presented as mean±STD (n=3).
Figure 17:
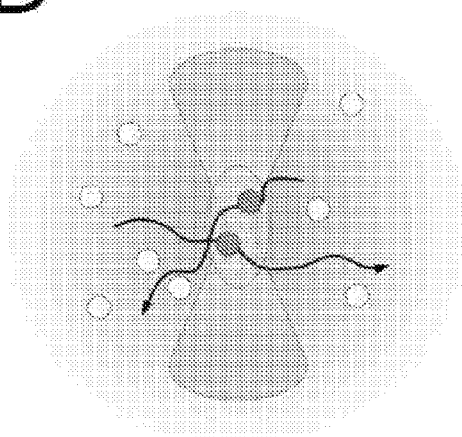
Figure 17:
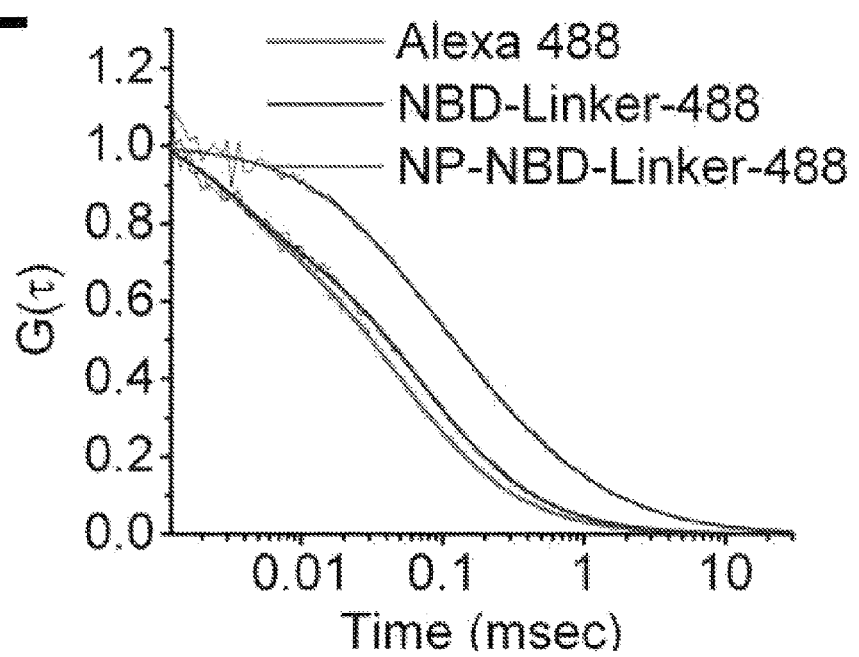
Figure 17F:
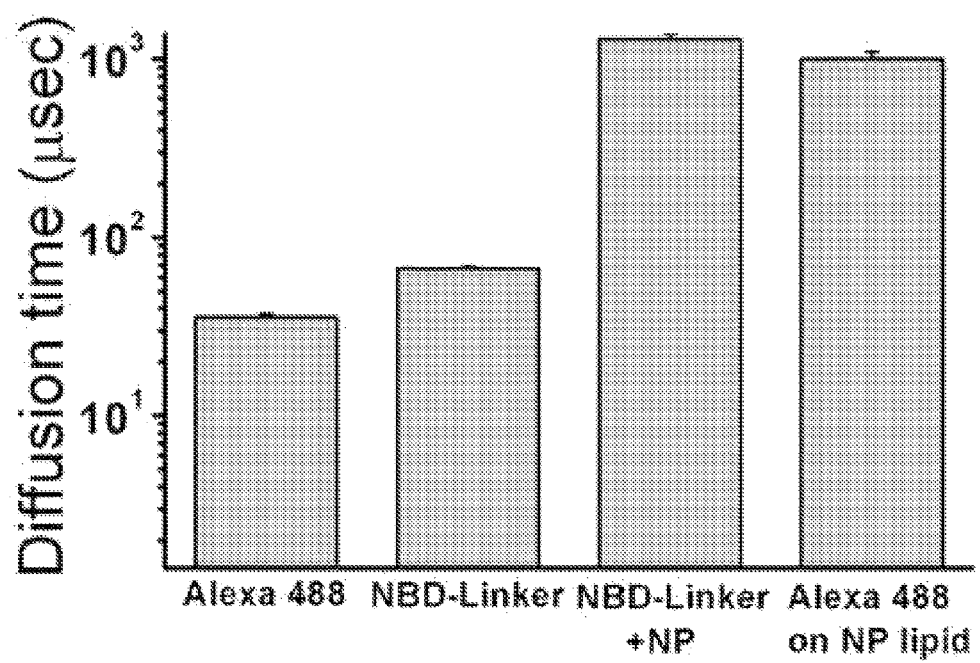

To further illustrate the incorporation of the NBD-Linker into the lipid monolayer of nanoparticles, we employed Fluorescence Correlation Spectroscopy (FCS), which is a single-molecule sensitive fluorescence technique permitting high-accuracy determination of the diffusion coefficients of fluorescently labeled particles in solution [23-25]. The diffusion coefficient of a particle characterizes the mobility of a particle in solution, and it is inversely proportional to the characteristic diffusion time, is directly measured by FCS. represents the average time the particle spends in the FCS detection volume (illustrated as green oval in FIG. 17D) created by a focused laser beam. The longer the FCS diffusion time of a particle, the bulkier it is. By fitting the autocorrelation curve obtained in the experiments, two diffusion time components were detected by FCS analysis from the mixture of Alexa Fluor 488 labeled NDB-Linker and PFC nanoparticles. One component exhibited the same diffusion time as the Alexa Fluor 488 conjugated NBD-Linker, and the other component manifested a comparable diffusion time to that of PFC nanoparticles containing Alexa Fluor 488 conjugated lipid. Normalized autocorrelation curves and the fittings of Alexa Fluor 488, Alexa Fluor 488 labeled NDB-Linker, and Alexa Fluor 488 labeled NDB-Linker plus PFC nanoparticles are shown in FIG. 17E. In addition, analysis of the FCS diffusion times shows that the diffusion time of Alexa Fluor 488 conjugated NBD-Linker (67.2±1.8 µsec) is about two times slower than the diffusion time of the Alexa Fluor 488 (35.8±1.4 µsec). After achieving Alexa Fluor 488 labeled NDB-Linker incorporation, the resultant fluorescent nanoparticles exhibited strikingly longer diffusion times (1300±100 µsec), which is comparable to the diffusion time of the Alexa Fluor 488 lipid labeled nanoparticle (1000±100 µsec), as shown in FIG. 17F.

Mechanism of NBD-Linker and PFC Interaction

Figure 18:
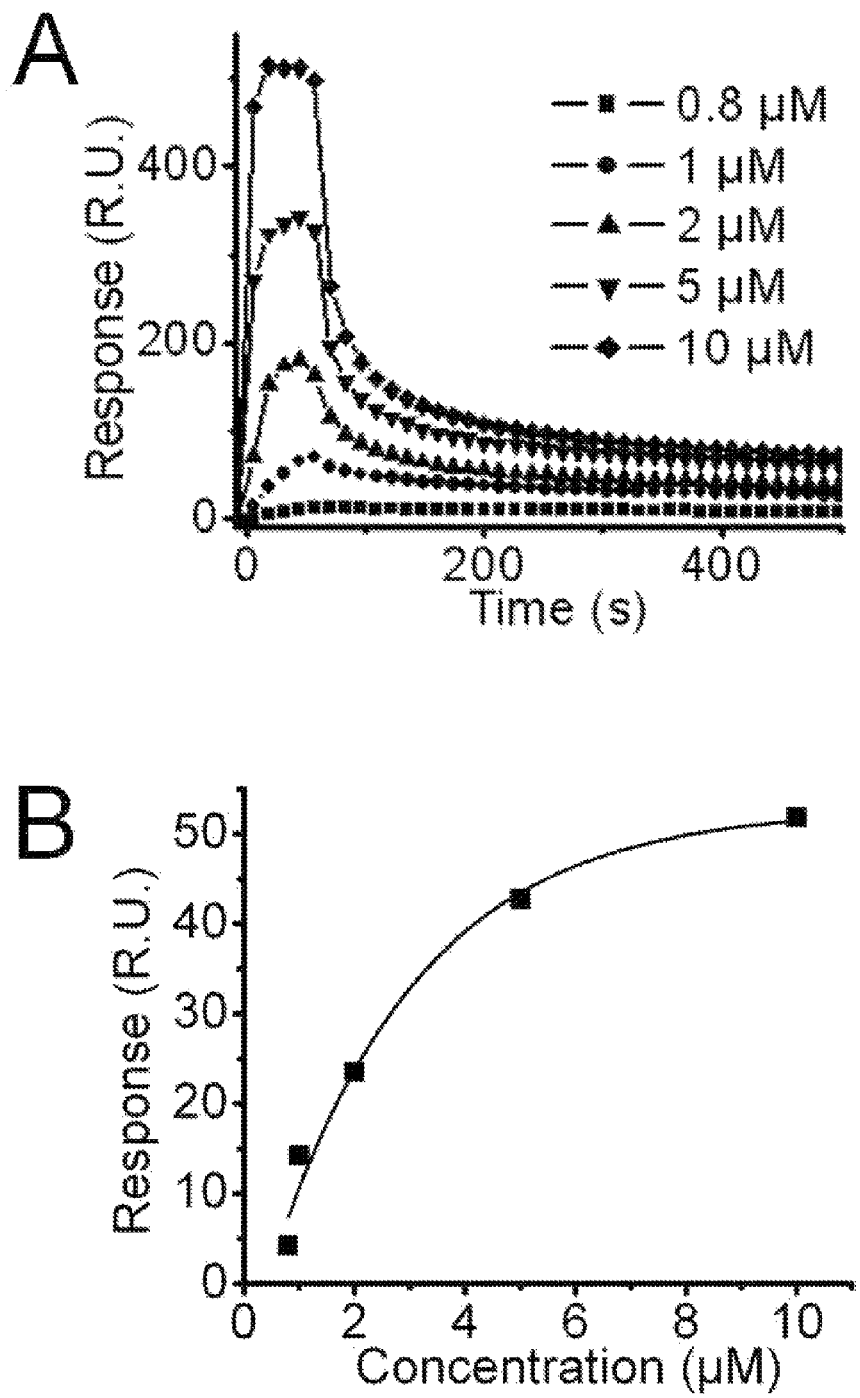
FIG. 18 depicts a mechanism of NBD-Linker incorporation into the lipid membrane of PFC nanoparticles. A. Incorporation of NBD-Linker into the PFC nanoparticles. Sensorgram, acquired by BIAcore X100, depicts the kinetics of the NBD-Linker incorporation into the PFC nanoparticles, which are immobilized on the surface of a L1 sensor chip. The NBD-Linker concentrations were 0.8, 1, 2, 5, and 10 μM. B. Stable incorporation of NBD-Linker incorporation onto PFC nanoparticles at various loading concentrations. C. Secondary structural change of NBD-Linker after lipid insertion, which was measured by circular dichroism spectroscopy. Free NBD-Linker (light grey) presented unordered structure; while lipid bounded NBD-Linker (black) adopted α-helical structure. D. Relative location of Tryptophans of NBD-Linker in PFC nanoparticles. Fluorescence emission spectra demonstrating both quenching and blue shift of endogenous tryptophan fluorescence of NBD-Linker. NBD-Linker concentration was 40 μM. The lipid:peptide ratio was 10.
Figure 18:
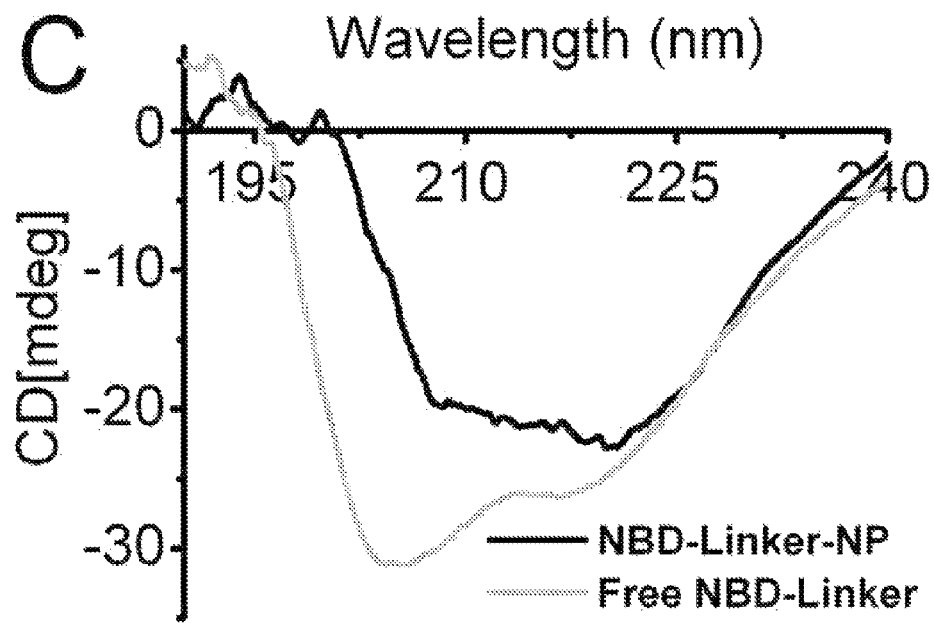
Figure 18:
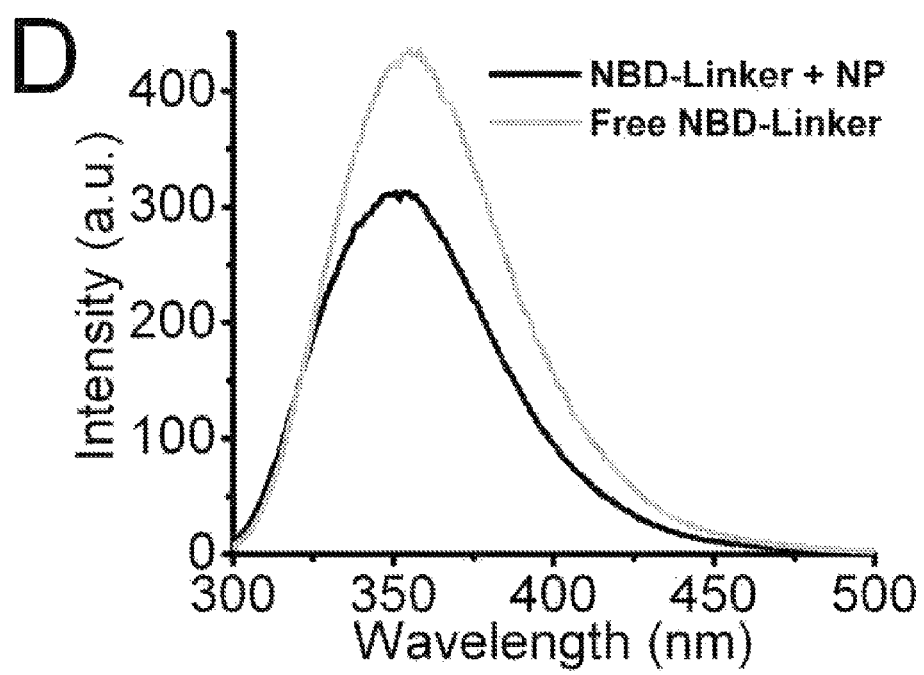

To investigate the release rate of the NBD-Linker from the PFC nanoparticles, surface plasma resonance experiments were performed with a Biacore X 100, which allows quantitative analysis of interaction between peptide and lipid membrane [26]. Consistent with our previous study [19], immobilization of PFC nanoparticles onto the L1 sensor chip surface results in maximal response of 4000 RU, which implies complete coverage of the senor surface by nanoparticles. NBD-Linker peptide at selected concentrations was injected at 30 µl/min for 1 minute into the detection flow cell, which contains a volume of 0.06 µl. After injection, a one-hour wash with running buffer followed. The kinetics of interaction between NBD-Linker and immobilized PFC nanoparticles are illustrated by the sensorgrams shown in FIG. 18A. We consistently recorded two populations of peptides in the peptide-lipid interactions. One population is loosely attached to the PFC nanoparticles and is quickly washed away. The other population is tightly incorporated into the PFC nanoparticles, and remains associated with PFC nanoparticles after 1 hour washing. The dissociation constant of the entire process is 0.14 µM. Also, the more NBD-Linker is injected, the more NBD-Linker remains with PFC nanoparticles (FIG. 18B).

By measuring the circular dichroism (CD) spectra of free NBD-Linker and PFC nanoparticle incorporated NBD-Linker, the results show that NBD-Linker peptide retains α-helical secondary structure after the incorporation into the PFC nanoparticles. In FIG. 18C, the CD spectrum of free peptide presents a strong negative peak near 200 nm and another negative band near 220 nm, which suggests the random coil unordered form. Conversely, the CD spectrum of the incorporated peptide exhibits two minimum at 222 and 208 nm and a maximum between 190-195 nm, which demonstrates the α-helical secondary structure.

To define the relative location (or proximity) of the NBD-Linker with respect to the core perfluorocarbon structures, we created PFC nanoparticles with a perfluorooctyl bromide (PFOB) core, the bromine atoms of which would be expected to quench the fluorescent tryptophan atoms in the NBD-Linker by Förster resonance energy transfer (FRET), if they are sufficiently close. It is also known that when tryptophan residue inserted into the lipids without quencher, its endogenous fluorescence emission spectrum exhibits a blue shift due to the hydrophobic environment [27]. The tryptophan emission spectra of free NBD-Linker and the NBD-linker mixed with PFOB nanoparticles are measured and shown in FIG. 18D. The results demonstrated that the addition of the nanoparticles resulted in both quenching and blue shift (leftward peak) of the tryptophan emission spectra from the incorporated linker peptides, with the residual tryptophan signal emanating from the remaining free surrounding peptide.

Metered NF-κB Signaling Modulation

F8 cells were treated with PFC nanoparticles loaded with selected amounts of the NBD-Linkers to evaluate the dose dependence response. After treatment, nuclear proteins were extracted from the F8 cells to determine the amount of NF-κB in the nucleus. The results demonstrated that NBD-Linker incorporated PFC nanoparticles inhibited the nuclear translocation of the P65, NF-κB protein. Furthermore, the higher the dose, the less of P65 is measured in the extracted nuclear protein (FIG. 19A). To further confirm that the inhibition effect is induced by NBD, we generated mutant NBD (mutNBD, see sequence in Materials and Methods) loaded nanoparticles by using the peptide linker. Nanoparticles loaded with mutNBD did not affect P65 nuclear translocation (FIG. 19B). To check functional inhibition of gene transcription and translation, we examined responses of ICAM-1 level, which is expressed on the surface of the F8 cells in response to NF-κB mediation [28]. The results indicate clearly that the ICAM-1 expression is suppressed by the treatment with NBD-Linker incorporated PFC nanoparticles (FIG. 19C). The mean fluorescence intensity from the F8 cells without treatment or treated with mutNBD-Linker loaded nanoparticles (162.83±9.99 or 146.31±3.62415, respectively) is more than 2-fold stronger than that from the F8 with the treatment of NBD-Linker loaded nanoparticles (73.29±3.56) (FIG. 19D). The Akt signaling pathway is upstream of NF-κB. We show that NBD incorporated nanoparticles do not affect either total Akt (tAkt) or phosphorylated Akt (pAkt) level in F8 cells (FIGS. 19E and F).

Discussion

Our results show that the PFC nanoparticle size and integrity are not affected by NBD-Linker loading, while the surface charge of the NBD-Linker loaded PFC nanoparticles is shifted to the more positive range. Furthermore, we employed fluorescence probe to visualize the lipid loading of NBD-Linker. Scanning confocal microscopy confirmed colocalization of NBD-Linker with the lipid membrane of the GUV and demonstrated that the lipid membrane barrier was intact after the incorporation of the peptide drug. Moreover, FCS results demonstrate that the mobility of the nanoparticles is not affected by the loading of the NBD-Linker peptides. These results verified incorporation of NBD-Linker into the lipid membrane of the delivery vehicle, and the integrity of the PFC nanoparticles retained after the peptide incorporation.

After confirming NBD-Linker incorporation into the lipid membrane of PFC nanoparticles, we studied the mechanism of peptide drug loading by investigating peptide lipid interaction. With the use of SPR to study the kinetics of peptide drug loading, we found that the NBD-Linker interacts with lipid membrane by both electrostatic and hydrophobic interaction.

One population, which interacts with PFC nanoparticles through electrostatic interaction, is loosely attached to the PFC nanoparticles and is quickly washed away. The other population, which interacts with PFC nanoparticles through hydrophobic interaction, is tightly incorporated into the PFC nanoparticles, and remains associated with PFC nanoparticles after 1 hour washing. Considering that the volume of the testing chamber is 0.06 µl, and the chamber was washed with 3600 µl of running buffer at constant flow rate, these results suggest that the NDB-Linker incorporation is quite stable. Consistently, as the amphipathic peptides integrate into the lipid membrane, they undergo conformational change and assume an α-helical secondary structure. The hydrophobic interaction between α-helical segment of the peptide and the surrounding lipid induce a negative free energy change, which maintains system stability [30]. This α-helical formation of membrane incorporated NBD-Linker was confirmed by the CD spectra.

Figure 20:
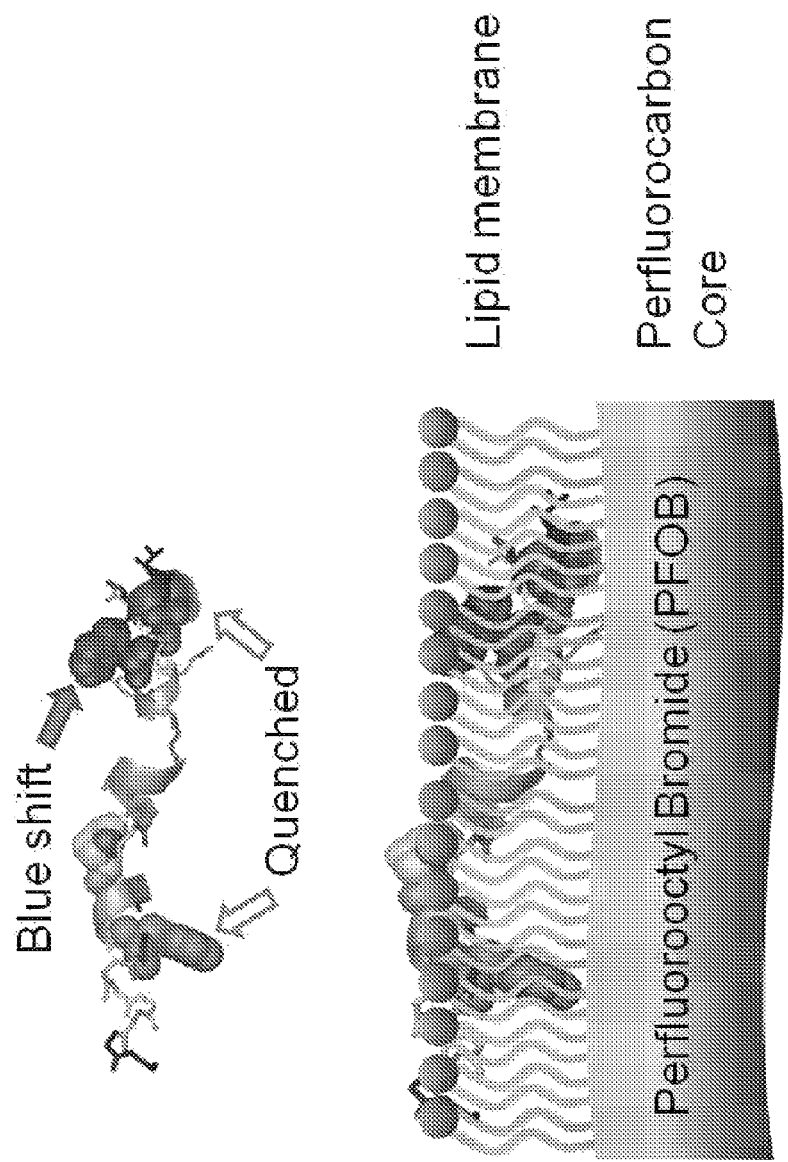
FIG. 20 depicts a schematic of relative location of NBD-Linker incorporated into lipid membrane of PFC nanoparticles. Top: NBD-Linker in α-helical structure. Three tryptophans are highlighted with purple spheres and pointed by arrows. Bottom: NBD-Linker incorporated into the lipid monolayer of PFOB nanoparticle. Two tryptophans, (white arrows), are close to the PFOB core. The fluorescence of these two tryopphans was quenched by PFOB; while the third Tryptophan in the lipid membrane was away from the PFOB core, which contributed to the blue shift of the tryptophan emission spectra.

Previously, we demonstrated that the tryptophan fluorescence of melittin is quenched after melittin incorporated into the nanoparticles with PFOB core, which indicates that the tryptophan residue of melittin is located at the tail region of the lipid monolayer and very close to the PFOB core of the nanoparticles [19]. After NBD-Linker incorporated into the lipid membrane of PFOB nanoparticles, the tryptophan fluorescence spectra exhibited both quenching and blue shift. These results suggested that some of the tryptophan residues on the NBD-Linker are located close to the core of the PFOB nanoparticles, while others settle in the lipid membrane away from the hydrophobic core. As illustrated in FIG. 20, the NBD-Linker has three tryptophan residues. After NBD-Linker peptides incorporated into the lipid membrane and formed the α-helic secondary structure, two of the tryptophan residues face the same direction, which could be in proximity to the core of the PFC nanoparticle, while the third one could face the opposite direction in the lipid membrane but away from the core and not quenched by the bromine.

Next, the functional activity of the PFC nanoparticles loaded with NBD-Linker was assessed by investigating NF-κB activation, namely NF-κB nuclear translocation and the expression of the NF-κB dependent genes. To evaluate the therapeutic effect of this NF-κB modulating nanoparticle, we employed a leukemia/lymphoma cell line (F8), which manifests constitutive NF-κB activation [31]. This cell line is derived from a large granular lymphocytic (LGL) leukemia transgenic mice model [32], which faithfully represents the leukemia/lymphoma induced by Tax promoter expression, resulting in morphology and phenotype of F8 cells in vitro that are indistinguishable from those observed in vivo [28, 32]. Tax, a transactivator protein, is encoded in the genome of HTLV-1, and is critical in promoting transformation of the cells [10, 33]. In F8 cells with Tax expression, NF-κB is activated constitutively [34].

Under physiological conditions, NF-κB is sequestered in the cytoplasm as an inactive complex with the inhibitory protein IκB. Under pathological conditions, such as infection, IκB is phosphorylated by the activated IKK complex. This phosphorylation results in unbiquitination and degradation of IκB. Consequently, NF-κB is free to translocate to the nucleus where it initiates the expression of NF-κB dependent genes. The IKK complex consists of two catalytic subunits, IKKα/IKKβ, and one regulatory subunit, IKKγ (also known as NEMO) [35-37]. By interrupting the interaction between IKKγ and the NEMO Binding Domain (NBD) on the carboxyl-terminal of IKKα/IKKβ, the activation of IKK complex can be inhibited, which in turn prohibits the subsequent phosphorylation of I-κB and activation of NF-κB. Thus, the NBD peptide inhibits NF-κB activation by preventing subunit interactions in the IKK complex, while mutNBD peptide is not capable of doing so [11].

If the activation of the NF-κB signaling pathway is inhibited, less NF-κB will translocate into the nucleus. For NF-κB signaling, P65 is the resultant transcription factor controlling gene expression in classical NF-κB activation. Thus, we compared the nuclear P65 between F8 cells without and with the inhibitory treatment at different dosages. The observed dose dependent suppression of the nuclear levels of constitutively activated NF-κB is precisely the desired outcome. At the same time, this NF-κB inhibitory nanoparticle did not affect the upstream signaling pathway, e.g. Akt signaling. These results suggest a specific inhibitory effect of NBD incorporated nanoparticles on NF-κB activation, and validate this peptide-nanoparticle as a promising delivery system.

In summary, we have formulated, characterized, and evaluated the function of a nanoparticle that inhibits NF-κB activation by using a flexible cargo linker peptide. One of the challenges in formulating therapeutic peptides into the delivery vehicles is the preservation of the activity of the peptide throughout the formulation procedures. The peptide linker strategy proposed here enables the addition of therapeutic peptide into the nanoparticles after their formulation. Therefore, therapeutic peptide could be loaded on the delivery nanoparticles in a simple mixing step without encountering harsh particle formulation steps, and the activity of the therapeutic peptide remains intact, which should facilitate sterile preparation of such compounds. This peptide linker strategy in conjunction with lipidic nano-delivery vehicles, either wholly synthetic or native, exemplifies a promising method of delivering small peptides for signaling pathway modulation.

References for Example 8

[1] Karin M, Cao Y, Greten F R, Li Z W. NF-kappaB in cancer: from innocent bystander to major culprit. Nat Rev Cancer 2002; 2:301-310.

[2] Karin M. Nuclear factor-kappaB in cancer development and progression. Nature 2006; 441:431-436.

[3] Pasparakis M. Regulation of tissue homeostasis by NF-kappaB signalling: implications for inflammatory diseases. Nat Rev Immunol 2009; 9:778-788.

[4] Bhoj V G, Chen Z J. Ubiquitylation in innate and adaptive immunity. Nature 2009; 458:430-437.

[5] Garg A, Aggarwal B B. Nuclear transcription factor-kappaB as a target for cancer drug development. Leukemia 2002; 16:1053-1068.

[6] Baud V, Karin M. Is NF-kappaB a good target for cancer therapy? Hopes and pitfalls. Nat Rev Drug Discov 2009; 8:33-40.

[7] Lopez-Guerra M, Colomer D. NF-kappaB as a therapeutic target in chronic lymphocytic leukemia. Expert Opin Ther Targets 2010; 14:275-288.

[8] Smale S T. Selective transcription in response to an inflammatory stimulus. Cell 2010; 140:833-844.

[9] Bellmann-Sickert K, Beck-Sickinger A G. Peptide drugs to target G protein-coupled receptors. Trends Pharmacol Sci 2010 (In Press).

[10] Bidwell G L, 3rd, Raucher D. Therapeutic peptides for cancer therapy. Part I—peptide inhibitors of signal transduction cascades. Expert Opin Drug Deliv 2009; 6:1033-1047.

[11] May M J, D'Acquisto F, Madge L A, Glockner J, Pober J S, Ghosh S. Selective inhibition of NF-kappaB activation by a peptide that blocks the interaction of NEMO with the IkappaB kinase complex. Science 2000; 289:1550-1554.

[12] Acharyya S, Villalta S A, Bakkar N, Bupha-Intr T, Janssen P M, Carathers M, et al. Interplay of IKK/NF-kappaB signaling in macrophages and myofibers promotes muscle degeneration in Duchenne muscular dystrophy. J Clin Invest 2007; 117:889-901

[13] Weissmann G, Hirschhorn R, Krakauer K. Effect of melittin upon cellular and lysosomal membranes. Biochem Pharmacol 1969; 18:1771-1775.

[14] Soman N R, Baldwin S L, Hu G, Marsh J N, Lanza G M, Heuser J E, et al. Molecularly targeted nanocarriers deliver the cytolytic peptide melittin specifically to tumor cells in mice, reducing tumor growth. J Clin Invest 2009; 119: 2830-2842.

[15] Caruthers S D, Cyrus T, Winter P M, Wickline S A, Lanza G M. Anti-angiogenic perfluorocarbon nanoparticles for diagnosis and treatment of atherosclerosis. Wiley Interdiscip Rev Nanomed Nanobiotechnol 2009; 1:311-323.

[16] Kaneda M M, Caruthers S, Lanza G M, Wickline S A. Perfluorocarbon nanoemulsions for quantitative molecular imaging and targeted therapeutics. Ann Biomed Eng 2009; 37:1922-1933.

[17] Pan H, Myerson J W, Ivashyna O, Soman N R, Marsh J N, Hood J L, et al. Lipid membrane editing with peptide cargo linkers in cells and synthetic nanostructures. Faseb J 2010; 24:2928-2937.

[18] Lanza G M, Winter P M, Caruthers S D, Hughes M S, Cyrus T, Marsh J N, et al. Nanomedicine opportunities for cardiovascular disease with perfluorocarbon nanoparticles. Nanomedicine (Lond) 2006; 1:321-329.

[19] Soman N R, Lanza G M, Heuser J M, Schlesinger P H, Wickline S A. Synthesis and characterization of stable fluorocarbon nanostructures as drug delivery vehicles for cytolytic peptides. Nano Lett 2008; 8:1131-1136.

[20] Angelova M I, Dimitrov S D. Liposome electroformation. Faraday Discuss Chem Soc 1986; 81:303-311.

[21] Rigler R, Elson E S, editors. Fluorescence correlation spectroscopy: theory and applications. Berlin: Springer, 2001.

[22] Petrasek Z, Schwille P. Precise measurement of diffusion coefficients using scanning fluorescence correlation spectroscopy. Biophys J 2008; 94:1437-1448.

[23] Rhoades E, Ramlall T F, Webb W W, Eliezer D. Quantification of alpha-synuclein binding to lipid vesicles using fluorescence correlation spectroscopy. Biophys J 2006; 90:4692-4700.

[24] Bacia K, Schwille P. Fluorescence correlation spectroscopy. Methods Mol Biol 2007; 398:73-84.
[25] Hess S T, Huang S, Heikal A A, Webb W W. Biological and chemical applications of fluorescence correlation spectroscopy: a review. Biochemistry 2002; 41:697-705.
[26] Torreri P, Ceccarini M, Macioce P, Petrucci T C. Biomolecular interactions by surface plasmon resonance technology. Ann 1st Super Sanita 2005; 41:437-441.
[27] Lakowicz J R. Principles of fluorescence spectroscopy. 2nd ed. New York: Kluwer Academic/Plenum Press, 1999.
[28] Grossman W J, Ratner L. Cytokine expression and tumorigenicity of large granular lymphocytic leukemia cells from mice transgenic for the tax gene of human T-cell leukemia virus type I. Blood 1997; 90:783-794.
[29] Winter P M, Cai K, Caruthers S D, Wickline S A, Lanza G M. Emerging nanomedicine opportunities with perfluorocarbon nanoparticles. Expert Rev Med Devices 2007; 4:137-145.
[30] Klocek G, Schulthess T, Shai Y, Seelig J. Thermodynamics of melittin binding to lipid bilayers. Aggregation and pore formation. Biochemistry 2009; 48:2586-2596.
[31] Bernal-Mizrachi L, Lovly C M, Ratner L. The role of NF-{kappa}B-1 and NF-{kappa}B-2-mediated resistance to apoptosis in lymphomas. Proc Natl Acad Sci USA 2006; 103:9220-9225.
[32] Grossman W J, Kimata J T, Wong F H, Zutter M, Ley T J, Ratner L. Development of leukemia in mice transgenic for the tax gene of human T-cell leukemia virus type I. Proc Natl Acad Sci USA 1995; 92:1057-1061.
[33] Boxus M, Twizere J C, Legros S, Dewulf J F, Kettmann R, Willems L. The HTLV-1 Tax interactome. Retrovirology 2008; 5:76-99.
[34] Sun S C, Ballard D W. Persistent activation of NF-kappaB by the tax transforming protein of HTLV-1: hijacking cellular IkappaB kinases. Oncogene 1999; 18:6948-6958.
[35] Karin M. The beginning of the end: IkappaB kinase (IKK) and NF-kappaB activation. J Biol Chem 1999; 274: 27339-27342.
[36] Rothwarf D M, Zandi E, Natoli G, Karin M. IKK-gamma is an essential regulatory subunit of the IkappaB kinase complex. Nature 1998; 395:297-300.
[37] Yamaoka S, Courtois G, Bessia C, Whiteside S T, Weil R, Agou F, et al. Complementation cloning of NEMO, a component of the IkappaB kinase complex essential for NF-kappaB activation. Cell 1998; 93:1231-1240.

What is claimed is:

1. A nanoparticle, the nanoparticle comprising a core encapsulated by a lipid layer, the lipid layer comprising a stably inserted anchor peptide, wherein the anchor peptide is substantially non-lytic, non-cytotoxic, consists of an amino acid sequence selected from the group consisting of SEQ ID NOs:5-218, and has an association rate of at least about $9 \times 10^5$ $M^{-1}$ $s^{-1}$ and a dissociation constant of less than about $1 \times 10^{-6}$ M.

2. The nanoparticle in of claim 1, wherein the anchor peptide consists of SEQ ID NO:88.

3. The nanoparticle of claim 1, wherein the anchor peptide is conjugated to at least one cargo complex selected from the group consisting of an imaging cargo, a therapeutic cargo, a cytotoxic cargo, and a targeting cargo.

4. A kit for preparing a nanoparticle comprising an anchor peptide, the kit comprising a first composition and a second composition, the first composition comprising a nanoparticle comprising a core encapsulated by a lipid layer, the second composition comprising the anchor peptide which is substantially non-lytic, non-cytotoxic, consists of an amino acid sequence selected from the group consisting of SEQ ID NOs: 5-218, and has an association rate of at least about $9 \times 10^5$ $M^{-1}$ $s^{-1}$ and a dissociation constant of less than about $1 \times 10^{-6}$ M.

5. The kit of claim 4, wherein the anchor peptide consists of SEQ ID NO:88.

6. The kit of claim 4, wherein the anchor peptide is conjugated to a cargo complex selected from the group consisting of an imaging cargo, a therapeutic cargo, a cytotoxic cargo, and a targeting cargo.

7. A method for adding a cargo complex to a nanoparticle comprising a lipid layer, the method comprising contacting the nanoparticle with an anchor peptide that is conjugated to the cargo complex, the anchor peptide being substantially non-lytic, non-cytotoxic, and consisting of an amino acid sequence selected from the group consisting of SEQ ID NOs: 5-218 with an association rate of at least about $9 \times 10^5$ $M^{-1}$ $s^{-1}$ and a dissociation constant of less than about $1 \times 10^{-6}$ M, wherein the anchor peptide stably inserts into the lipid layer of the nanoparticle.

8. The method of claim 7, wherein the cargo complex is selected from the group consisting of an imaging cargo, a therapeutic cargo, a cytotoxic cargo, and a targeting cargo.

* * * * *